US011280790B2

(12) United States Patent
Tovey et al.

(10) Patent No.: US 11,280,790 B2
(45) Date of Patent: Mar. 22, 2022

(54) SYSTEM AND PRODUCTS FOR IMPROVED QUANTIFICATION OF ADCC ACTIVITY

(71) Applicant: SVAR LIFE SCIENCE AB, Malmö (SE)

(72) Inventors: Michael Tovey, Paris (FR); Christophe Lallemand, Paris (FR)

(73) Assignee: SVAR LIFE SCIENCE AB, Malmö (SE)

( * ) Notice: Subject to any disclaimer, the term of this patent is extended or adjusted under 35 U.S.C. 154(b) by 195 days.

(21) Appl. No.: 16/339,327

(22) PCT Filed: Mar. 10, 2017

(86) PCT No.: PCT/EP2017/075053
§ 371 (c)(1),
(2) Date: Apr. 3, 2019

(87) PCT Pub. No.: WO2018/065401
PCT Pub. Date: Apr. 12, 2018

(65) Prior Publication Data
US 2019/0310251 A1  Oct. 10, 2019

(30) Foreign Application Priority Data
Oct. 4, 2016  (EP) ................... 16192246

(51) Int. Cl.
| G01N 33/569 | (2006.01) |
| C12N 9/22 | (2006.01) |
| C12N 15/86 | (2006.01) |
| G01N 33/50 | (2006.01) |
| C12N 15/63 | (2006.01) |

(52) U.S. Cl.
CPC ......... *G01N 33/56966* (2013.01); *C12N 9/22* (2013.01); *C12N 15/63* (2013.01); *C12N 15/86* (2013.01); *G01N 33/505* (2013.01); *G01N 33/5014* (2013.01); *G01N 33/5044* (2013.01); *C12N 2800/80* (2013.01)

(58) Field of Classification Search
CPC ......... G01N 33/56966; G01N 33/5014; G01N 33/5044; G01N 33/505; C12N 15/63; C12N 9/22; C12N 15/86; C12N 2800/80; C12Q 1/6897
See application file for complete search history.

(56) References Cited

U.S. PATENT DOCUMENTS 5,874,304 A * 2/1999 Zolotukhin ...... C07K 14/43595
435/320.1
2011/0189658 A1 8/2011 Tovey et al.

FOREIGN PATENT DOCUMENTS

WO  2012121911 A2  9/2012

OTHER PUBLICATIONS

Aramburu et al., "Activation and expression of the nuclear factors of activated T cells, NFATp and NFATc, in human natural killer cells: regulation upon CD16 ligand binding." J Exp Med. Sep. 1, 1995; 182(3):801-10.
Cheng et al., "Development of a robust reporter-based ADCC assay with frozen, thaw-and-use cells to measure Fc effector function of therapeutic antibodies." J Immunol Methods. Dec. 1, 2014; 414:69-81.
Haubert et al., "Vav1 couples the T cell receptor to cAMP response element activation via a PKC-dependent pathway." Cell Signal. Jun. 2010;22(6):944-54.
Kaiser et al., "MSK regulate TCR-induced CREB phosphorylation but not immediate early gene transcription." Eur J Immunol. Sep. 2007;37(9):2583-95.
Nash et al., "Bovine IgG1, but not IgG2, binds to human B cells and inhibits antibody secretion." Immunology. Mar. 1990;69(3):361-6.
Parekh et al., "Development and validation of an antibody-dependent cell-mediated cytotoxicity-reporter gene assay." MAbs. May-Jun. 2012;4(3):310-8.
Theile et al., "ATP-binding cassette transporters as pitfalls in selection of transgenic cells." Anal Biochem. Apr. 15, 2010; 399(2):246-50.
Christophe Lallemand et al., "Reporter gene assay for the quantification of the activity and neutralizing antibody response to TNF antagonists", Journal of Immunological Methods, pp. 229-239, vol. 373, No. 1 (Aug. 2011).
Christophe Lallemand et al.,"A Novel System for the Quantification of the ADCC Activity of Therapeutic Antibodies", Journal of Immunology Research, pp. 1-19, vol. 2017 (Jan. 2017).

(Continued)

Primary Examiner — Paul J Holland
(74) Attorney, Agent, or Firm — Casimir Jones, S.C.; Lisa Mueller

(57) ABSTRACT

The activity of a number of therapeutic antibodies is mediated in part by antibody-dependent cell-mediated cytotoxicity (ADCC). An engineered effector cell line expressing the low affinity Fc receptor, FcγR111a (CD16), that responds to ligation of the Fc moiety of antibody bound to the specific antigen expressed on target cells by activation of a NFAT responsive reporter gene is described. In this cell line the firefly luciferase (FL) reporter gene is regulated by a novel synthetic chimeric promoter containing binding sites for NF-AT, AP1, NFkB, and STAT5 that confers improved sensitivity, an improved dynamic range, an improved tolerance to human serum and a reduced incubation time, relative to engineered effector cell lines that express a NFAT regulated reporter-gene, when used in an ADCC assay together with engineered target cells. The target cells have been engineered to over-express a constant high level of the specific antigen recognized by the therapeutic antibody, and homologous control cells have been developed in which the gene encoding the specific drug target has been invalidated by genomic editing. Target cells that have been engineered to over-express a constant level of CD20 together with homologous control cell line, in which the gene encoding CD20 has been invalidated, have been used to quantify the ADCC activity of Rituxan with a high degree of precision and with minimal interference from human serum.

17 Claims, 33 Drawing Sheets

Specification includes a Sequence Listing.

(56) References Cited

OTHER PUBLICATIONS

Wu Yuling et al, "A Neutralizing Antibody Assay Based on a Reporter of Antibody-Dependent Cell-Mediated Cytotoxicity", The AAPS Journal, pp. 1417-1426, vol. 17, No. 6 (Jul. 2015.
Witham et al., "ANF-[kappa]B-Dependent Dual Promoter-Enhancer Initiates the Lipopolysaccharide-Mediated Transcriptional Activation of the Chicken Lysozyme in Macrophages", PLOS One, pp. 1-12, vol. 8., No. 3 (Mar. 2013).
Cheng et al.,"Development of a robust reporter-based ADCC assay with frozen, thaw-and-use cells to measure Fc effector function of therapeutic antibodies", Journal of Immunological Methods, pp. 69-81, vol. 414 (Jul. 2014).

\* cited by examiner

GGAAGCGAAAATGAAATTGACTGGACTTTCCGGAGGAAAAACTGTTTCATTACAGAAGGCGTGGATGTTCATAATTAGGATGAGTCAGTGACTTCAAGTTCAAGACCTGATTTCCCGAAATGATGAGCTAG

NFκB    NFAT1    AP-1   CREB    STAT1/4/5

Fig. 1

GGCCTATTGCTATGCAATC

Fig. 4

TCATCGCTCACAACCAAGTG

Fig. 12

|  | iLite® | NFAT effector cells |
|---|---|---|
| Top | 253.5 | 15.55 |
| Bottom | -2.532 | 1.005 |
| LogIC50 | 0.86 | 1.592 |
| HillSlope | 1.24 | 1.206 |
| IC50 | 7.244 | 39.09 |
| Span | 256 | 14.55 |

```
         10         20         30         40         50
MSTESMIRDV ELAEEALPKK TGGPQGSRRC LFLSLFSFLI VAGATTLFCL
         60         70         80         90        100
                     LL

LHFGVIGPQR EEFPRDLSLI SPLAQAVRSS SRTPSDKPVA HVVANPQAEG
        110        120        130        140        150
QLQWLNRRAN ALLANGVELR DNQLVVPSEG LYLIYSQVLF KGQGCPSTHV
        160        170        180        190        200
LLTHTISRIA VSYQTKVNLL SAIKSPCQRE TPEGAEAKPW YEPIYLGGVF
        210        220        230
QLEKGDRLSA EINRPDYLDF AESGQVYFGI IAL
```

Fig. 17

TNFRSF1A: ATATACCCCT CAGGGGTTAT

TNFRSF1B: CACCGTGTGT GACTCCTGTG

Fig. 18

SEQUENCE LISTING

```
<160> NUMBER OF SEQ ID NOS: 12

<210> SEQ ID NO 1
<211> LENGTH: 125
<212> TYPE: DNA
<213> ORGANISM: Artificial Sequence
<220> FEATURE:
<223> OTHER INFORMATION: Synthetic

<400> SEQUENCE: 1
ggaagcgaaa atgaaattga ctgggacttt ccggaggaaa aactgtttca tacagaaggc      60
gtggatgtcc atattaggat gagtcagtga cgtcagagcc tgatttcccc gaaatgatga     120
gctag                                                                 125

<210> SEQ ID NO 2
<211> LENGTH: 9220
<212> TYPE: DNA
<213> ORGANISM: Artificial Sequence
<220> FEATURE:
<223> OTHER INFORMATION: Synthetic

<400> SEQUENCE: 2
gttaggcgtt ttgcgctgct tcgcgatgta cgggccagat atacgcgttg acattgatta      60
ttgactagtt attaatagta atcaattacg gggtcattag ttcatagccc atatatggag     120
ttccgcgtta cataacttac ggtaaatggc ccgcctggct gaccgcccaa cgacccccgc     180
ccattgacgt caataatgac gtatgttccc atagtaacgc caatagggac tttccattga     240
cgtcaatggg tggagtattt acggtaaact gcccacttgg cagtacatca agtgtatcat     300
atgccaagta cgccccctat tgacgtcaat gacggtaaat ggcccgcctg gcattatgcc     360
cagtacatga ccttatggga ctttcctact tggcagtaca tctacgtatt agtcatcgct     420
```

```
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
agcggccgcc accatgggca agcccatccc taacccctg ttggggctgg acagcaccgc    780
tcccaaaaag aaaaggaagg tgggcattca cggcgtgcct gcggccgaca aaaagtacag    840
catcggcctt gatatcggca ccaatagcgt gggctgggcc gttatcacag acgaatacaa    900
ggtacccagc aagaagttca aggtgctggg aatacagac aggcactcta tcaagaaaaa    960
ccttatcggg gctctgctgt ttgactcagg cgagaccgcc gaggccacca ggttgaagag   1020
gaccgcaagg cgaaggtaca cccggaggaa gaacaggatc tgctatctgc aggagatctt   1080
cagcaacgag atggccaagg tggacgcacag cttcttccac aggctggagg agagcttcct   1140
tgtcgaggag gataagaagc acgaacgaca ccccatcttc ggcaacatag tcgacgaggt   1200
cgcttatcac gagaagtacc ccaccatcta ccacctgcga aagaaattgg tggatagcac   1260
cgataaagcc gacttgcgac ttatctactt ggctctggcg cacatgatta agttcagggg   1320
ccacttcctg atcgagggcg accttaaccc cgacaacagt gacgtagaca aattgttcat   1380
ccagcttgta cagacctata accagctgtt cgaggaaaac cctattaacg ccagcggggt   1440
ggatgcgaag gccatactta gcgccaggct gagcaaaagc aggcgcttgg agaacctgat   1500
agcccagctc cccggtgaaa agaagaacgg cctcttcggt aatctgattg ccctgagcct   1560
gggcctgacc cccaacttca gagcaacttc gacctggca gaagatgcca agctgcagtt   1620
gagtaaggac acctatgacg acgacttgga caatctgctc gcccaaatcg gcgaccagta   1680
cgctgacctg ttcctcgccg ccaagaacct ttctgacgca atcctgctta gcgatatcct   1740
tagggtgaac acagagatca ccaaggcccc cctgagcgcc agcatgatca gaggtacga   1800
cgagcaccat caggacctga cccttctgaa ggccctggtg aggcagcaac tgcccgagaa   1860
gtacaaggag atcttttttcg accagagcaa gaacggctac gccggctaca tcgacggcgg   1920
agccagccaa gaggagttct acaagttcat caagcccatc ctggagaaga tggatggcac   1980
cgaggagctg ctggtgaagc tgaacaggga agatttgctc cggaagcaga ggaccttga   2040
caacggtagc atccccacc agatccacct gggcgagctg cacgcaatac tgaggcgaca   2100
ggaggatttc taccccttcc tcaaggacaa tagggagaaa atcgaaaaga ttctgacctt   2160
caggatcccc tactacgtgg gccctcttgc caggggcaac agccgattcg cttggatgac   2220
aagaaagagc gaggagacca tcacccctg gaacttcgag gaagtggtgg acaaaggagc   2280
aagcgcgcag tctttcatcg aacggatgac caatttcgac aaaaacctgc taacgagaa   2340
ggtgctgccc aagcacagcc tgctttacga gtacttcacc gtgtacaacg agctcaccaa   2400
ggtgaaatat gtgaccgagg gcatgcgaaa acccgctttc ctgagcggcg agcagaagaa   2460
ggccatcgtg gacctgctgt tcaagaccaa caggaaggtg accgtgaagc agctgaagga   2520
ggactacttc aagaagatcg agtgctttga tagcgtggaa ataagcggcg tggaggacag   2580
gttcaacgcc agcctgggca cctaccacga cttgttgaag ataatcaaag acaaggattt   2640
cctggataat gaggagaacg aggatatact cgaggacatc gtgctgactt tgaccctgtt   2700
tgaggaccga gagatgattg aagaaaggct caaaacctac gccacctgt tcgacgacaa   2760
agtgatgaaa caactgaaga gacgaagata caccggctgg ggcagactgt ccaggaagct   2820
```

```
catcaacggc attagggaca agcagagcgg caagaccatc ctggatttcc tgaagtccga   2880
cggcttcgcc aaccgaaact tcatgcagct gattcacgat gacagcttga ccttcaagga   2940
ggacatccag aaggcccagg ttagcggcca gggcgactcc ctgcacgaac atattgcaaa   3000
cctggcaggc tccctgcga tcaagaaggg catactgcag accgttaagg ttgtggacga   3060
attggtcaag gtcatgggca ggcacaagcc cgaaaacata gttatagaga tggccagaga   3120
gaaccagacc acccaaaagg gccagaagaa cagccgggag cgcatgaaaa ggatcgagga   3180
gggtatcaag gaactcggaa gccagatcct caaagagcac cccgtggaga ataccagct    3240 ccagaacgag aagctgtacc tgtactacct gcagaacggc agggacatgt acgttgacca   3300
ggagttggac atcaacaggc tttcagacta tgacgtggat cacatagtgc cccagagctt   3360
tcttaaagac gatagcatcg acaacaaggt cctgacccgc tccgacaaaa acaggggcaa   3420
aagcgacaac gtgccaagcg aagaggtggt aaaaagatg aagaactact ggaggcaact    3480
gctcaacgcg aaattgatca cccagagaaa gttcgataac ctgaccaagg ccgagagggg   3540
cggactctcc gaacttgaca aagcgggctt cataaagagg cagctggtcg agacccgaca   3600
gatcacgaag cacgtggccc aaatcctcga cagcagaatg aataccaagt acgatgagaa   3660
tgacaaactc atcagggaag tgaaagtgat taccctgaag agcaagttgg tgtccgactt   3720
tcgcaaagat ttccagttct acaaggtgag ggagatcaac aactaccacc atgcccacga   3780
cgcatacctg aacgccgtgg tcggcaccgc cctgattaag aagtatccaa agctggagtc   3840
cgaatttgtc tacggcgact acaaagttta cgatgtgagg aagatgatcg ctaagagcga   3900
acaggagatc ggcaaggcca ccgctaagta tttcttctac agcaacatca tgaactttt    3960 caagaccgag atcacacttg ccaacggcga aatcaggaag aggccgctta tcgagaccaa   4020
cggtgagacc ggcgagatcg tgtgggacaa gggcagggac ttcgccaccg tgaggaaagt   4080
cctgagcatg ccccaggtga atattgtgaa aaaaactgag gtgcagacag gcggctttag   4140
caaggaatcc atcctgccca gaggaacag cgacaagctg atcgcccgga agaaggactg    4200
ggaccctaag aagtatgagg gcttcgacag ccccaccgta gcctacagcg tgctggtggt   4260
cgcgaaggta gagaagggga agagcaagaa actgaagagc gtgaaggagc tgctcggcat   4320
aaccatcatg gagaggtcca gctttgagaa gaaccccatt gacttttggg aagccaaggg   4380
ctacaaagag gtcaaaaagg acctgatcat caaactcccc aagtactccc tgtttgaatt   4440
ggagaacggc agaaagagga tgctggcgag cgctgggaa ctgcaaaagg caacgaact    4500 ggcgctgccc agcaagtacg tgaattttct gtacctggcg tcccactacg aaaagctgaa   4560
aggcagcccc gaggacaacg agcagaagca gctgttcgtg gagcagcaca gcattacct    4620 ggacgagata atcgagcaaa tcagcgagtt cagcaagagg gtgattctgg ccgacgcgaa   4680
cctggataag gtcctcagcg cctacaacaa gcaccgagac aaacccatca gggagcaggc   4740
cgagaatatc atacacctgt tcaccctgac aaatctgggc gcacctgcgg cattcaaata   4800
cttcgatacc accatcgaca ggaaaaggta cactagcact aaggaggtgc tggatgccac   4860
cttgatccac cagtccatta ccggcctgta tgagaccagg atcgacctga gccagcttgg   4920
aggcgactct agggcggacc caaaaaagaa aaggaaggtg gaattctcta gaggcagtgg   4980
agagggcaga ggaagtctgc taacatgcgg tgacgtcgag gagaatcctg gcccaatgaa   5040
cctgagcaaa aacgtgagcg tgagcgtgta tatgaagggg aacgtcaaca atcatgagtt   5100
tgagtacgac ggggaaggtg gtggtgatcc ttatacaggt aaatattcca tgaagatgac   5160
```

```
gctacgtggt caaaattccc tacccttttc ctatgatatc attaccacgg catttcagta   5220
tggtttccgc gtatttacaa aatacctga gggaattgtt gactatttta aggactcgct    5280
tcccgacgca ttccagtgga acagacgaat tgtgtttgaa gatggtggag tactaaacat   5340
gagcagtgat atcacatata aagataatgt tctgcatggt gacgtcaagg ctgagggagt   5400
gaacttcccg ccgaatgggc cagtgatgaa gaatgaaatt gtgatggagg aaccgactga   5460
agaaacattt actccaaaaa acggggttct tgttggcttt tgtcccaaag cgtacttact   5520
taaagacggt tcctattact atggaaatat gacaacattt tacagatcca agaaatctgg   5580
ccaggcacct cctgggtatc actttgttaa gcatcgtctc gtcaagacca atgtgggaca   5640
tggatttaag acggttgagc agactgaata tgccactgct catgtcagtg atcttcccaa   5700
gttcgaagct tgataatgag tttaaacggg ggaggctaac tgaaacacgg aaggagacaa   5760
taccggaagg aacccgcgct atgacggcaa taaaagaca gaataaaacg cacgggtgtt    5820
gggtcgtttg ttcataaacg cggggttcgg tcccagggct ggcactctgt cgataccca    5880 ccgagacccc attggggcca atacgcccgc gtttcttcct tttccccacc caccccca     5940 agttcgggtg aaggcccagg gctcgcagcc aacgtcgggg cggcaggccc tgccatagca   6000
gatctgcgca gctgggctc taggggtat ccccacgcgc cctgtagcgg cgcattaagc     6060
gcggcgggtg tggtggttac gcgcagcgtg accgctacac ttgccagcgc cctagcgccc   6120
gctcctttcg ctttcttccc ttcctttctc gccacgttcg ccggctttcc ccgtcaagct   6180
ctaaatcggg ggctccctt agggttccga tttagtgctt tacggcacct cgaccccaaa    6240
aaacttgatt agggtgatgg ttcacgtagt gggccatcgc cctgatagac ggtttttcgc   6300
cctttgacgt tggagtccac gttctttaat agtggactct tgttccaaac tggaacaaca   6360
ctcaacccta tctcggtcta ttcttttgat ttataaggga ttttgccgat ttcggcctat   6420
tggttaaaaa atgagctgat ttaacaaaaa tttaacgcga attaattaag gtcgggcagg   6480
aagagggcct atttcccatg attccttcat atttgcatat acgatacaag ctgttagag    6540 agataattag aattaatttg actgtaaaca caagatatt agtacaaaat acgtgacgta    6600
gaaagtaata atttcttggg tagtttgcag ttttaaaatt atgttttaaa atggactatc   6660
atatgcttac cgtaacttga agtatttcg atttcttggc tttatatatc ttgtggaaag    6720
gacgaaacac cggatcatc agaagacccc ccgttttaga gctagaaata gcaagttaaa    6780
ataaggctag tccgttatca acttgaaaaa gtggcaccga gtcggtgctt ttttctagta   6840
taccgtcgac ctctagctag agcttggcgt aatcatggtc atagctgttt cctgtgtgaa   6900
attgttatcc gctcacaatt ccacacaaca tacgagccgg aagcataaag tgtaaagcct   6960
ggggtgccta atgagtgagc taactcacat taattgcgtt gcgctcactg cccgctttcc   7020
agtcgggaaa cctgtcgtgc cagctgcatt aatgaatcgg ccaacgcgcg gggagaggcg   7080
gtttgcgtat tgggcgctct tccgcttcct cgctcactga ctcgctgcgc tcggtcgttc   7140
ggctgcggcg agcggtatca gctcactcaa aggcggtaat acggttatcc acagaatcag   7200
gggataacgc aggaaagaac atgtgagcaa aaggccagca aaaggccagg aaccgtaaaa   7260
aggccgcgtt gctggcgttt ttccataggc tccgcccccc tgacgagcat cacaaaaatc   7320
gacgctcaag tcagaggtgg cgaaacccga caggactata aagataccag gcgtttcccc   7380
ctggaagctc cctcgtgcgc tctcctgttc cgaccctgcc gcttaccgga tacctgtccg   7440
cctttctccc ttcgggaagc gtggcgcttt ctcatagctc acgctgtagg tatctcagtt   7500
cggtgtaggt cgttcgctcc aagctgggct gtgtgcacga accccccgtt cagcccgacc   7560
```

```
gctgcgcctt atccggtaac tatcgtcttg agtccaaccc ggtaagacac gacttatcgc    7620
cactggcagc agccactggt aacaggatta gcagagcgag gtatgtaggc ggtgctacag    7680
agttcttgaa gtggtggcct aactacggct acactagaag aacagtattt ggtatctgcg    7740
ctctgctgaa gccagttacc ttcggaaaaa gagttggtag ctcttgatcc ggcaaacaaa    7800
ccaccgctgg tagcggtggt ttttttgttt gcaagcagca gattacgcgc agaaaaaaag    7860
gatctcaaga agatcctttg atcttttcta cggggtctga cgctcagtgg aacgaaaact    7920
cacgttaagg gattttggtc atgagattat caaaaaggat cttcacctag atccttttaa    7980
attaaaaatg aagttttaaa tcaatctaaa gtatatatga gtaaacttgg tctgacagtt    8040
accaatgctt aatcagtgag gcacctatct cagcgatctg tctatttcgt tcatccatag    8100
ttgcctgact ccccgtcgtg tagataacta cgatacggga gggcttacca tctggcccca    8160
gtgctgcaat gataccgcga gacccacgct caccggctcc agatttatca gcaataaacc    8220
agccagccgg aagggccgag cgcagaagtg gtcctgcaac tttatccgcc tccatccagt    8280
ctattaattg ttgccgggaa gctagagtaa gtagttcgcc agttaatagt ttgcgcaacg    8340
ttgttgccat tgctacaggc atcgtggtgt cacgctcgtc gtttggtatg gcttcattca    8400
gctccggttc ccaacgatca aggcgagtta catgatcccc catgttgtgc aaaaaagcgg    8460
ttagctcctt cggtcctccg atcgttgtca agtaagtt ggccgcagtg ttatcactca    8520
tggttatggc agcactgcat aattctctta ctgtcatgcc atccgtaaga tgcttttctg    8580
tgactggtga gtactcaacc aagtcattct gagaatagtg tatgcggcga ccgagttgct    8640
cttgcccggc gtcaatacgg gataataccg cgccacatag cagaacttta aaagtgctca    8700
tcattggaaa acgttcttcg gggcgaaaac tctcaaggat cttaccgctg ttgagatcca    8760
gttcgatgta acccactcgt gcacccaact gatcttcagc atcttttact ttcaccagcg    8820
tttctgggtg agcaaaaaca ggaaggcaaa atgccgcaaa aaagggaata agggcgacac    8880
ggaaatgttg aatactcata ctcttccttt ttcaatatta ttgaagcatt tatcagggtt    8940
attgtctcat gagcggatac atatttgaat gtatttagaa aaataaacaa ataggggttc    9000
cgcgcacatt tccccgaaaa gtgccacctg acgtcgacgg atcgggagat ctcccgatcc    9060
cctatggtgc actctcagta caatctgctc tgatgccgca tagttaagcc agtatctgct    9120
ccctgcttgt gtgttggagg tcgctgagta gtgcgcgagc aaaatttaag ctacaacaag    9180
gcaaggcttg accgacaatt gcatgaagaa tctgcttagg                          9220
```

<210> SEQ ID NO 3
<211> LENGTH: 9220
<212> TYPE: DNA
<213> ORGANISM: Artificial Sequence
<220> FEATURE:
<223> OTHER INFORMATION: Synthetic

<400> SEQUENCE: 3

```
gttaggcgtt ttgcgctgct tcgcgatgta cgggccagat atacgcgttg acattgatta     60
ttgactagtt attaatagta atcaattacg ggtcattag ttcatagccc atatatggag     120
ttccgcgtta cataacttac ggtaaatggc ccgcctggct gaccgcccaa cgacccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
```

-continued

```
cagtacatga ccttatggga ctttcctact tggcagtaca tctacgtatt agtcatcgct    420
attaccatgg tgatgcggtt ttggcagtac atcaatgggc gtggatacg gtttgactca     480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
agcggccgcc accatgggca agcccatccc taacccctg ttggggctgg acagcaccgc     780
tcccaaaaag aaaaggaagg tgggcattca cggcgtgcct gcggccgaca aaaagtacag    840
catcggcctt gatatcggca ccaatagcgt gggctgggcc gttatcacag acgaatacaa    900
ggtacccagc aagaagttca aggtgctggg aatacagac aggcactcta tcaagaaaaa     960
ccttatcggg gctctgctgt ttgactcagg cgagaccgcc gaggccacca ggttgaagag   1020
gaccgcaagg cgaaggtaca cccggaggaa gaacaggatc tgctatctgc aggagatctt   1080
cagcaacgag atggccaagg tggacgacag cttcttccac aggctggagg agagcttcct   1140
tgtcgaggag gataagaagc acgaacgaca ccccatcttc ggcaacatag tcgacgaggt   1200
cgcttatcac gagaagtacc ccaccatcta ccacctgcga aagaaattgg tggatagcac   1260
cgataaagcc gacttgcgac ttatctactt ggctctggcg cacatgatta agttcagggg   1320
ccacttcctg atcgagggcg accttaaccc cgacaacagt gacgtagaca aattgttcat   1380
ccagcttgta cagacctata accagctgtt cgaggaaaac cctattaacg ccagcggggt   1440
ggatgcgaag gccatactta cgccaggct gagcaaaagc aggcgcttgg agaacctgat    1500
agcccagctg cccggtgaaa agaagaacgg cctcttcggt aatctgattg ccctgagcct   1560
gggcctgacc cccaacttca agagcaactt cgacctggca gaagatgcca agctgcagtt   1620
gagtaaggac acctatgacg acgacttgga caatctgctc gcccaaatcg gcgaccagta   1680
cgctgacctg ttcctcgccg ccaagaacct ttctgacgca atcctgctta gcgatatcct   1740
tagggtgaac acagagatca ccaaggcccc cctgagcgcc agcatgatca agaggtacga   1800
cgagcaccat caggacctga cccttctgaa ggccctggtg aggcagcaac tgcccgagaa   1860
gtacaaggag atcttttttcg accagagcaa gaacggctac gccggctaca tcgacggcgg   1920
agccagccaa gaggagttct acaagttcat caagcccatc ctggagaaga tggatggcac   1980
cgaggagctg ctggtgaagc tgaacaggga agatttgctc cggaagcaga ggacctttga   2040
caacggtagc atccccacc agatccacct gggcgagctg cacgcaatac tgaggcgaca   2100
ggaggatttc taccccttcc tcaaggacaa tagggagaaa atcgaaaaga ttctgacctt   2160
caggatcccc tactacgtgg cccctcttgc caggggcaac agccgattcg cttggatgac   2220
aagaaagagc gaggagacca tcacccctg aacttcgag gaagtggtgg acaaaggagc    2280
aagcgcgcag tctttcatcg aacggatgac caatttcgac aaaaacctgc taacgagaa    2340
ggtgctgccc aagcacagcc tgctttacga gtacttcacc gtgtacaacg agctcaccaa   2400
ggtgaaatat gtgaccgagg gcatgcgaaa acccgctttc ctgagcggcg agcagaagaa   2460
ggccatcgtg gacctgctgt tcaagaccaa caggaaggtg accgtgaagc agctgaagga   2520
ggactacttc aagaagatcg agtgctttga tagcgtggaa ataagcggcg tggaggacag   2580
gttcaacgcc agcctgggca cctaccacga cttgttgaag ataatcaaag acaaggattt   2640
cctggataat gaggagaacg aggatatact cgaggacatc gtgctgactt tgacctgtt    2700
tgaggaccga gagatgattg aagaaaggct caaaaccta cgcccacctgt tcgacgacaa   2760
```

```
agtgatgaaa caactgaaga gacgaagata caccggctgg ggcagactgt ccaggaagct    2820
catcaacggc attagggaca agcagagcgg caagaccatc ctggatttcc tgaagtccga    2880
cggcttcgcc aaccgaaact tcatgcagct gattcacgat gacagcttga ccttcaagga    2940
ggacatccag aaggcccagg ttagcggcca gggcgactcc ctgcacgaac atattgcaaa    3000
cctggcaggc tcccctgcga tcaagaaggg catactgcag accgttaagg ttgtggacga    3060
attggtcaag gtcatgggca ggcacaagcc cgaaaacata gttatagaga tggccagaga    3120
gaaccagacc acccaaaagg ccagaagaa cagccgggag cgcatgaaaa ggatcgagga    3180
gggtatcaag gaactcggaa gccagatcct caaagagcac cccgtggaga atacccagct    3240
ccagaacgag aagctgtacc tgtactacct gcagaacggc agggacatgt acgttgacca    3300
ggagttggac atcaacaggc tttcagacta tgacgtggat cacatagtgc cccgagctt    3360 tcttaaagac gatagcatcg acaacaaggt cctgacccgc tccgacaaaa acaggggcaa    3420
aagcgacaac gtgccaagcg aagaggtggt taaaaagatg aagaactact ggaggcaact    3480
gctcaacgcg aaattgatca cccagagaaa gttcgataac ctgaccaagg ccgagagggg    3540
cggactctcc gaacttgaca aagcgggctt cataaagagg cagctggtcg agacccgaca    3600
gatcacgaag cacgtggccc aaatcctcga cagcagaatg aataccaagt acgatgagaa    3660
tgacaaactc atcagggaag tgaaagtgat taccctgaag agcaagttgg tgtccgactt    3720
tcgcaaagat ttccagttct acaaggtgag ggagatcaac aactaccacc atgcccacga    3780
cgcatacctg aacgccgtgg tcggcaccgc cctgattaag aagtatccaa agctggagtc    3840
cgaatttgtc tacggcgact acaaagttta cgatgtgagg aagatgatcg ctaagagcga    3900
acaggagatc ggcaaggcca ccgctaagta tttcttctac agcaacatca tgaactttt    3960 caagaccgag atcacacttg ccaacggcga aatcaggaag aggccgctta tcgagaccaa    4020
cggtgagacc ggcgagatcg tgtgggacaa gggcagggac ttcgccaccg tgaggaaagt    4080
cctgagcatg ccccaggtga atattgtgaa aaaaactgag gtgcagacag gcggctttag    4140
caaggaatcc atcctgccca gaggaacag cgacaagctg atcgcccgga agaaggactg    4200
ggaccctaag aagtatggag gcttcgacag ccccaccgta gcctcagcg tgctggtggt    4260 cgcgaaggta gagaagggga gagcaagaa actgaagagc gtgaaggagc tgctcggcat    4320
aaccatcatg gagaggtcca gctttgagaa gaaccccatt gacttttgg aagccaaggg    4380 ctacaaagag gtcaaaaagg acctgatcat caaactccc aagtactccc tgtttgaatt    4440
ggagaacggc agaaagagga tgctggcgag cgctggggaa ctgcaaaagg caacgaact    4500 ggcgctgccc agcaagtacg tgaattttct gtacctggcg tcccactacg aaaagctgaa    4560
aggcagcccc gaggacaacg agcagaagca gctgttcgtg gagcagcaca gcattacct    4620 ggacgagata tcgagcaaa tcagcgagtt cagcaagagg gtgattctgg ccgacgcgaa    4680
cctggataag gtcctcagcg cctacaacaa gcaccgagac aaaccatca gggagcaggc    4740 cgagaatatc atacacctgt tcaccctgac aaatctgggc gcacctgcgg cattcaaata    4800
cttcgatacc accatcgaca ggaaaaggta cactagcact aaggaggtgc tggatgccac    4860
cttgatccac cagtccatta ccggcctgta tgagaccagg atcgacctga ccagcttgg    4920 aggcgactct agggcggacc caaaaaagaa aaggaaggtg gaattctcta gaggcagtgg    4980
agagggcaga ggaagtctgc taacatgcgg tgacgtcgag gagaatcctg cccaatgaa    5040 cctgagcaaa acgtgagcg tgagcgtgta tatgaagggg aacgtcaaca atcatgagtt    5100
```

```
tgagtacgac ggggaaggtg gtggtgatcc ttatacaggt aaatattcca tgaagatgac    5160
gctacgtggt caaaattccc taccctttc  ctatgatatc attaccacgg catttcagta    5220
tggtttccgc gtatttacaa atacccctga gggaattgtt gactatttta aggactcgct    5280
tcccgacgca ttccagtgga acagacgaat tgtgtttgaa gatggtggag tactaaacat    5340
gagcagtgat atcacatata aagataatgt tctgcatggt gacgtcaagg ctgagggagt    5400
gaacttcccg ccgaatgggc cagtgatgaa gaatgaaatt gtgatggagg aaccgactga    5460
agaaacattt actccaaaaa acggggttct tgttggcttt tgtcccaaag cgtacttact    5520
taaagacggt tcctattact atggaaatat gacaacattt tacagatcca agaaatctgg    5580
ccaggcacct cctgggtatc actttgttaa gcatcgtctc gtcaagacca atgtgggaca    5640
tggatttaag acggttgagc agactgaata tgccactgct catgtcagtg atcttcccaa    5700
gttcgaagct tgataatgag tttaaacggg ggaggctaac tgaaacacgg aaggagacaa    5760
taccggaagg aacccgcgct atgacggcaa taaaaagaca gaataaaacg cacgggtgtt    5820
gggtcgtttg ttcataaacg cggggttcgg tcccagggct ggcactctgt cgataccccα    5880 ccgagacccc attggggcca atacgcccgc gtttcttcct tttccccacc ccacccccca    5940
agttcgggtg aaggcccagg ctcgcagcc  aacgtcgggg cggcaggccc tgccatagca    6000
gatctgcgca gctggggctc taggggtat  ccccacgcgc cctgtagcgg cgcattaagc    6060
gcggcgggtg tggtggttac gcgcagcgtg accgctacac ttgccagcgc cctagcgccc    6120
gctcctttcg ctttcttccc ttcctttctc gccacgttcg ccggctttcc ccgtcaagct    6180
ctaaatcggg ggctcccttt agggttccga tttagtgctt tacggcacct cgaccccaaa    6240
aaacttgatt agggtgatgg ttcacgtagt gggccatcgc cctgatagac ggttttcgc     6300 cctttgacgt tggagtccac gttctttaat agtggactct tgttccaaac tggaacaaca    6360
ctcaacccta tctcggtcta ttcttttgat ttataaggga ttttgccgat ttcggcctat    6420
tggttaaaaa atgagctgat ttaacaaaaa tttaacgcga attaattaag gtcgggcagg    6480
aagagggcct atttcccatg attccttcat atttgcatat acgatacaag gctgttagag    6540
agataattag aattaatttg actgtaaaca caaagatatt agtacaaaat acgtgacgta    6600
gaaagtaata atttcttggg tagtttgcag ttttaaaatt atgttttaaa atggactatc    6660
atatgcttac cgtaacttga agtatttcg  atttcttggc tttatatatc ttgtggaaag    6720
gacgaaacac cgtccattgt ctagcacggc cagttttaga gctagaaata gcaagttaaa    6780
ataaggctag tccgttatca acttgaaaaa gtggcaccga tcggtgcttt ttttctagta    6840
taccgtcgac ctctagctag agcttggcgt aatcatggtc atagctgttt cctgtgtgaa    6900
attgttatcc gctcacaatt ccacacaaca tacgagccgg aagcataaag tgtaaagcct    6960
ggggtgccta atgagtgagc taactcacat taattgcgtt gcgctcactg cccgctttcc    7020
agtcgggaaa cctgtcgtgc cagctgcatt aatgaatcgg ccaacgcgcg gggagaggcg    7080
gtttgcgtat tgggcgctct tccgcttcct cgctcactga ctcgctgcgc tcggtcgttc    7140
ggctgcggcg agcggtatca gctcactcaa aggcggtaat acggttatcc acagaatcag    7200
gggataacgc aggaaagaac atgtgagcaa aaggccagca aaaggccagg aaccgtaaaa    7260
aggccgcgtt gctggcgttt ttccataggc tccgccccc  tgacgagcat cacaaaaatc    7320
gacgctcaag tcagaggtgg cgaaacccga caggactata aagataccag gcgtttcccc    7380
ctggaagctc cctcgtgcgc tctcctgttc cgaccctgcc gcttaccgga tacctgtccg    7440
cctttctccc ttcgggaagc gtggcgcttt ctcatagctc acgctgtagg tatctcagtt    7500
```

```
cggtgtaggt cgttcgctcc aagctgggct gtgtgcacga accccccgtt cagcccgacc    7560
gctgcgcctt atccggtaac tatcgtcttg agtccaaccc ggtaagacac gacttatcgc    7620
cactggcagc agccactggt aacaggatta gcagagcgag gtatgtaggc ggtgctacag    7680
agttcttgaa gtggtggcct aactacggct acactagaag aacagtattt ggtatctgcg    7740
ctctgctgaa gccagttacc ttcggaaaaa gagttggtag ctcttgatcc ggcaaacaaa    7800
ccaccgctgg tagcggtggt ttttttgttt gcaagcagca gattacgcgc agaaaaaaag    7860
gatctcaaga agatcctttg atcttttcta cggggtctga cgctcagtgg aacgaaaact    7920
cacgttaagg gattttggtc atgagattat caaaaaggat cttcacctag atccttttaa    7980
attaaaaatg aagttttaaa tcaatctaaa gtatatatga gtaaacttgg tctgacagtt    8040
accaatgctt aatcagtgag gcacctatct cagcgatctg tctatttcgt tcatccatag    8100
ttgcctgact ccccgtcgtg tagataacta cgatacggga gggcttacca tctggcccca    8160
gtgctgcaat gataccgcga gacccacgct caccggctcc agatttatca gcaataaacc    8220
agccagccgg aagggccgag cgcagaagtg gtcctgcaac tttatccgcc tccatccagt    8280
ctattaattg ttgccgggaa gctagagtaa gtagttcgcc agttaatagt ttgcgcaacg    8340
ttgttgccat tgctacaggc atcgtggtgt cacgctcgtc gtttggtatg gcttcattca    8400
gctccggttc ccaacgatca aggcgagtta catgatcccc catgttgtgc aaaaaagcgg    8460
ttagctcctt cggtcctccg atcgttgtca gaagtaagtt ggccgcagtg ttatcactca    8520
tggttatggc agcactgcat aattctctta ctgtcatgcc atccgtaaga tgcttttctg    8580
tgactggtga gtactcaacc aagtcattct gagaatagtg tatgcggcga ccgagttgct    8640
cttgcccggc gtcaatacgg gataataccg cgccacatag cagaacttta aaagtgctca    8700
tcattggaaa acgttcttcg gggcgaaaac tctcaaggat cttaccgctg ttgagatcca    8760
gttcgatgta acccactcgt gcacccaact gatcttcagc atcttttact ttcaccagcg    8820
tttctgggtg agcaaaaaca ggaaggcaaa atgccgcaaa aaagggaata agggcgacac    8880
ggaaatgttg aatactcata ctcttccttt tcaatattatt ttgaagcatt tatcagggtt    8940
attgtctcat gagcggatac atatttgaat gtatttagaa aaataaacaa ataggggttc    9000
cgcgcacatt tccccgaaaa gtgccacctg acgtcgacgg atcgggagat ctcccgatcc    9060
cctatggtgc actctcagta caatctgctc tgatgccgca tagttaagcc agtatctgct    9120
ccctgcttgt gtgttggagg tcgctgagta gtgcgcgagc aaaatttaag ctacaacaag    9180
gcaaggcttg accgacaatt gcatgaagaa tctgcttagg                          9220

<210> SEQ ID NO 4
<211> LENGTH: 6454
<212> TYPE: DNA
<213> ORGANISM: Artificial Sequence
<220> FEATURE:
<223> OTHER INFORMATION: Synthetic

<400> SEQUENCE: 4
actcttcctt tttcaatatt attgaagcat ttatcagggt tattgtctca tgagcggata     60
catatttgaa tgtatttaga aaataaacaa ataggggttc cgcgcacat ttccccgaaa    120 agtgccacct gaaattgtaag cgttaatatt tgttaaaat tcgcgttaaa ttttttgttaa    180 atcagctcat tttttaacca ataggccgaa atcggcaaaa tcccttataa atcaaaagaa    240
tagaccgaga tagggttgag tgttgttcca gtttggaaca agagtccact attaaagaac    300
```

-continued

```
gtggactcca acgtcaaagg gcgaaaaacc gtctatcagg gcgatggccc actacgtgaa    360
ccatcaccct aatcaagttt tttggggtcg aggtgccgta aagcactaaa tcggaccect    420 aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taacctaga aagataatca tattgtgacg    900
tacgttaaag ataatcatgt gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaac aaaaactcaa   1080
aatttcttct ataaagtaac aaaacttttta tgagggacag ccccccccca aagcccccag   1140
ggatgtaatt acgtccctcc cccgctaggg ggcagcagcg agccgcccgg ggctccgctc   1200
cggtccggcg ctccccccgc atccccgagc cggcagcgtg cggggacagc ccgggcacgg   1260
ggaaggtggc acgggatcgc tttcctctga acgcttctcg ctgctctttg agcctgcaga   1320
cacctggggg gatacgggga aaaggcctcc acggccacta gtattatgcc cagtacatga   1380
ccttatggga ctttcctact ggcagtaca tctacgtatt agtcatcgct attaccatgg   1440
tgatgcggtt ttggcagtac atcaatgggc gtggatagcg gtttgactca cggggatttc   1500
caagtctcca ccccattgac gtcaatggga gtttgttttg gcaccaaaat caacgggact   1560
ttccaaaatg tcgtaacaac tccgccccat tgacgcaaat gggcggtagg cgtgtacggt   1620
gggaggttta tataagcaga gctcgtttag tgaaccgtca gatcgcctgg agacgccatc   1680
cacgctgttt tgacctccat agaagattct agagctagcg aattcgaatt taaatcggat   1740
ccgcggccgc gaaggatctg cgatcgctcc ggtgcccgtc agtgggcaga gcgcacatcg   1800
cccacagtcc ccgagaagtt gggggggaggg gtcggcaatt gaacgggtgc ctagagaagg   1860
tggcgcgggg taaactggga aagtgatgtc gtgtactggc tccgcctttt tcccgagggt   1920
gggggagaac cgtatataag tgcagtagtc gccgtgaacg ttcttttttcg caacgggttt   1980 gccgccagaa cacagctgaa gcttcgaggg gctcgcatct ctccttcacg cgcccgccgc   2040
cctacctgag gccgccatcc acgccggttg agtcgcgttc tgccgcctcc cgcctgtggt   2100
gcctcctgaa ctgcgtccgc cgtctaggta agtttaaagc tcaggtcgag accgggcctt   2160
tgtccggcgc tcccttggag cctacctaga ctcagccggc tctccacgct ttgcctgacc   2220
ctgcttgctc aactctacgt ctttgtttcg ttttctgttc tgcgccgtta cagatccaag   2280
ctgtgaccgg cgcctacgct agatgaccga gtacaagccc acggtgcgcc tcgccacccg   2340
cgacgacgtc cccagggccg tacgcaccct cgccgccgcg ttcgccgact accccgccac   2400
gcgccacacc gtcgatccgg accgccacat cgagcgggtc accgagctgc aagaactctt   2460
cctcacgcgc gtcgggctcg acatcggcaa ggtgtgggtc gcggacgacg cgccgcggt   2520 ggcggtctgg accacgccgg agagcgtcga agcgggggcg gtgttcgccg agatcggccc   2580
gcgcatggcc gagttgagcg gttcccggct ggccgcgcag caacagatgg aaggcctcct   2640
ggcgccgcac cggcccaagg agcccgcgtg gttcctggcc accgtcggcg tctcgcccga   2700
```

```
ccaccagggc aagggtctgg gcagcgccgt cgtgctcccc ggagtggagg cggccgagcg   2760
cgccggggtg cccgccttcc tggagacctc cgcgccccgc aacctcccct tctacgagcg   2820
gctcggcttc accgtcaccg ccgacgtcga ggtgcccgaa ggaccgcgca cctggtgcat   2880
gacccgcaag cccggtgcct gagtcgacaa tcaacctctg gattacaaaa tttgtgaaag   2940
attgactggt attcttaact atgttgctcc ttttacgcta tgtggatacg ctgctttaat   3000
gcctttgtat catgcgttaa ctaaacttgt ttattgcagc ttataatggt tacaaataaa   3060
gcaatagcat cacaaatttc acaaataaag catttttttc actgcattct agttgtggtt   3120
tgtccaaact catcaatgta tcttatcatg tctggaattg actcaaatga tgtcaattag   3180
tctatcagaa gctcatctgg tctcccttcc gggggacaag acatccctgt taatattta   3240
aacagcagtg ttcccaaact gggttcttat atcccttgct ctggtcaacc aggttgcagg   3300
gtttcctgtc ctcacaggaa cgaagtccct aaagaaacag tggcagccag gtttagcccc   3360
ggaattgact ggattccttt tttagggccc attggtatgg cttttccccc gtatcccccc   3420
aggtgtctgc aggctcaaag agcagcgaga agcgttcaga ggaaagcgat cccgtgccac   3480
cttcccgtg cccgggctgt ccccgcacgc tgccggctcg gggatgcggg gggagcgccg   3540
gaccggagcg gagccccggg cggctcgctg ctgcccccta gcggggagg gacgtaatta   3600
catccctggg ggctttgggg gggggctgtc cctgatatct ataacaagaa aatatatata   3660
taataagtta tcacgtaagt agaacatgaa ataacaatat aattatcgta tgagttaaat   3720
cttaaaagtc acgtaaaaga taatcatgcg tcattttgac tcacgcggtc gttatagttc   3780
aaaatcagtg acacttaccg cattgacaag cacgcctcac gggagctcca agcggcgact   3840
gagatgtcct aaatgcacag cgacggattc gcgctattta gaaagagaga gcaatatttc   3900
aagaatgcat gcgtcaattt tacgcagact atctttctag ggttaatcta gctgcatcag   3960
gatcatatcg tcgggtcttt tttccggctc agtcatcgcc caagctggcg ctatctgggc   4020
atcggggagg aagaagcccg tgccttttcc cgcgaggttg aagcggcatg gaaagagttt   4080
gccgaggatg actgctgctg cattgacgtt gagcgaaaac gcacgtttac catgatgatt   4140
cgggaaggtg tggccatgca cgcctttaac ggtgaactgt tcgttcaggc cacctgggat   4200
accagttcgt cgcggctttt ccggacacag ttccggatgg tcagcccgaa gcgcatcagc   4260
aacccgaaca ataccggcga cagccggaac tgccgtgccg tgtgcagat taatgacagc   4320
ggtgcggcgc tgggatatta cgtcagcgag gacgggtatc ctggctggat gccgcagaaa   4380
tggacatgga taccccgtga gttacccggc gggcgcgctt ggcgtaatca tggtcatagc   4440
tgtttcctgt gtgaaattgt tatccgctca caattccaca acatacga gccggaagca   4500
taaagtgtaa agcctgggt gcctaatgag tgagctaact cacattaatt gcgttgcgct   4560
cactgcccgc tttccagtcg ggaaacctgt cgtgccagct gcattaatga atcggccaac   4620
gcgcggggag aggcggtttg cgtattgggc gctcttccgc ttcctcgctc actgactcgc   4680
tgcgctcggt cgttcggctg cggcgagcgg tatcagctca ctcaaaggcg gtaatacggt   4740
tatccacaga atcaggggat aacgcaggaa agaacatgtg agcaaaaggc cagcaaaagg   4800
ccaggaaccg taaaaaggcc gcgttgctgg cgttttccca taggctccgc cccctgacg   4860
agcatcacaa aaatcgacgc tcaagtcaga ggtggcgaaa cccgacagga ctataaagat   4920
accaggcgtt tccccctgga agctccctcg tgcgctctcc tgttccgacc ctgccgctta   4980
ccggatacct gtccgccttt ctcccttcgg gaagcgtggc gctttctcat agctcacgct   5040
```

| | |
|---|---|
| gtaggtatct cagttcggtg taggtcgttc gctccaagct gggctgtgtg cacgaacccc | 5100 |
| ccgttcagcc cgaccgctgc gccttatccg gtaactatcg tcttgagtcc aacccggtaa | 5160 |
| gacacgactt atcgccactg gcagcagcca ctggtaacag gattagcaga gcgaggtatg | 5220 |
| taggcggtgc tacagagttc ttgaagtggt ggcctaacta cggctacact agaaggacag | 5280 |
| tatttggtat ctgcgctctg ctgaagccag ttaccttcgg aaaaagagtt ggtagctctt | 5340 |
| gatccggcaa acaaaccacc gctggtagcg gtggtttttt tgtttgcaag cagcagatta | 5400 |
| cgcgcagaaa aaaggatct caagaagatc ctttgatctt ttctacgggg tctgacgctc | 5460 |
| agtggaacga aaactcacgt taagggattt tggtcatgag attatcaaaa aggatcttca | 5520 |
| cctagatcct tttaaattaa aaatgaagtt ttaaatcaat ctaaagtata tatgagtaaa | 5580 |
| cttggtctga cagttaccaa tgcttaatca gtgaggcacc tatctcagcg atctgtctat | 5640 |
| ttcgttcatc catagttgcc tgactccccg tcgtgtagat aactacgata cgggagggct | 5700 |
| taccatctgg ccccagtgct gcaatgatac cgcgagaccc acgctcaccg gctccagatt | 5760 |
| tatcagcaat aaaccagcca gccggaaggg ccgagcgcag aagtggtcct gcaactttat | 5820 |
| ccgcctccat ccagtctatt aattgttgcc gggaagctag agtaagtagt tcgccagtta | 5880 |
| atagtttgcg caacgttgtt gccattgcta caggcatcgt ggtgtcacgc tcgtcgtttg | 5940 |
| gtatggcttc attcagctcc ggttcccaac gatcaaggcg agttacatga tcccccatgt | 6000 |
| tgtgcaaaaa agcggttagc tccttcggtc tccgatcgt tgtcagaagt aagttggccg | 6060 |
| cagtgttatc actcatggtt atggcagcac tgcataattc tcttactgtc atgccatccg | 6120 |
| taagatgctt ttctgtgact ggtgagtact caaccaagtc attctgagaa tagtgtatgc | 6180 |
| ggcgaccgag ttgctcttgc ccggcgtcaa tacgggataa taccgcgcca catagcagaa | 6240 |
| ctttaaaagt gctcatcatt ggaaaacgtt cttcggggcg aaaactctca aggatcttac | 6300 |
| cgctgttgag atccagttcg atgtaaccca ctcgtgcacc caactgatct tcagcatctt | 6360 |
| ttactttcac cagcgtttct gggtgagcaa aaacaggaag gcaaaatgcc gcaaaaaagg | 6420 |
| gaataagggc gacacggaaa tgttgaatac tcat | 6454 |

<210> SEQ ID NO 5
<211> LENGTH: 4090
<212> TYPE: DNA
<213> ORGANISM: Artificial Sequence
<220> FEATURE:
<223> OTHER INFORMATION: Synthetic

<400> SEQUENCE: 5

| | |
|---|---|
| ggatctgcga tcgctccggt gcccgtcagt gggcagagcg cacatcgccc acagtccccg | 60 |
| agaagttggg ggagggtc ggcaattgaa cgggtgccta gagaaggtgg cgcgggtaa | 120 |
| actgggaaag tgatgtcgtg tactggctcc gcctttttcc cgagggtggg ggagaaccgt | 180 |
| atataagtgc agtagtcgcc gtgaacgttc ttttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggtca tcatgacaac acccagaaat tcagtaaatg ggactttccc | 600 |
| ggcagagcca atgaaaggcc ctattgctat gcaatctggt ccaaaaccac tcttcaggag | 660 |

```
gatgtcttca ctggtgggcc ccacgcaaag cttcttcatg agggaatcta agactttggg    720
ggctgtccag attatgaatg ggctcttcca cattgccctg gggggtcttc tgatgatccc    780
agcagggatc tatgcaccca tctgtgtgac tgtgtggtac cctctctggg gaggcattat    840
gtatattatt tccggatcac tcctggcagc aacggagaaa aactccagga agtgtttggt    900
caaaggaaaa atgataatga attcattgag cctctttgct gccatttctg gaatgattct    960
ttcaatcatg gacatactta atattaaaat ttcccatttt ttaaaaatgg agagtctgaa   1020
ttttattaga gctcacacac catatattaa catatacaac tgtgaaccag ctaatccctc   1080
tgagaaaaac tccccatcta cccaatactg ttacagcata caatctctgt tcttgggcat   1140
tttgtcagtg atgctgatct ttgccttctt ccaggaactt gtaatagctg gcatcgttga   1200
gaatgaatgg aaaagaacgt gctccagacc caaatctaac atagttctcc tgtcagcaga   1260
agaaaaaaaa gaacagacta ttgaaataaa agaagaagtg gttgggctaa ctgaaacatc   1320
ttcccaacca aagaatgaag aagacattga aattattcca atccaagaag aggaagaaga   1380
agaaacagag acgaactttc cagaacctcc ccaagatcag gaatcctcac caatagaaaa   1440
tgacagctct ccttaagtga tttcttctgt ttgctagctg gccagacatg ataagataca   1500
ttgatgagtt tggacaaacc acaactagaa tgcagtgaaa aaaatgcttt atttgtgaaa   1560
tttgtgatgc tattgcttta tttgtaacca ttataagctg caataaacaa gttaacaaca   1620
acaattgcat tcattttatg tttcaggttc agggggaggt gtgggaggtt ttttaaagca   1680
agtaaaacct ctacaaatgt ggtatggaat tctaaaatac agcatagcaa aactttaacc   1740
tccaaatcaa gcctctactt gaatcctttt ctgagggatg aataaggcat aggcatcagg   1800
ggctgttgcc aatgtgcatt agctgtttgc agcctcacct tctttcatgg agtttaagat   1860
atagtgtatt tcccaaggt ttgaactagc tcttcatttc tttatgtttt aaatgcactg   1920
acctcccaca ttccctttt agtaaaatat tcagaaataa tttaaataca tcattgcaat   1980
gaaaataaat gttttttatt aggcagaatc cagatgctca aggcccttca taatatcccc   2040
cagtttagta gttggactta gggaacaaag gaacctttaa tagaaattgg acagcaagaa   2100
agcgagcttc tagctttagt tcctggtgta cttgaggggg atgagttcct caatggtggt   2160
tttgaccagc ttgccattca tctcaatgag cacaaagcag tcaggagcat agtcagagat   2220
gagctctctg cacatgccac aggggctgac cacccctgatg gatctgtcca cctcatcaga   2280
gtaggggtgc ctgacagcca caatggtgtc aaagtccttc tgcccgttgc tcacagcaga   2340
cccaatggca atggcttcag cacagacagt gaccctgcca atgtaggcct caatgtggac   2400
agcagagatg atctccccag tcttggtcct gatggccgcc ccgacatggt gcttgttgtc   2460
ctcatagagc atggtgatct tctcagtggc gacctccacc agctccagat cctgctgaga   2520
gatgttgaag gtcttcatga tggccctcct atagtgagtc gtattatact atgccgatat   2580
actatgccga tgattaattg tcaaaacagc gtggatggcg tctccagctt atctgacggt   2640
tcactaaacg agctctgctt atatagacct cccaccgtac acgcctaccg cccatttgcg   2700
tcaatggggc ggagttgtta cgacattttg gaaagtcccg ttgatttact agtcaaaaca   2760
aactcccatt gacgtcaatg gggtggagac ttggaaatcc ccgtgagtca aaccgctatc   2820
cacgcccatt gatgtactgc caaaaccgca tcatcatggt aatagcgatg actaatacgt   2880
agatgtactg ccaagtagga aagtcccata aggtcatgta ctgggcataa tgccaggcgg   2940
gccatttacc gtcattgacg tcaatagggg gcgtacttgg catatgatac acttgatgta   3000
```

```
ctgccaagtg ggcagtttac cgtaaatact ccacccattg acgtcaatgg aaagtcccta    3060
ttggcgttac tatgggaaca tacgtcatta ttgacgtcaa tgggcggggg tcgttgggcg    3120
gtcagccagg cgggccattt accgtaagtt atgtaacgcc tgcaggttaa ttaagaacat    3180
gtgagcaaaa ggccagcaaa aggccaggaa ccgtaaaaag gccgcgttgc tggcgttttt    3240
ccataggctc cgcccccctg acgagcatca aaaaatcga cgctcaagtc agaggtggcg    3300
aaacccgaca ggactataaa gataccaggc gtttccccct ggaagctccc tcgtgcgctc    3360
tcctgttccg accctgccgc ttaccggata cctgtccgcc tttctccctt cgggaagcgt    3420
ggcgctttct catagctcac gctgtaggta tctcagttcg gtgtaggtcg ttcgctccaa    3480
gctgggctgt gtgcacgaac cccccgttca gcccgaccgc tgcgccttat ccggtaacta    3540
tcgtcttgag tccaacccgg taagacacga cttatcgcca ctggcagcag ccactggtaa    3600
caggattagc agagcgaggt atgtaggcgg tgctacagag ttcttgaagt ggtggcctaa    3660
ctacggctac actagaagaa cagtatttgg tatctgcgct ctgctgaagc cagttacctt    3720
cggaaaaaga gttggtagct cttgatccgg caaacaaacc accgctggta gcggtggttt    3780
ttttgtttgc aagcagcaga ttacgcgcag aaaaaaagga tctcaagaag atcctttgat    3840
cttttctacg gggtctgacg ctcagtggaa cgaaaactca cgttaaggga ttttggtcat    3900
ggctagttaa ttaacattta atcagcggc  cgcaataaaa tatctttatt ttcattacat    3960
ctgtgtgttg gttttttgtg tgaatcgtaa ctaacatacg ctctccatca aaacaaaacg    4020
aaacaaaaca aactagcaaa ataggctgtc cccagtgcaa gtgcaggtgc cagaacattt    4080
ctctatcgaa                                                           4090

<210> SEQ ID NO 6
<211> LENGTH: 6872
<212> TYPE: DNA
<213> ORGANISM: Artificial Sequence
<220> FEATURE:
<223> OTHER INFORMATION: Synthetic

<400> SEQUENCE: 6
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc  cgagggtggg ggagaaccgt     180
atataagtgc agtagtcgcc gtgaacgttc tttttcgcaa cgggtttgcc gccagaacac     240
agctgaagct tcgagggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggtca gcatgcgacc ctccgggacg gccggggcag cgctcctggc     600
gctgctggct gcgctctgcc cggcgagtcg ggctctggag gaaaagaaag tttgccaagg     660
cacgagtaac aagctcacgc agttgggcac ttttgaagat catttttctca gcctccagag     720
gatgttcaat aactgtgagg tggtccttgg gaatttggaa attacctatg tgcagaggaa     780
ttatgaccctt tccttcttaa agaccatcca ggaggtggct ggttatgtcc tcattgccct     840
caacacagtg gagcgaattc ctttggaaaa cctgcagatc atcagaggaa atatgtacta     900
cgaaaattcc tatgccttag cagtcttatc taactatgat gcaaataaaa ccggactgaa     960
```

```
ggagctgccc atgagaaatt tacaggaaat cctgcatggc gccgtgcggt tcagcaacaa    1020
ccctgccctg tgcaacgtgg agagcatcca gtggcgggac atagtcagca gtgactttct    1080
cagcaacatg tcgatggact tccagaacca cctgggcagc tgccaaaagt gtgatccaag    1140
ctgtcccaat gggagctgct ggggtgcagg agaggagaac tgccagaaac tgaccaaaat    1200
catctgtgcc cagcagtgct ccgggcgctg ccgtggcaag tcccccagtg actgctgcca    1260
caaccagtgt gctgcaggct gcacaggccc cggggagagc gactgcctgg tctgccgcaa    1320
attccgagac gaagccacgt gcaaggacac ctgccccccca ctcatgctct acaaccccac    1380
cacgtaccag atggatgtga accccgaggg caaatacagc tttggtgcca cctgcgtgaa    1440
gaagtgtccc cgtaattatg tggtgacaga tcacggctcg tgcgtccgag cctgtggggc    1500
cgacagctat gagatggagg aagacggcgt ccgcaagtgt aagaagtgcg aagggccttg    1560
ccgcaaagtg tgtaacggaa taggtattgg tgaatttaaa gactcactct ccataaatgc    1620
tacgaatatt aaacacttca aaaactgcac ctccatcagt ggcgatctcc acatcctgcc    1680
ggtggcattt aggggtgact ccttcacaca tactcctcct ctggatccac aggaactgga    1740
tattctgaaa accgtaaagg aaatcacagg gttttttgctg attcaggctt ggcctgaaaa    1800
caggacggac ctccatgcct ttgagaacct agaaaatcata cgcggcagga ccaagcaaca    1860
tggtcagttt tctcttgcag tcgtcagcct gaacataaca tccttgggat tacgctccct    1920
caaggagata agtgatggag atgtgataat ttcaggaaac aaaaaatttgt gctatgcaaa    1980 tacaataaac tggaaaaaac tgtttgggac ctccggtcag aaaaccaaaa ttataagcaa    2040
cagaggtgaa aacagctgca aggccacagg ccaggtctgc catgccttgt gctcccccga    2100
gggctgctgg ggcccggagc ccagggactg cgtctcttgc cggaatgtca gccgaggcag    2160
ggaatgcgtg gacaagtgca accttctgga gggtgagcca agggagtttg tggaaaactc    2220
tgagtgcata cagtgccacc cagagtgcct gcctcaggcc atgaacatca cctgcacagg    2280
acggggacca gacaactgta tccagtgtgc ccactacatt gacggccccc actgcgtcaa    2340
gacctgcccg gcaggagtca tgggagaaaa caacacccctg gtctggaagt acgcagacgc    2400
cggccatgtg tgccacctgt gccatccaaa ctgcacctac ggatgcactg gccaggtct    2460 tgaaggctgt ccaacgaatg ggcctaagat cccatccatc gccactggga tggtgggggc    2520
cctcctcttg ctgctggtgg tggccctggg gatcggcctc ttcatgcgaa ggcgccacat    2580
cgttcggaag cgcacgctgc ggaggctgct gcaggagagg gagcttgtgg agcctcttac    2640
acccagtgga gaagctccca accaagctct cttgaggatc ttgaaggaaa ctgaattcaa    2700
aaagatcaaa gtgctgggct ccggtgcgtt cggcacggtg tataagggac tctggatccc    2760
agaaggtgag aaagttaaaa ttcccgtcgc tatcaaggaa ttaagagaag caacatctcc    2820
gaaagccaac aaggaaatcc tcgatgaagc ctacgtgatg gccagcgtgg acaaccccca    2880
cgtgtgccgc ctgctgggca tctgcctcac ctccaccgtg cagctcatca cgcagctcat    2940
gcccttcggc tgcctcctgg actatgtccg ggaacacaaa gacaatattg ctcccagta    3000 cctgctcaac tggtgtgtgc agatcgcaaa gggcatgaac tacttggagg accgtcgctt    3060
ggtgcaccgc gacctggcag ccaggaacgt actggtgaaa acaccgcagc atgtcaagat    3120
cacagatttt gggctggcca aactgctggg tgcggaagag aaagaatacc atgcagaagg    3180
aggcaaagtg cctatcaagt ggatggcatt ggaatcaatt ttacacagaa tctatacccca    3240 ccagagtgat gtctggagct acggggtgac cgtttgggag ttgatgacct ttggatccaa    3300
```

```
gccatatgac ggaatccctg ccagcgagat ctcctccatc ctggagaaag gagaacgcct    3360
ccctcagcca cccatatgta ccatcgatgt ctacatgatc atggtcaagt gctggatgat    3420
agacgcagat agtcgcccaa agttccgtga gttgatcatc gaattctcca aaatggcccg    3480 agaccccag cgctaccttg tcattcaggg ggatgaaaga atgcatttgc caagtcctac    3540
agactccaac ttctaccgtg ccctgatgga tgaagaagac atggacgacg tggtggatgc    3600
cgacgagtac ctcatcccac agcagggctt cttcagcagc cctccacgt cacggactcc    3660 cctcctgagc tctctgagtg caaccagcaa caattccacc gtggcttgca ttgatagaaa    3720
tgggctgcaa agctgtccca tcaaggaaga cagcttcttg cagcgataca gctcagaccc    3780
cacaggcgcc ttgactgagg acagcataga cgacccttc ctcccagtgc ctgaatacat    3840
aaaccagtcc gttcccaaaa ggcctgctgg ctctgtgcag aatcctgtct atcacaatca    3900
gcctctgaac cccgcgccca gcagagaccc acactaccag gacccccaca gcactgcagt    3960
gggcaacccc gagtatctca acactgtcca gcccacctgt gtcaacagca cattcgacag    4020
ccctgcccac tgggcccaga aaggcagcca ccaaattagc ctggacaacc ctgactacca    4080
gcaggacttc tttcccaagg aagccaagcc aaatggcatc tttaagggct ccacagctga    4140
aaatgcagaa tacctaaggg tcgcgccaca aagcagtgaa tttattggag catgaccacg    4200
gaggatagta tgagccctaa aaatccagac tctttcgata cccaggacca agccgctagc    4260
tggccagaca tgataagata cattgatgag tttggacaaa ccacaactag aatgcagtga    4320
aaaaaatgct ttatttgtga aatttgtgat gctattgctt tatttgtaac cattataagc    4380
tgcaataaac aagttaacaa caacaattgc attcatttta tgtttcaggt tcaggggag    4440 gtgtgggagg tttttaaag caagtaaaac ctctacaaat gtggtatgga attctaaaat    4500
acagcatagc aaaactttaa cctccaaatc aagcctctac ttgaatcctt ttctgaggga    4560
tgaataaggc ataggcatca ggggctgttg ccaatgtgca ttagctgttt gcagcctcac    4620
cttctttcat ggagtttaag atatagtgta ttttcccaag gtttgaacta gctcttcatt    4680
tctttatgtt ttaaatgcac tgacctccca cattccctt ttagtaaaat attcagaaat    4740
aatttaaata catcattgca atgaaaataa atgtttttta ttaggcagaa tccagatgct    4800
caaggccctt cataatatcc cccagtttag tagttggact tagggaacaa aggaaccttt    4860
aatagaaatt ggacagcaag aaagcgagct tctagcttta gttcctggtg tacttgaggg    4920
ggatgagttc ctcaatggtg gttttgacca gcttgccatt catctcaatg agcacaaagc    4980
agtcaggagc atagtcagag atgagctctc tgcacatgcc acaggggctg accaccctga    5040
tggatctgtc cacctcatca gagtaggggt gcctgacagc acaatggtg tcaaagtcct    5100 tctgcccgtt gctcacagca gacccaatgg caatggcttc agcacagaca gtgaccctgc    5160
caatgtaggc ctcaatgtgg acagcagaga tgatctcccc agtcttggtc ctgatggccg    5220
ccccgacatg gtgcttgttg tcctcataga gcatggtgat cttctcagtg gcgacctcca    5280
ccagctccag atcctgctga gagatgttga aggtcttcat gatggccctc ctatagtgag    5340
tcgtattata ctatgccgat atactatgcc gatgattaat tgtcaaaaca gcgtggatgg    5400
cgtctccagc ttatcgacg gttcactaaa cgagctctgc ttatatagac ctcccaccgt    5460
acacgcctac cgcccatttg cgtcaatggg gcggagttgt tacgacattt tggaaagtcc    5520
cgttgattta ctagtcaaaa caaactccca ttgacgtcaa tggggtggag acttggaaat    5580
ccccgtgagt caaaccgcta tccacgccca ttgatgtact gccaaaaccg catcatcatg    5640
gtaatagcga tgactaatac gtagatgtac tgccaagtag gaaagtccca taaggtcatg    5700
```

```
tactgggcat aatgccaggc gggccattta ccgtcattga cgtcaatagg gggcgtactt    5760
ggcatatgat acacttgatg tactgccaag tgggcagttt accgtaaata ctccacccat    5820
tgacgtcaat ggaaagtccc tattggcgtt actatgggaa catacgtcat tattgacgtc    5880
aatgggcggg ggtcgttggg cggtcagcca ggcgggccat ttaccgtaag ttatgtaacg    5940
cctgcaggtt aattaagaac atgtgagcaa aaggccagca aaaggccagg aaccgtaaaa    6000
aggccgcgtt gctggcgttt ttccataggc tccgcccccc tgacgagcat cacaaaaatc    6060
gacgctcaag tcagaggtgg cgaaacccga caggactata agataccag gcgtttcccc    6120 ctggaagctc cctcgtgcgc tctcctgttc cgaccctgcc gcttaccgga tacctgtccg    6180
cctttctccc ttcgggaagc gtggcgcttt ctcatagctc acgctgtagg tatctcagtt    6240
cggtgtaggt cgttcgctcc aagctgggct gtgtgcacga accccccgtt cagcccgacc    6300
gctgcgcctt atccggtaac tatcgtcttg agtccaaccc ggtaagacac gacttatcgc    6360
cactggcagc agccactggt aacaggatta gcagagcgag gtatgtaggc ggtgctacag    6420
agttcttgaa gtggtggcct aactacggct acactagaag aacagtattt ggtatctgcg    6480
ctctgctgaa gccagttacc ttcggaaaaa gagttggtag ctcttgatcc ggcaaacaaa    6540
ccaccgctgg tagcggtggt ttttttgttt gcaagcagca gattacgcgc agaaaaaaag    6600
gatctcaaga agatcctttg atcttttcta cggggtctga cgctcagtgg aacgaaaact    6660
cacgttaagg gattttggtc atggctagtt aattaacatt taaatcagcg gccgcaataa    6720
aatatcttta ttttcattac atctgtgtgt tggttttttg tgtgaatcgt aactaacata    6780
cgctctccat caaaacaaaa cgaaacaaaa caaactagca aaataggctg tccccagtgc    6840
aagtgcaggt gccagaacat ttctctatcg aa                                  6872

<210> SEQ ID NO 7
<211> LENGTH: 6965
<212> TYPE: DNA
<213> ORGANISM: Artificial Sequence
<220> FEATURE:
<223> OTHER INFORMATION: Synthetic

<400> SEQUENCE: 7
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgagggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggtca ccatggagct ggcggccttg tgccgctggg ggctcctcct     600
cgccctcttg ccccccggag ccgcgagcac ccaagtgtgc accggcacag acatgaagct     660
gcggctccct gccagtcccg agacccacct ggacatgctc cgccacctct accagggctg     720
ccaggtggtg cagggaaacc tggaactcac ctacctgccc accaatgcca gcctgtcctt     780
cctgcaggat atccaggagg tgcagggcta cgtgctcatc gctcacaacc aagtgaggca     840
```

-continued

```
ggtcccactg cagaggctgc ggattgtgcg aggcacccag ctctttgagg acaactatgc    900
cctggccgtg ctagacaatg agacccgct gaacaatacc accctgtca caggggcctc    960 cccaggaggc ctgcgggagc tgcagcttcg aagcctcaca gagatcttga aaggaggggt   1020
cttgatccag cggaaccccc agctctgcta ccaggacacg attttgtgga aggacatctt   1080
ccacaagaac aaccagctgg ctctcacact gatagacacc aaccgctctc gggcctgcca   1140
cccctgttct ccgatgtgta agggctcccg ctgctgggga gagagttctg aggattgtca   1200
gagcctgacg cgcactgtct gtgccggtgg ctgtgcccgc tgcaaggggc cactgcccac   1260
tgactgctgc catgagcagt gtgctgccgg ctgcacgggc cccaagcact ctgactgcct   1320
ggcctgcctc cacttcaacc acagtggcat ctgtgagctg cactgcccag ccctggtcac   1380
ctacaacaca gacacgtttg agtccatgcc caatcccgag gccggtata cattcggcgc   1440 cagctgtgtg actgcctgtc cctacaacta cctttctacg acgtgggat cctgcaccct   1500 cgtctgcccc ctgcacaacc aagaggtgac agcagaggat ggaacacagc ggtgtgagaa   1560
gtgcagcaag ccctgtgccc gagtgtgcta tggtctgggg atggagcact gcgagaggt   1620 gagggcagtt accagtgcca atatccagga gtttgctggc tgcaagaaga tctttgggag   1680
cctggcattt ctgccggaga gctttgatgg ggacccagcc tccaacactg ccccgctcca   1740
gccagagcag ctccaagtgt ttgagactct ggaagagatc acaggttacc tatacatctc   1800
agcatggccg acagcctgc ctgacctcag cgtcttccag aacctgcaag taatccgggg   1860
acgaattctg cacaatggcg cctactcgct gaccctgcaa gggctgggca tcagctggct   1920
ggggctgcgc tcactgaggg aactgggcag tggactggcc ctcatccacc ataacaccca   1980
cctctgcttc gtgcacacgg tgccctggga ccagctcttt cggaacccgc accaagctct   2040
gctccacact gccaaccggc cagaggacga gtgtgtgggc gagggcctgg cctgccacca   2100
gctgtgcgcc cgagggcact gctggggtcc agggcccacc cagtgtgtca actgcagcca   2160
gttccttcgg ggccaggagt gcgtggagga atgccgagta ctgcagggc tccccaggga   2220 gtatgtgaat gccaggcact gttttgccgtg ccaccctgag tgtcagcccc agaatggctc   2280
agtgacctgt tttggaccgg aggctgacca gtgtgtggcc tgtgcccact ataaggaccc   2340 tccccttctgc gtggcccgct gccccagcgg tgtgaaacct gacctctcct acatgcccat   2400
ctggaagttt ccagatgagg agggcgcatg ccagccttgc cccatcaact gcacccactc   2460
ctgtgtggac ctggatgaca agggctgccc cgccgagcag agagccagcc tctgacgtc   2520 catcgtctct gcggtggttg gcattctgct ggtcgtggtc ttgggggtgg tcttgggat   2580 cctcatcaag cgacggcagc agaagatccg gaagtacacg atgcgagac tgctgcagga   2640 aacggagctg gtggagccgc tgacacctag cggagcgatg cccaaccagg cgcagatgcg   2700
gatcctgaaa gagacggagc tgaggaaggt gaaggtgctt ggatctggcg cttttggcac   2760
agtctacaag gcatctgga tccctgatgg ggagaatgtg aaaattccag tggccatcaa   2820
agtgttgagg gaaaacacat cccccaaagc caacaaagaa atcttagacg aagcatacgt   2880
gatggctggt gtgggctccc catatgtctc ccgccttctg ggcatctgcc tgacatccac   2940
ggtgcagctg gtgacacagc ttatgccta tggctgcctc ttagaccatg tccgggaaaa   3000
ccgcggacgc ctgggctccc aggacctgct gaactggtgt atgcagattg ccaaggggat   3060
gagctacctg gaggatgtgc ggctcgtaca cagggacttg gccgctcgga acgtgctggt   3120
caagagtccc aaccatgtca aaattacaga cttcggctg gctcggctgc tggacattga   3180
cgagacagag taccatgcag atgggggcaa ggtgcccatc aagtggatgg cgctggagtc   3240
```

```
cattctccgc cggcggttca cccaccagag tgatgtgtgg agttatggtg tgactgtgtg    3300
ggagctgatg acttttgggg ccaaaccttä cgatgggatc ccagcccggg agatccctga    3360
cctgctggaa aagggggagc ggctgcccca gcccccatc tgcaccattg atgtctacat     3420
gatcatggtc aaatgttgga tgattgactc tgaatgtcgg ccaagattcc gggagttggt    3480
gtctgaattc tcccgcatgg ccagggaccc ccagcgcttt gtggtcatcc agaatgagga    3540
cttgggccca gccagtccct tggacagcac cttctaccgc tcactgctgg aggacgatga    3600 catggggggac ctggtggatg ctgaggagta tctggtaccc cagcagggct tcttctgtcc    3660
agaccctgcc ccgggcgctg ggggcatggt ccaccacagg caccgcagct catctaccag    3720
gagtggcggt ggggacctga cactagggct ggagccctct gaagaggagg cccccaggtc    3780
tccactggca ccctccgaag gggctggctc cgatgtattt gatggtgacc tgggaatggg    3840
ggcagccaag gggctgcaaa gcctccccac acatgacccc agccctctac agcggtacag    3900
tgaggacccc acagtacccc tgccctctga gactgatggc tacgttgccc ccctgacctg    3960
cagcccccag cctgaatatg tgaaccagcc agatgttcgg cccccagcccc cttcgccccg    4020 agagggcccct ctgcctgctg cccgacctgc tggtgccact ctggaaaggc ccaagactct    4080
ctccccaggg aagaatgggg tcgtcaaaga cgttttttgcc tttgggggtg ccgtggagaa    4140
ccccgagtac ttgacacccc agggaggagc tgccctcag ccccaccctc ctcctgcctt      4200
cagcccagcc ttcgacaacc tctattactg ggaccaggac ccaccagagc gggggggctcc    4260 acccagcacc ttcaaaggga cacctacggc agagaaccca gagtacctgg gtctggacgt    4320
gccagtgtga accagaaggc caagtccgct agctggccag acatgataag atacattgat    4380
gagtttggac aaaccacaac tagaatgcag tgaaaaaaat gctttatttg tgaaatttgt    4440
gatgctattg ctttatttgt aaccattata agctgcaata aacaagttaa caacaacaat    4500
tgcattcatt ttatgtttca ggttcagggg gaggtgtggg aggttttta aagcaagtaa    4560 aacctctaca aatgtggtat ggaattctaa aatacagcat agcaaaactt taacctccaa    4620
atcaagcctc tacttgaatc cttttctgag ggatgaataa ggcataggca tcaggggctg    4680
ttgccaatgt gcattagctg tttgcagcct caccttcttt catggagttt aagatatagt    4740
gtattttccc aaggttttgaa ctagctcttc atttctttat gttttaaatg cactgacctc    4800
ccacattccc tttttagtaa aatattcaga ataatttaa atacatcatt gcaatgaaaa    4860
taaatgtttt ttattaggca gaatccagat gctcaaggcc cttcataata tcccccagtt    4920
tagtagttgg acttagggaa caaaggaacc tttaatagaa attggacagc aagaaagcga    4980
gcttctagct ttagttcctg gtgtacttga ggggatgag ttcctcaatg gtggttttga    5040
ccagcttgcc attcatctca atgagcacaa agcagtcagg agcatagtca gagatgagct    5100
ctctgcacat gccacagggg ctgaccaccc tgatggatct gtccacctca tcagagtagg    5160
ggtgcctgac agccacaatg gtgtcaaagt ccttctgccc gttgctcaca gcagacccaa    5220
tggcaatggc ttcagcacag acagtgaccc tgccaatgta ggcctcaatg tggacagcag    5280
agatgatctc cccagtcttg gtcctgatgg ccgccccgac atggtgcttg ttgtcctcat    5340
agagcatggt gatcttctca gtggcgacct ccaccagctc cagatcctgc tgagagatgt    5400
tgaaggtctt catggtggcc ctcctatagt gagtcgtatt atactatgcc gatatactat    5460
gccgatgatt aattgtcaaa acagcgtgga tggcgtctcc agcttatctg acggttcact    5520
aaacgagctc tgcttatata gacctcccac cgtacacgcc taccgcccat ttgcgtcaat    5580
```

```
ggggcggagt tgttacgaca ttttggaaag tcccgttgat ttactagtca aaacaaactc    5640
ccattgacgt caatggggtg gagacttgga atccccgtg agtcaaaccg ctatccacgc     5700
ccattgatgt actgccaaaa ccgcatcatc atggtaatag cgatgactaa tacgtagatg    5760
tactgccaag taggaaagtc ccataaggtc atgtactggg cataatgcca ggcgggccat    5820
ttaccgtcat tgacgtcaat aggggcgta cttggcatat gatacacttg atgtactgcc    5880
aagtgggcag tttaccgtaa atactccacc cattgacgtc aatggaaagt ccctattggc    5940
gttactatgg gaacatacgt cattattgac gtcaatgggc ggggtcgtt gggcggtcag     6000 ccaggcgggc catttaccgt aagttatgta acgcctgcag gttaattaag aacatgtgag    6060
caaaaggcca gcaaaaggcc aggaaccgta aaaaggccgc gttgctggcg ttttttccata   6120 ggctccgccc ccctgacgag catcacaaaa atcgacgctc aagtcagagg tggcgaaacc    6180
cgacaggact ataaagatac caggcgtttc ccctggaag ctccctcgtg cgctctcctg     6240
ttccgaccct gccgcttacc ggatacctgt ccgcctttct cccttcggga agcgtggcgc    6300
tttctcatag ctcacgctgt aggtatctca gttcggtgta ggtcgttcgc tccaagctgg    6360
gctgtgtgca cgaaccccc gttcagcccg accgctgcgc cttatccggt aactatcgtc      6420
ttgagtccaa cccggtaaga cacgacttat cgccactggc agcagccact ggtaacagga    6480
ttagcagagc gaggtatgta ggcggtgcta cagagttctt gaagtggtgg cctaactacg    6540
gctacactag aagaacagta tttggtatct gcgctctgct gaagccagtt accttcggaa    6600
aaagagttgg tagctcttga tccggcaaac aaaccaccgc tggtagcggt ggtttttttg    6660
tttgcaagca gcagattacg cgcagaaaaa aaggatctca agaagatcct ttgatctttt    6720
ctacggggtc tgacgctcag tggaacgaaa actcacgtta agggattttg gtcatggcta    6780
gttaattaac atttaaatca gcggccgcaa taaaatatct ttattttcat tacatctgtg    6840
tgttggtttt ttgtgtgaat cgtaactaac atacgctctc catcaaaaca aaacgaaaca    6900
aaacaaacta gcaaaatagg ctgtccccag tgcaagtgca ggtgccagaa catttctcta    6960
tcgaa                                                                6965

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8 atataccct cagggttat                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
caccgtgtgt gactcctgtg                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic
```

<400> SEQUENCE: 10
tcatcgctca caaccaagtg                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ggccctattg ctatgcaatc                                                   20

<210> SEQ ID NO 12
<211> LENGTH: 233
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (76)..(76)
<223> OTHER INFORMATION: X can be A or L
<220> FEATURE:
<221> NAME/KEY: misc_feature
<222> LOCATION: (77)..(77)
<223> OTHER INFORMATION: X can be V or L

<400> SEQUENCE: 12

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Xaa Xaa Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

```
Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

SYSTEM AND PRODUCTS FOR IMPROVED QUANTIFICATION OF ADCC ACTIVITY

The Sequence Listing in ASCII text file format of 60,185 bytes in size, created on Jun. 20, 2019, with the file name "2019-06-20SequenceListing_TOVEY17," filed in the U.S. Patent and Trademark Office on even date herewith, is hereby incorporated herein by reference.

FIELD OF THE INVENTION

Present invention relates novel cells and their use in methods for determining the antibody-dependent cell-mediated cytotoxicity (ADCC) in a sample. The cells according to the invention may be used in kit or a kit of parts that may be used in a diagnostic context. Importantly, the cells according to the invention may be used to determine the effectiveness of a treatment based on e.g. antibodies.

BACKGROUND OF THE INVENTION

It is well known that the activity of a number of monoclonal antibodies is mediated in part by antibody-dependent cell-mediated cytotoxicity (ADCC). The antibodies are directed to a specific antigen on a target cell, such as a tumor cell or an inflammation causing lymphocyte. Once bound to the target cell, the Fc receptor moiety of an effector cell will bind to the Fc portion of the monoclonal antibody and thereby effect killing of the target cell by the effector cell.

In order to quantitate the effectiveness of an antibody in such an ADCC process, it is necessary to have effector cells, target cells, and control target cells that are used to determine the effectiveness of the antibody. In the prior art, one harvests endogenous effector cells, natural killer (NK), cells and target cells from human subjects and use those in such testing. In the classic assay, the target cells are chromium loaded so that cell killing can be determined by release of the chromium. This method suffers many disadvantages, such as, one must harvest the target cells used from human subjects and thus there is great variability in the cells being used for the quantification. Furthermore, it is difficult and expensive to obtain the cells in this manner. For example, there is substantial variation from donor to donor. Furthermore, for a negative control in this classical assay, one would use a cell line that does not express the target receptor, such as CD20 for rituximab and erbB2 for trastuzumab. Thus, for example, one would use a T cell line which does not express CD20. The disadvantage of the use of such a negative control target cell is, of course, that the cell is not remotely similar to the target cell and does not constitute a good control.

Another disadvantage is that they are long and protracted assays and often have to be incubated overnight. The dynamic range is restricted and the sensitivity is poor. The dynamic range is the difference between the maximum achievable signal at the highest concentration of the drug and by the control and zero (no drug sample). Sensitivity is the activity generated by small quantities of antibody, i.e., the smaller the quantity of antibody necessary to generate detectable activity, the greater the sensitivity of the assay. Another disadvantage is that the assays are often imprecise rendering the detection of small differences between different variants of a monoclonal antibody difficult. Another disadvantage is that the assays exhibit a low degree of tolerance to the presence of serum, particularly human serum that contains approximately 70 mg/ml of IgG for an adult. Indeed, in specifications for prior art assays it I usually recommend that the ADCC assay is performed in the presence of IgG depleted fetal bovine serum (FBS) even though bovine IgG binds minimally to the human FcγIIIa receptor (1).

One improvement on this standard quantification assay has been described by Parekh at al (2) and modified and commercialized (3). In the assay, it is developed a recombinant effector cell line containing a NFAT responsive reporter gene construct that responds to binding of the Fc moiety of immunoglobunins to the FcγIIIa receptor (CD16) by activation of the firefly luciferase (FL) reporter gene and the emission of light that can be quantified in a luminomter. These effector cells are sold in a freeze, thaw and use format (3). It is an improvement over the standard lytic assay as it uses a surrogate marker of the ADCC mechanism that can be quantified in a much more sensitive manner with somewhat greater dynamic range in a much more convenient format, as one does not have to harvest the effector cells but one uses the freeze and thaw cells.

Nevertheless, there is always a desire to further improve the quantitative ADCC assay. It would be desirable to have an assay which has a much improved dynamic range, improved sensitivity, improved serum tolerance that would allow the quantification of ADCC activity in the presence of human serum, and an improved ease of use.

FIGURES

FIG. 1 illustrates the synthetic chimeric promoter sequence used to regulate expression of the FL reporter gene (SEQ ID NO:1).

FIG. 4 illustrates the CD20 Guide RNA Sequence (SEQ ID NO:11).

Figure 5A:
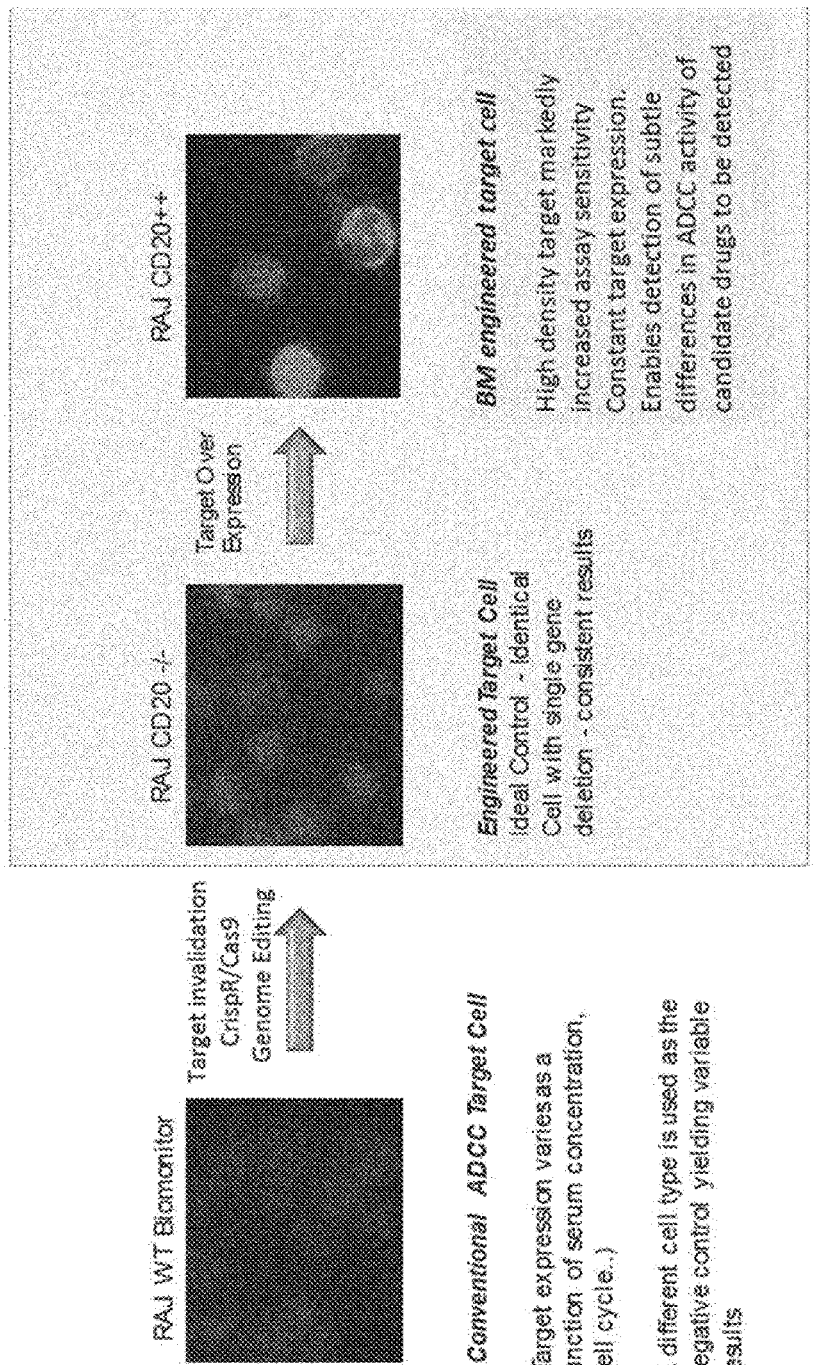
FIG. 5A illustrates the expression of CD20 on the Cell Surface of Wild Type Raji Cells, Raji−/− and Raji++/++ Cells, wherein Cell surface expression of CD20 was visualized using an inverted fluorescent microscope (Evos, Life Technologies Inc.) and a FITC labelled anti-CD20 monoclonal antibody (FAB4225F, R & D Systems).
Figure 5B:
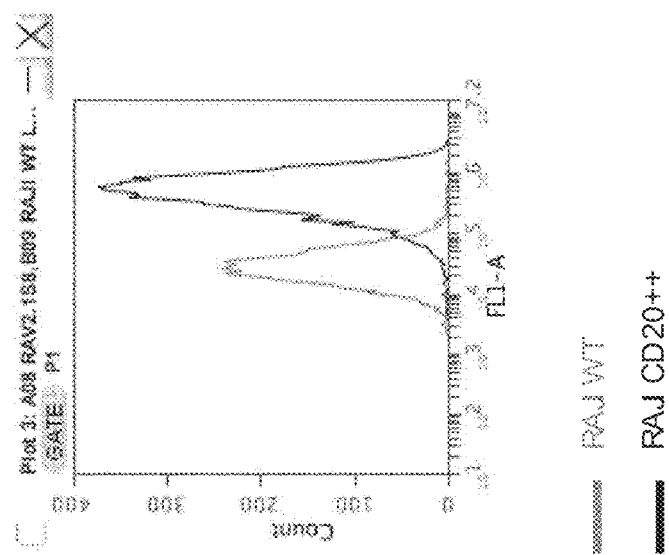
FIG. 5B illustrates the quantification of CD20 Expression on wild type Raji & CD20++ Raji cells using Flow Cytometry, wherein Cell surface expression of CD20 was quantified using flow cytometry and a FITC labelled anti-CD20 monoclonal antibody (FAB4225F, R & D systems).
Figure 5C:
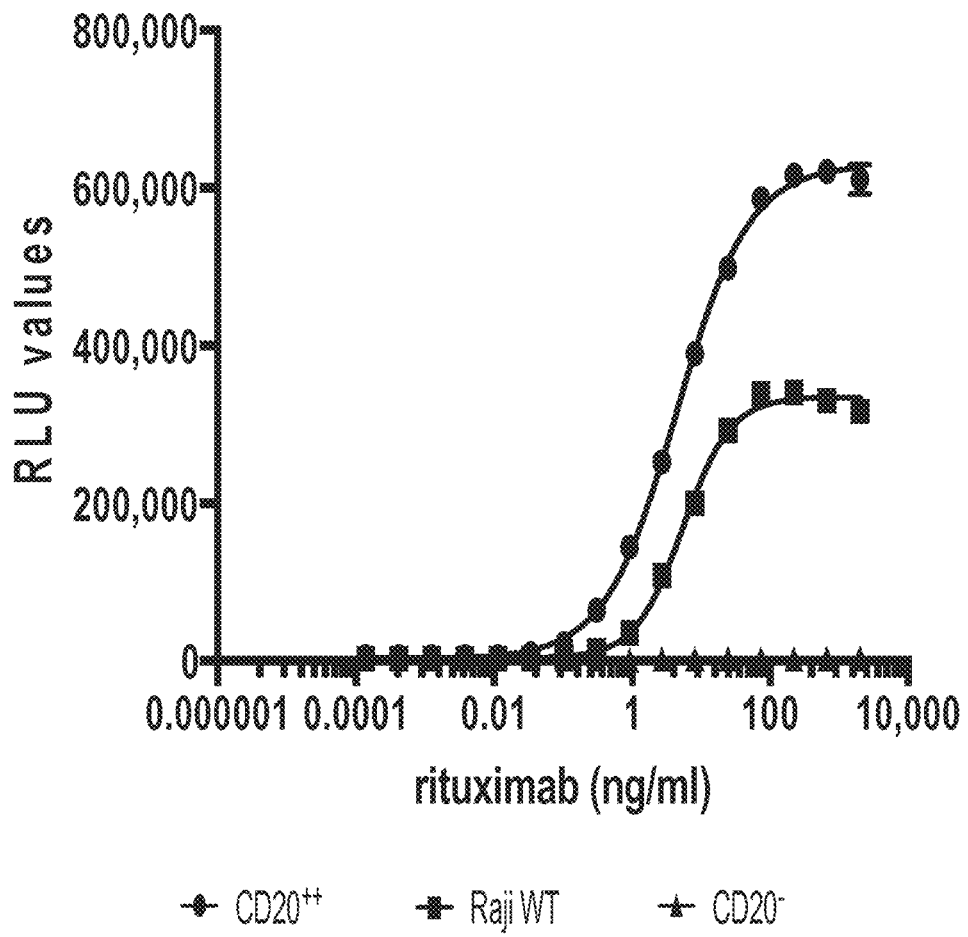
Figure 5D:
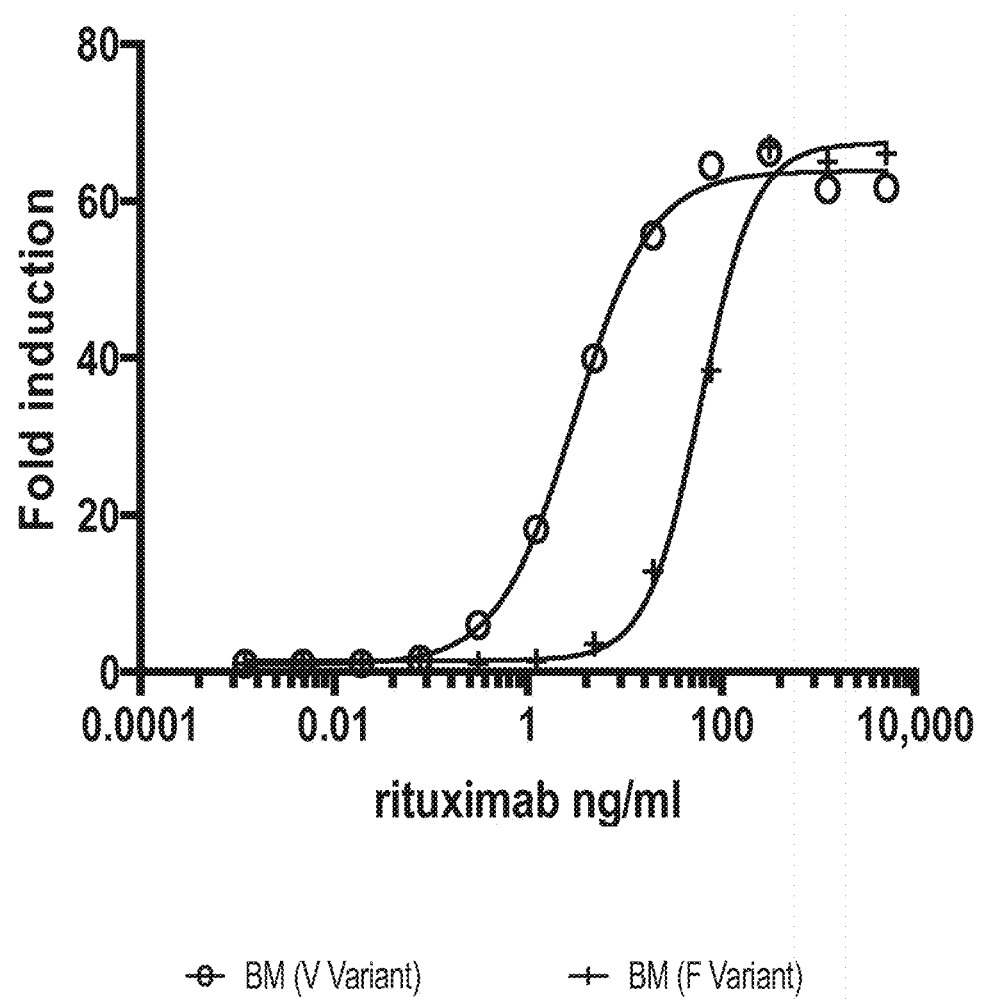
Figure 5D:
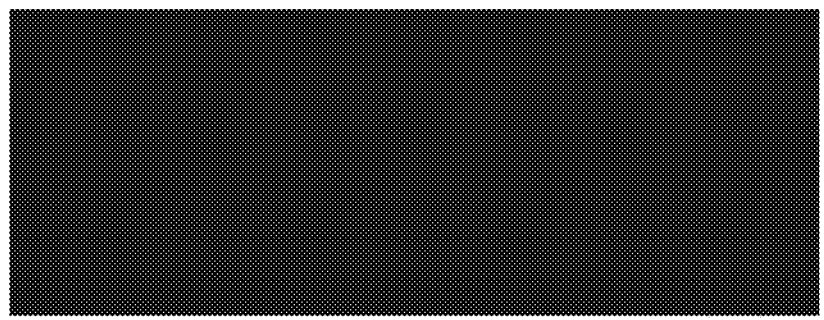
Figure 6A:
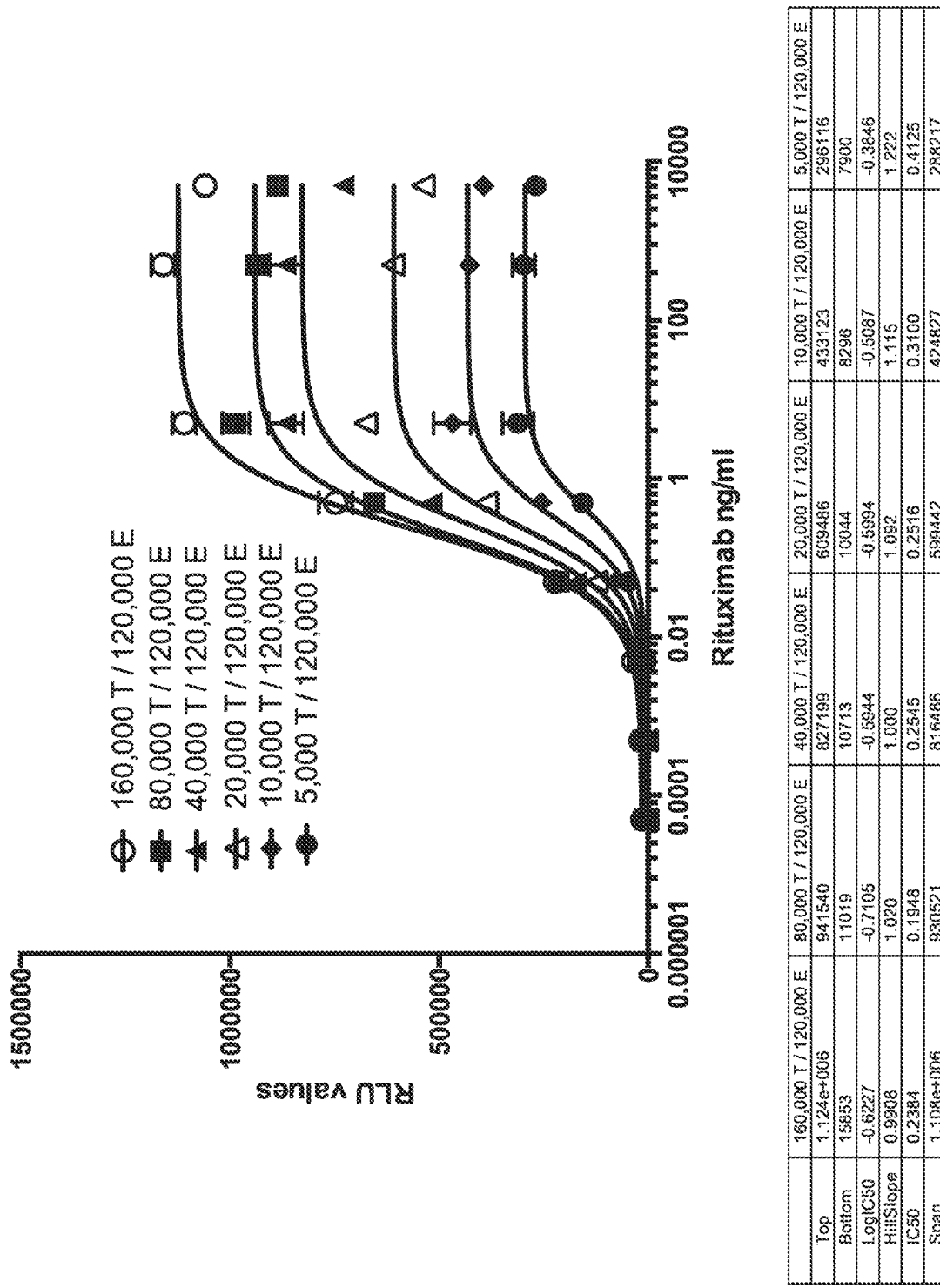

FIG. 5C illustrates a comparison of the ADCC activity rituximab determined using the iLite® effector cells and wild type (WT), CD20++ or CD20−/− target cells FIG. 5D illustrates a comparison of the ADCC activity rituximab determined using the iLite® CD16 V or F variants effector cells and CD20++ target cells FIG. 6A illustrates the quantification of the ADCC Activity of Rituximab using iLite® Effector & CD20++ Target Cells: Determination of the Optimal E:T ratio (RLU Values).

Figure 6B:
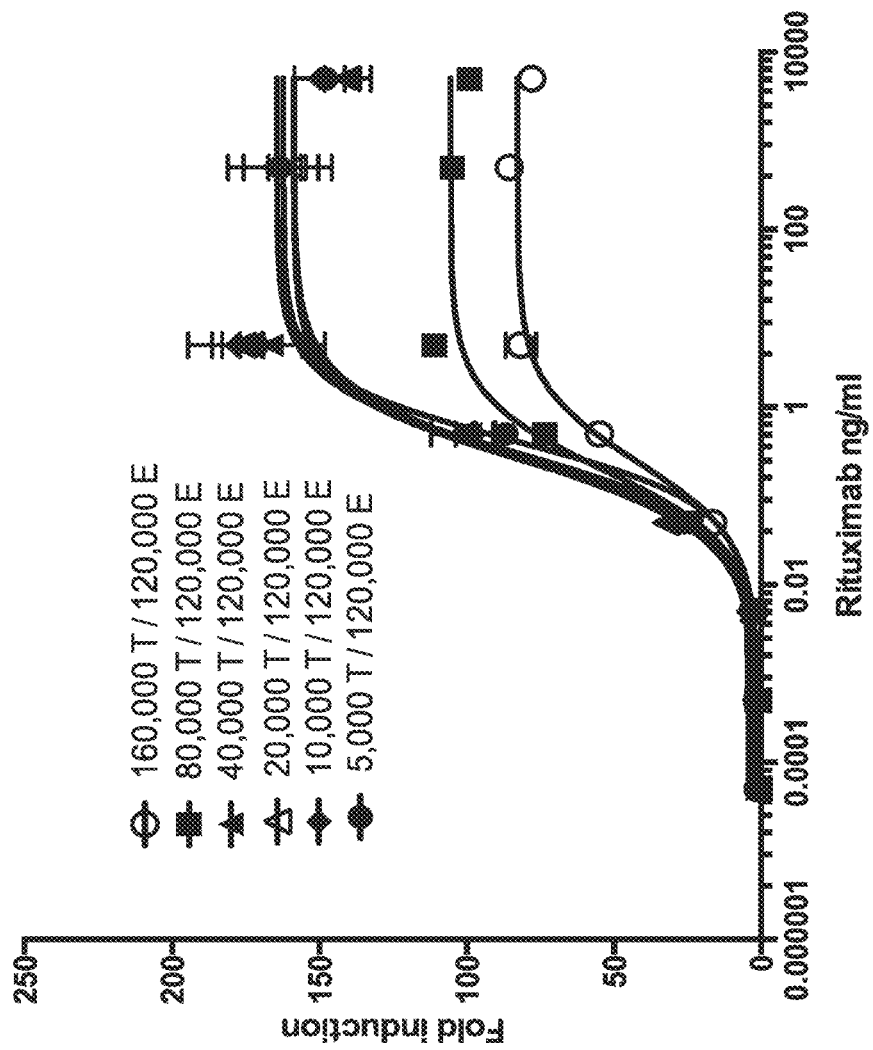

FIG. 6B illustrates the quantification of the ADCC Activity of Rituximab using iLite® Effector & CD20++ Target Cells: Determination of the Optimal E:T ratio (Fold Induction).

Figure 7A:
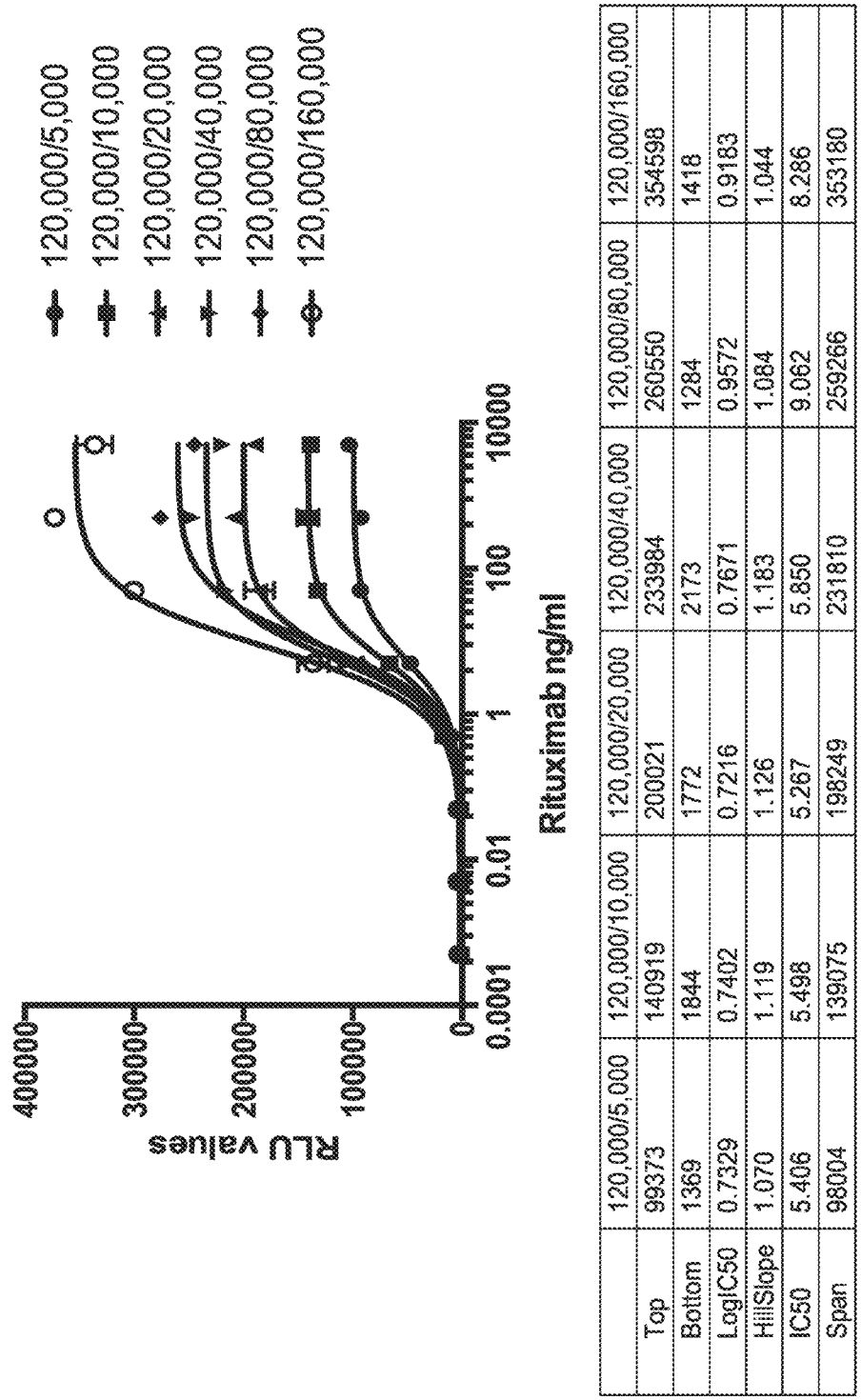

FIG. 7A illustrates the quantification of the ADCC Activity of Rituximab: Determination of the Optimal E:T ratio of Frozen Ready-to-Use Cells (RLU Values, 4 hours).

Figure 7B:
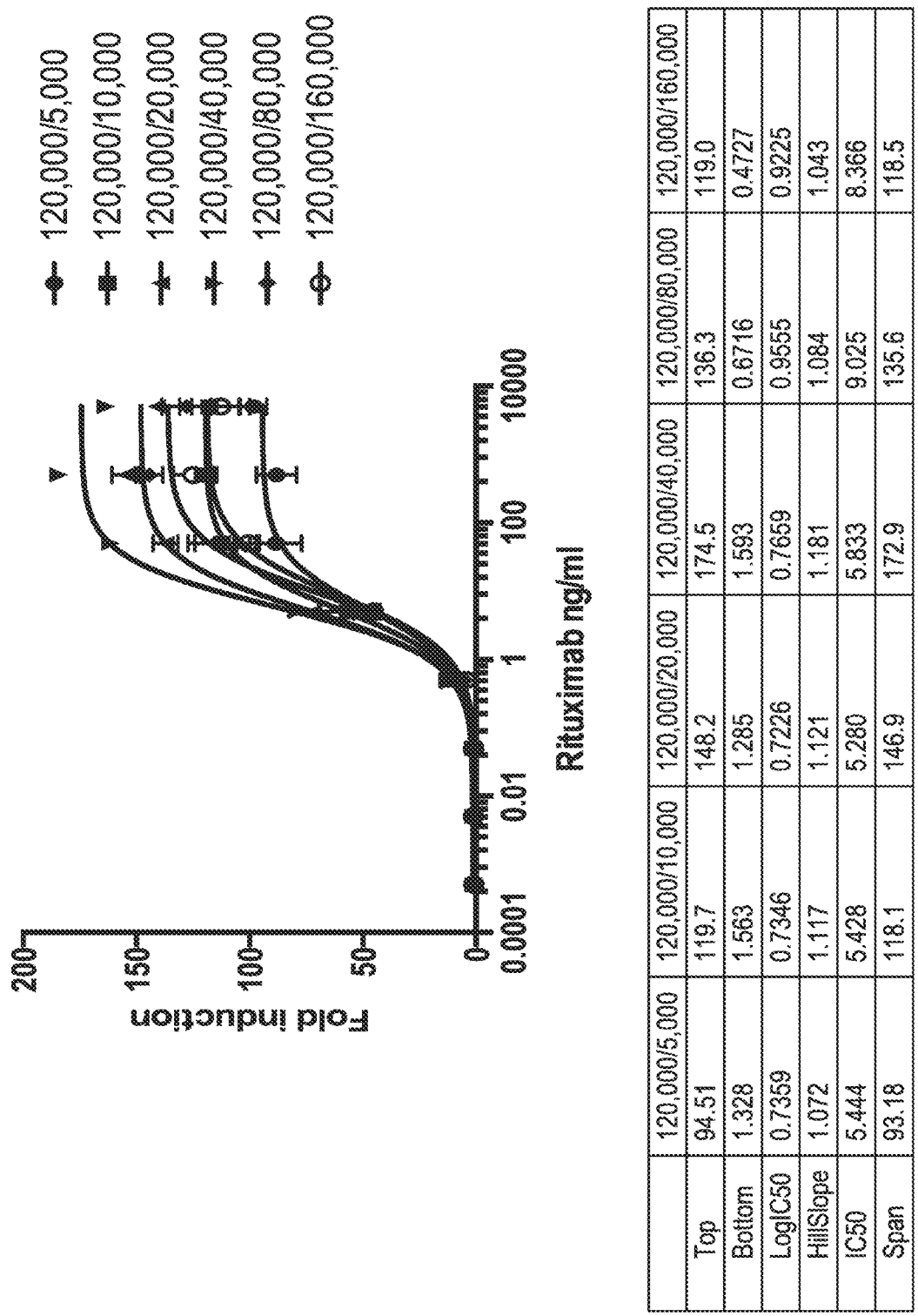

FIG. 7B illustrates the quantification of the ADCC Activity of Rituximab: Determination of the Optimal E:T ratio of Frozen Ready-to-Use Cells (Fold Induction, 4 hours).

Figure 8:
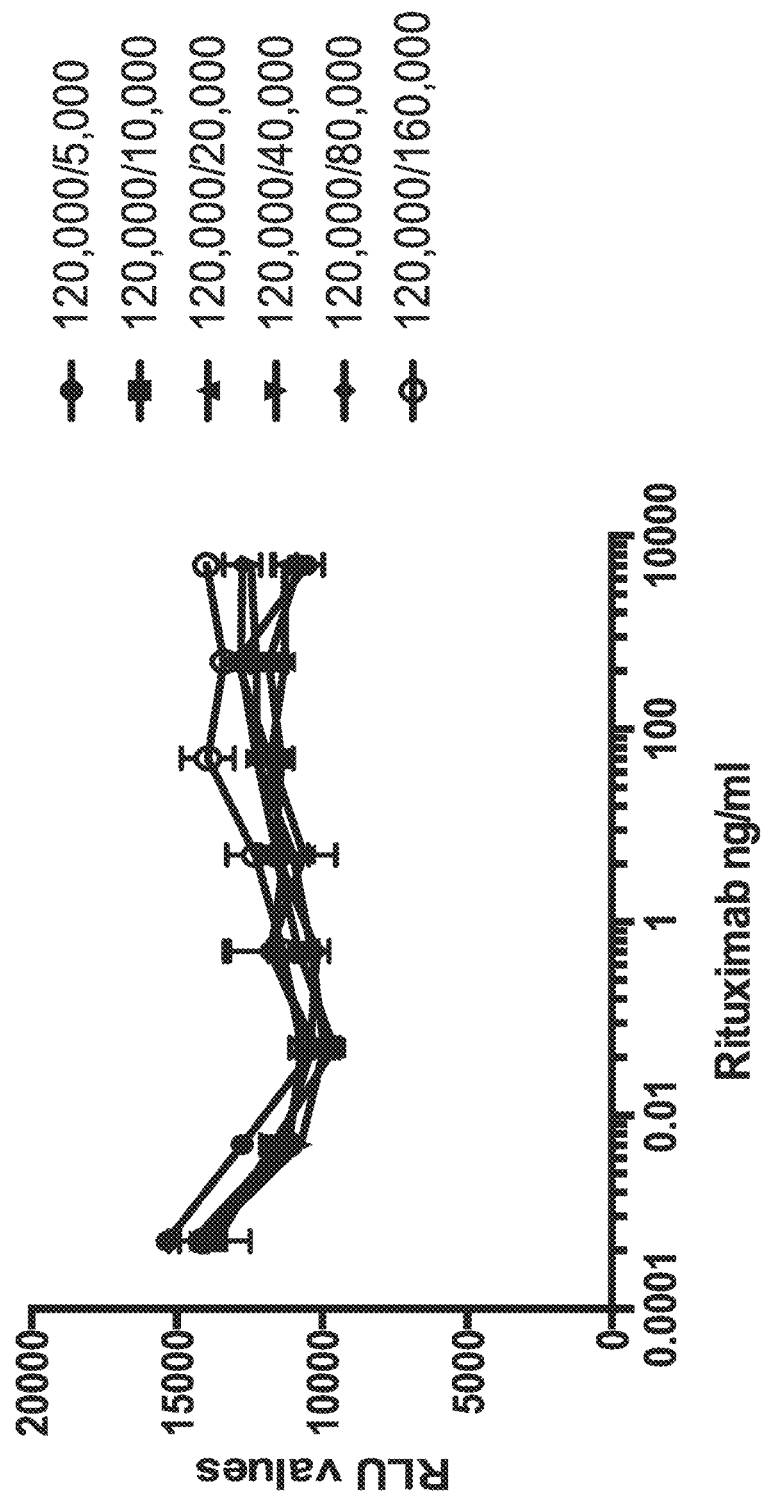

FIG. 8 illustrates the quantification of the ADCC Activity of Rituximab: Determination of the Optimal E:T ratio of Frozen Ready-to-Use Cells (*Renilla* expression, 4 hours).

Figure 9:
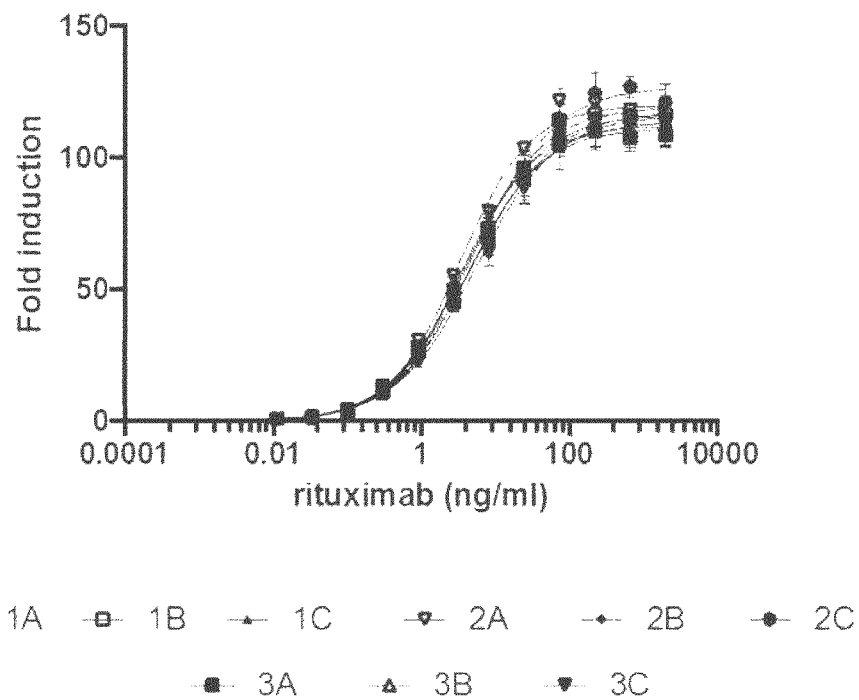

FIG. 9 illustrates quantification of the ADCC Activity of Rituximab using different vials of Frozen Ready-to-Use Cells (Fold Induction, 4 hours).

Figure 10:
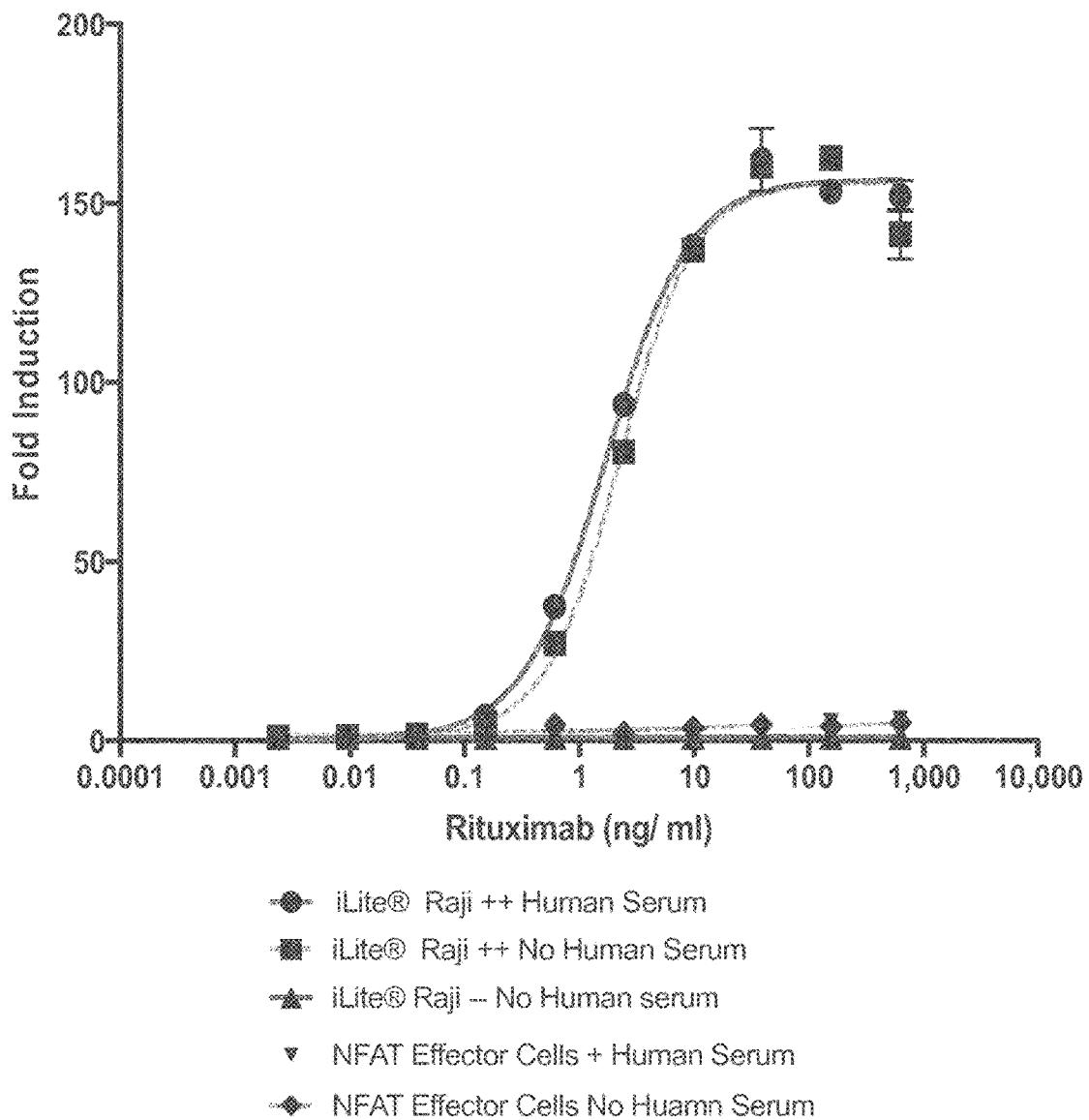

FIG. 10 illustrates the quantification of the ADCC Activity of Rituximab using iLite® Effector & CD20++ Target Cells: vs NFAT effector cells and Wild Type Raji Cells in the presence or absence of normal human serum.

Figure 11A:
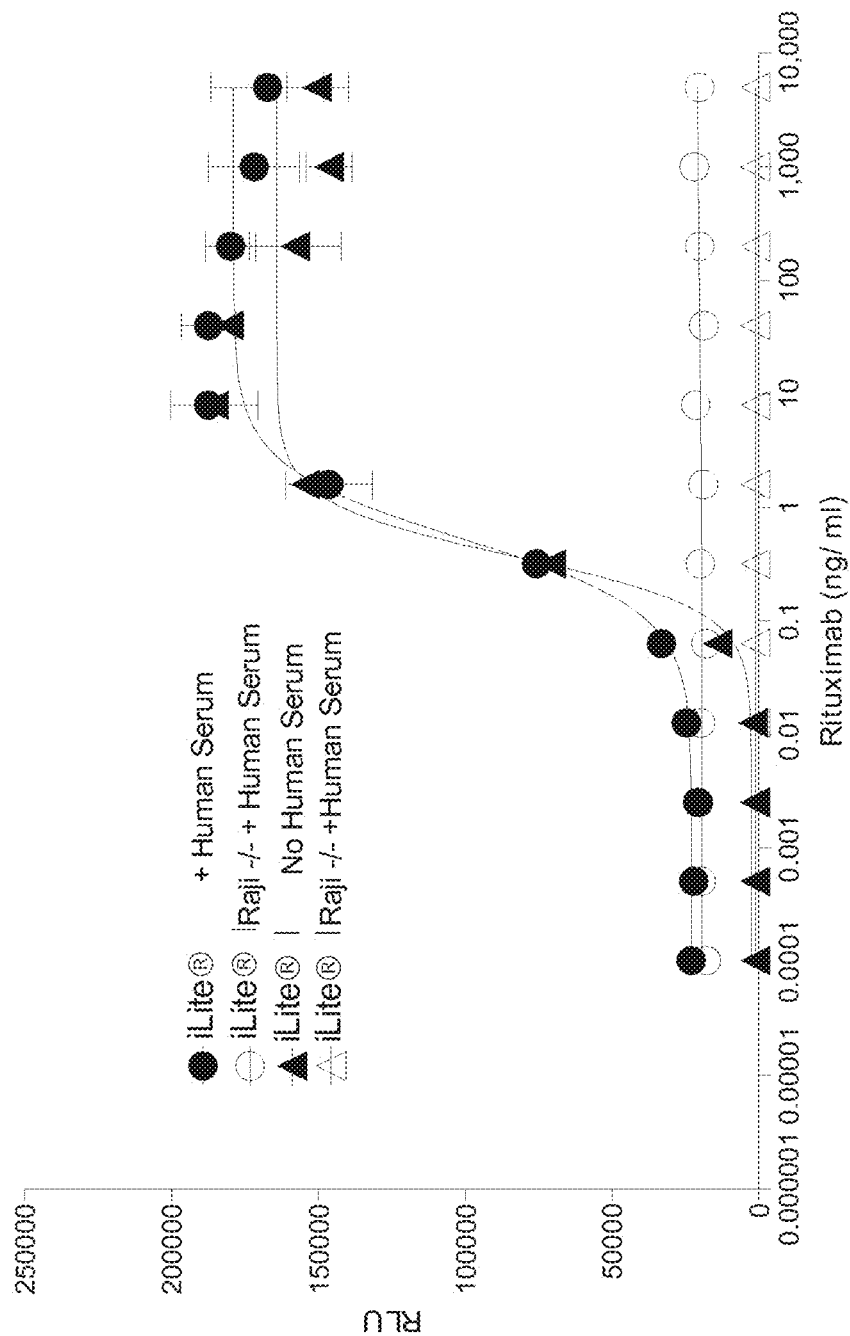

FIG. 11A illustrates the quantification of the ADCC Activity of Rituximab using iLite® Effector Cells and CD20++ & CD20-/- Target Cells in the Presence or Absence of Normal Human Serum.

Figure 11B:
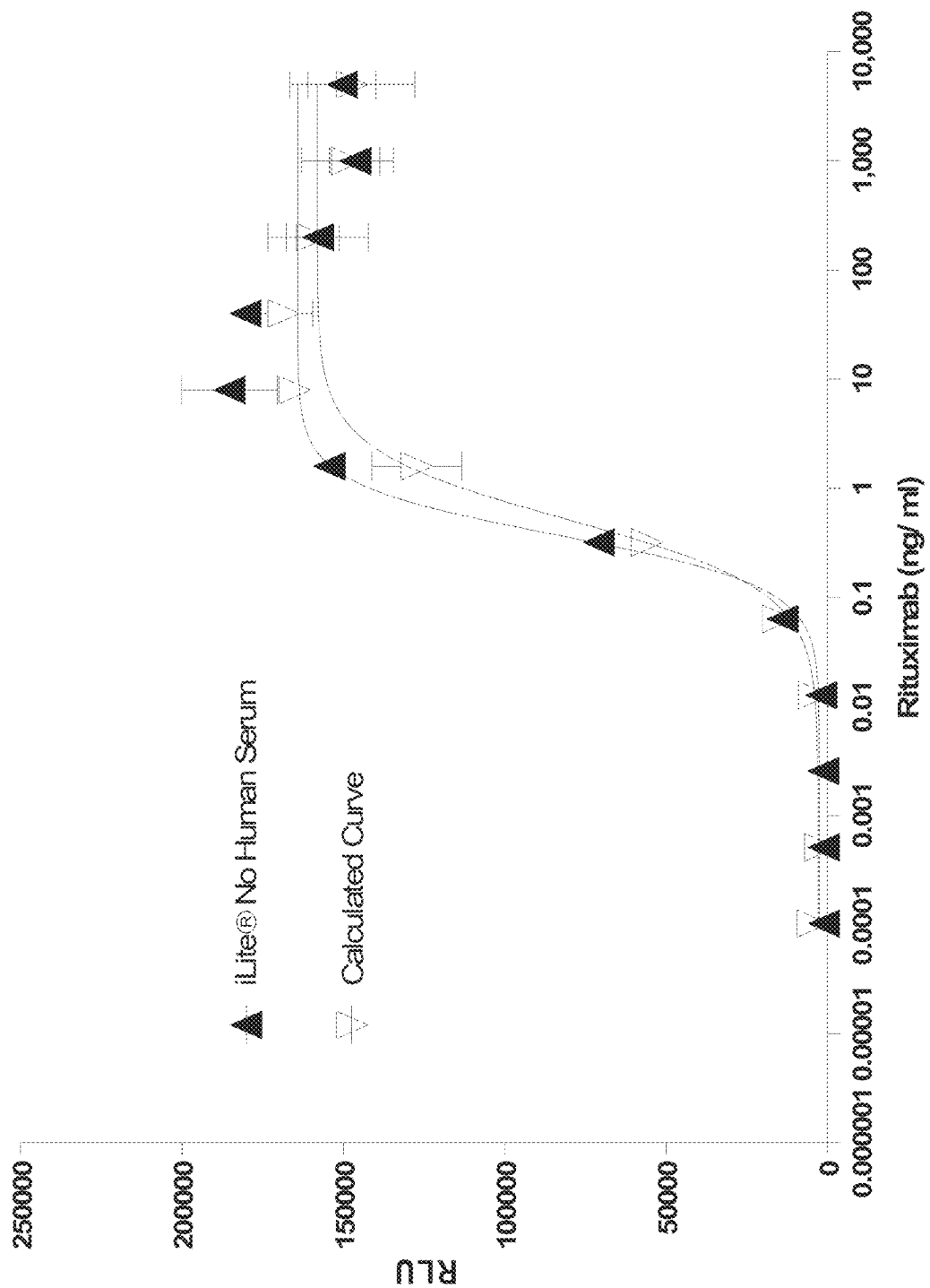

FIG. 11B illustrates the normalized ADCC Activity of Rituximab using iLite® Effector Cells & CD20++ and CD20-/- Target Cells in the Presence of Normal Human Serum calculated according to the formula:

$$[(E+T++Drug+NHS)-(E+T-+NHS)+(E+T+)]/E+T+$$

or $$[(E+T++NHS)-(E+T-+NHS)+(E+T+)]/E+T+$$

Where (E)=effector cells, (T+)=antigen positive target cells, (T-)=antigen negative target cells, and NHS=normal human serum sample. The measurements used when calculating normalized ADCC activity is the RLU (Relative Luciferase Units) measured for each entity in the above formula.

FIG. 12 illustrates the erbB2 Guide RNA Sequence (SEQ ID NO:10).

Figure 13:
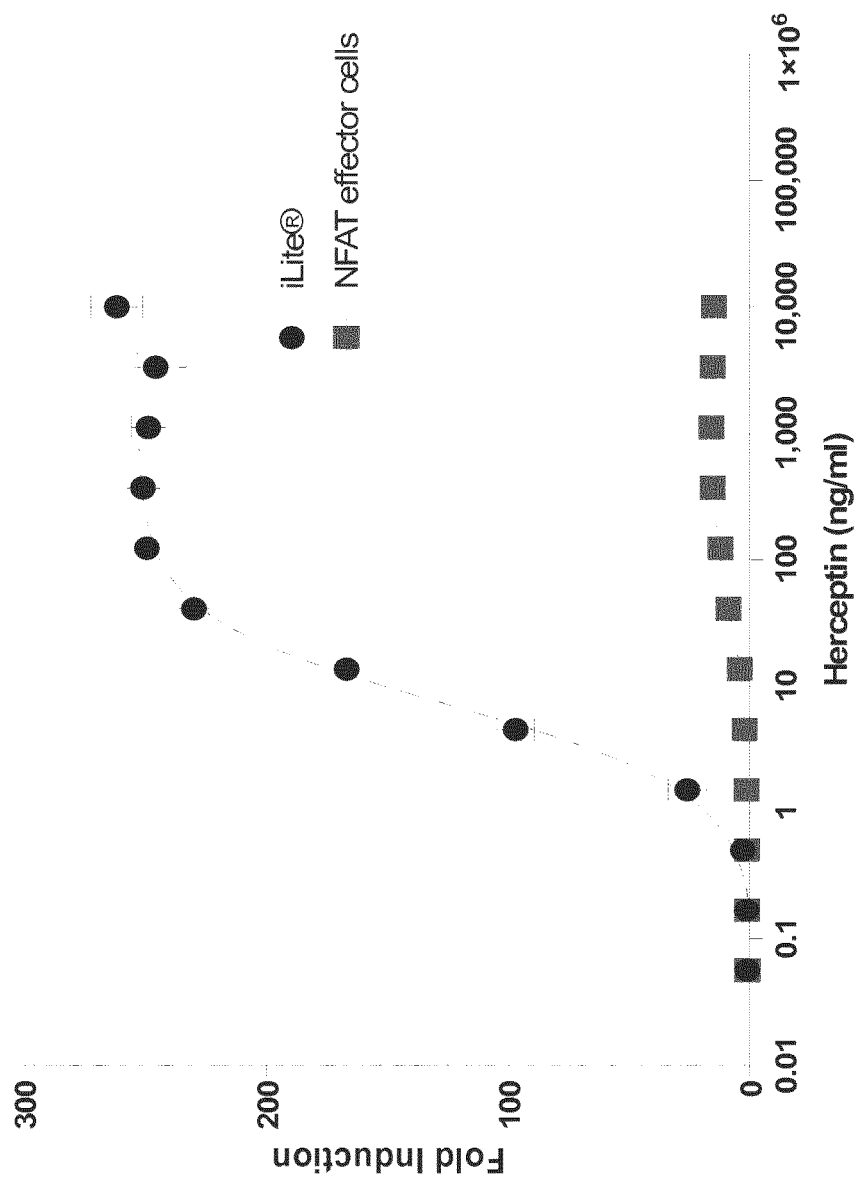

FIG. 13 illustrates the quantification of the ADCC Activity of Herceptin using iLite® Effector cells & erbB2++ HEK293 Target Cells: vs NFAT effector cells and erbB2++ HEK293 Target Cells.

Figure 14:
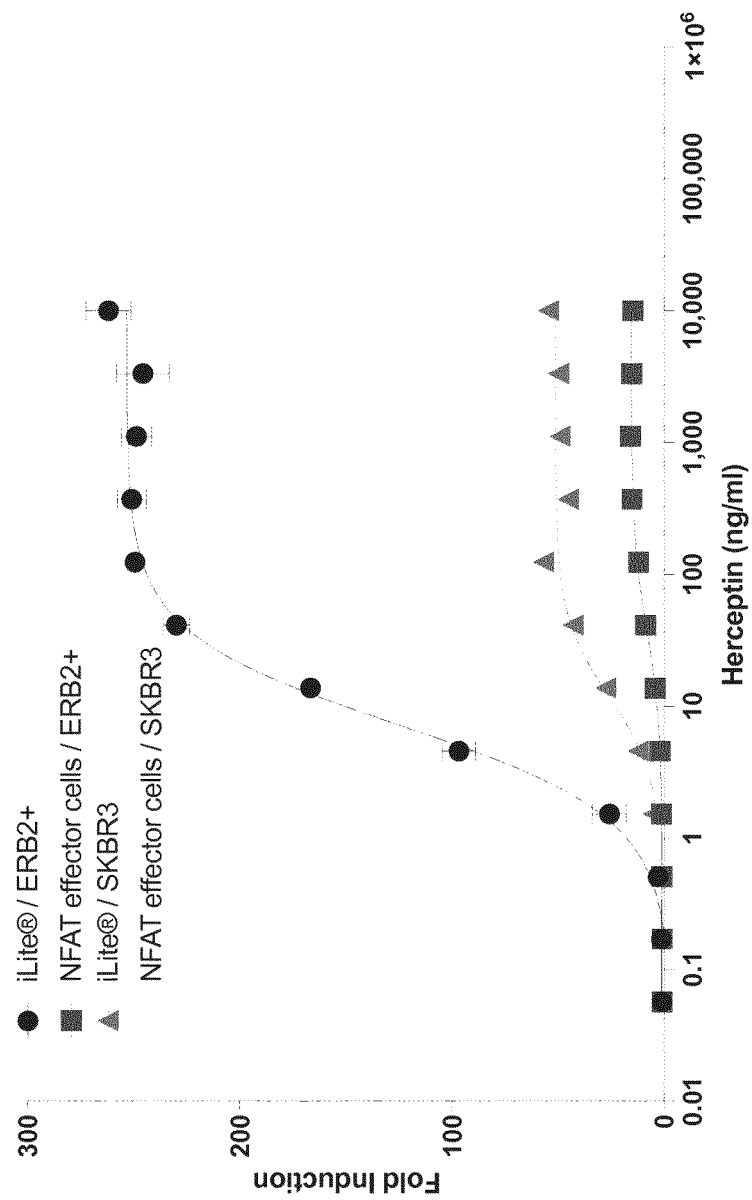

FIG. 14 illustrates the Quantification of the ADCC Activity of Herceptin using iLite® Effector Cells & erbB2++ HEK293 cells or SKBR3 Target Cells: vs NFAT effector cells and erbB2++ HEK293 target cells or SKBR3 Target Cells.

Figure 15A:
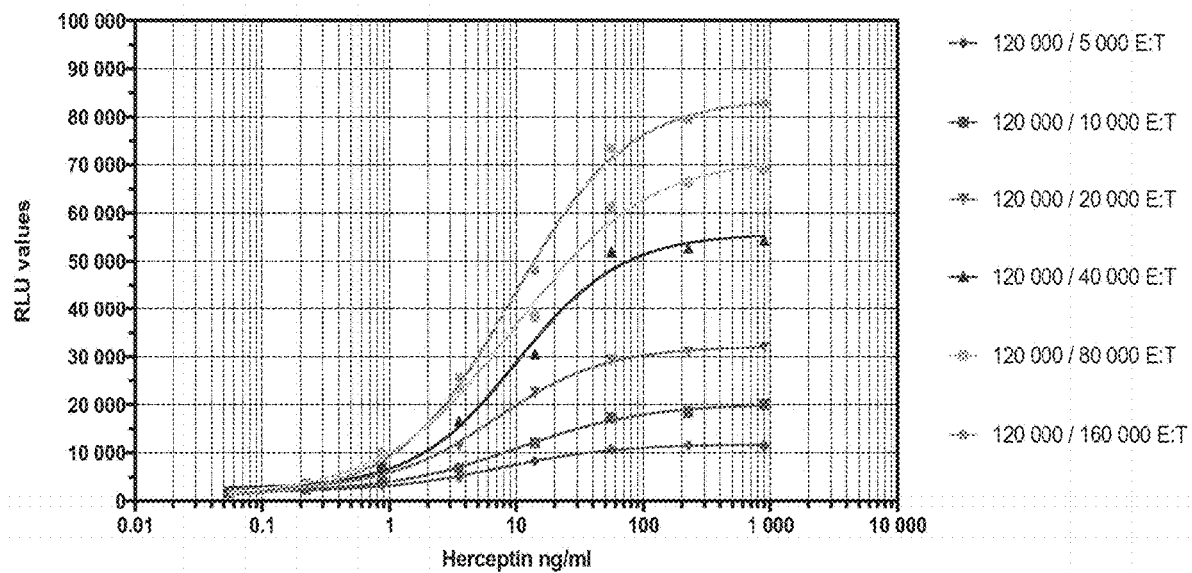

FIG. 15A illustrates the quantification of the ADCC Activity of Herceptin: Determination of the Optimal E:T ratio for Frozen Ready-to-Use iLite® Effector Cells and erbB2++ HEK293 Target Cells (RLU Values, 6 hours).

Figure 15B:
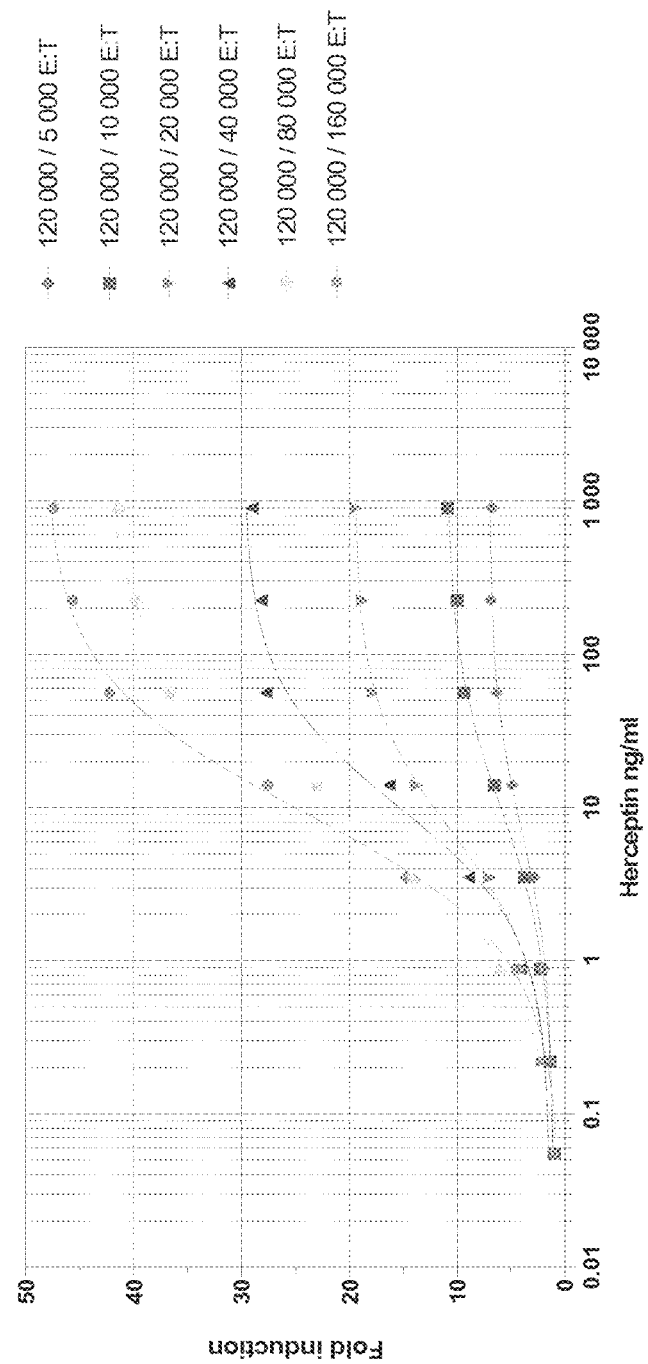

FIG. 15B illustrates the quantification of the ADCC Activity of Herceptin: Determination of the Optimal E:T ratio for Frozen Ready-to-Use iLite® Effector Cells and erbB2++ HEK293 Target Cells (Fold Induction, 6 hours).

Figure 15C:
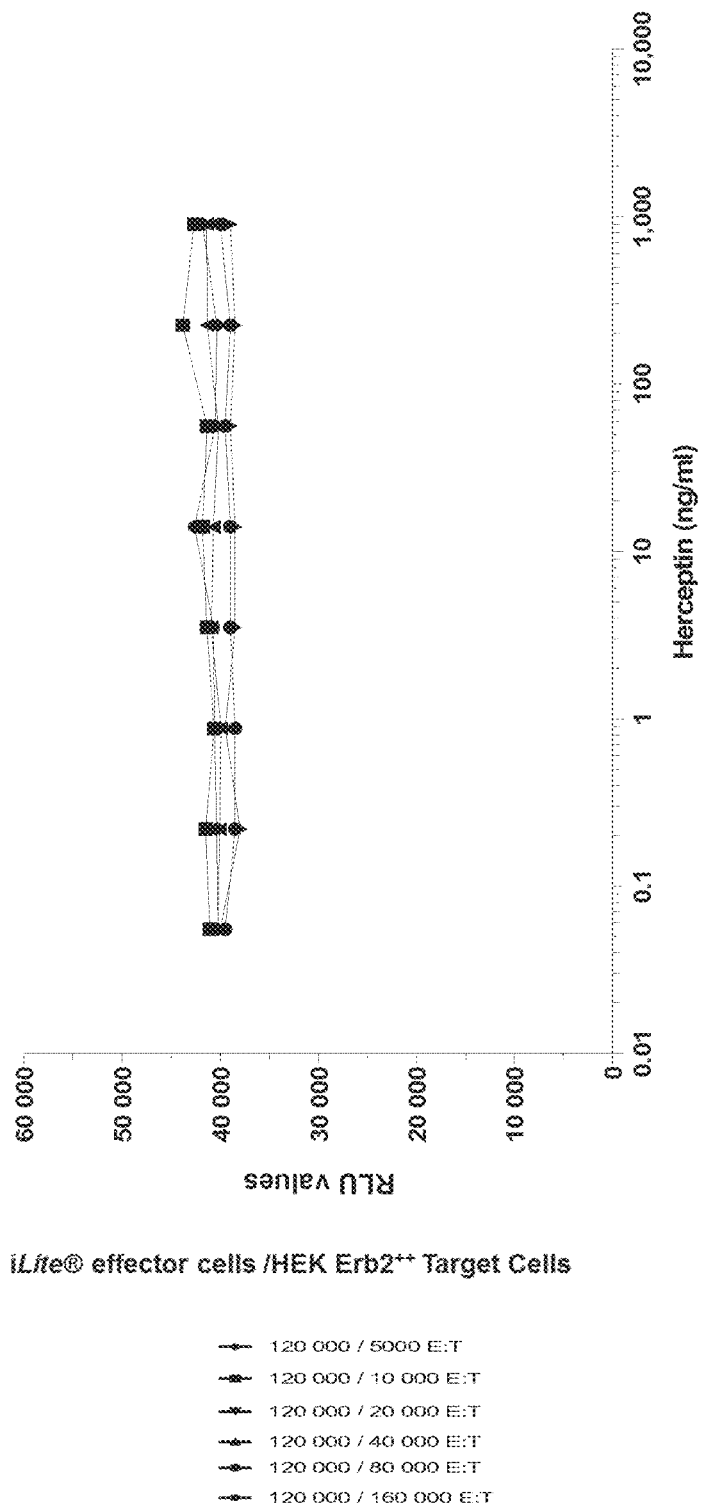

FIG. 15C illustrates the Quantification of the ADCC Activity of Herceptin: Determination of the Optimal E:T ratio of Frozen Ready-to-Use Cells for iLite® Effector Cells and erbB2 HEK293 Target Cells (*Renilla* luciferase expression, 6 hours).

Figure 16A:
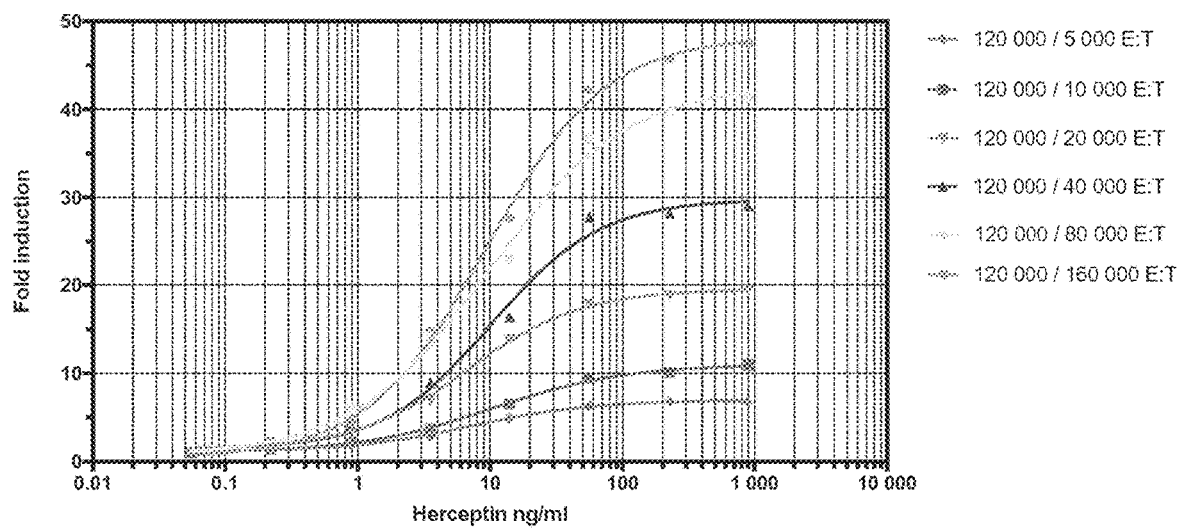

FIG. 16A illustrates the quantification of the ADCC Activity of Herceptin: Determination of the Optimal E:T ratio for Frozen Ready-to-Use iLite® Effector Cells and erbB2++ SKBR3 Target Cells (RLU Values, 6 hours).

Figure 16B:
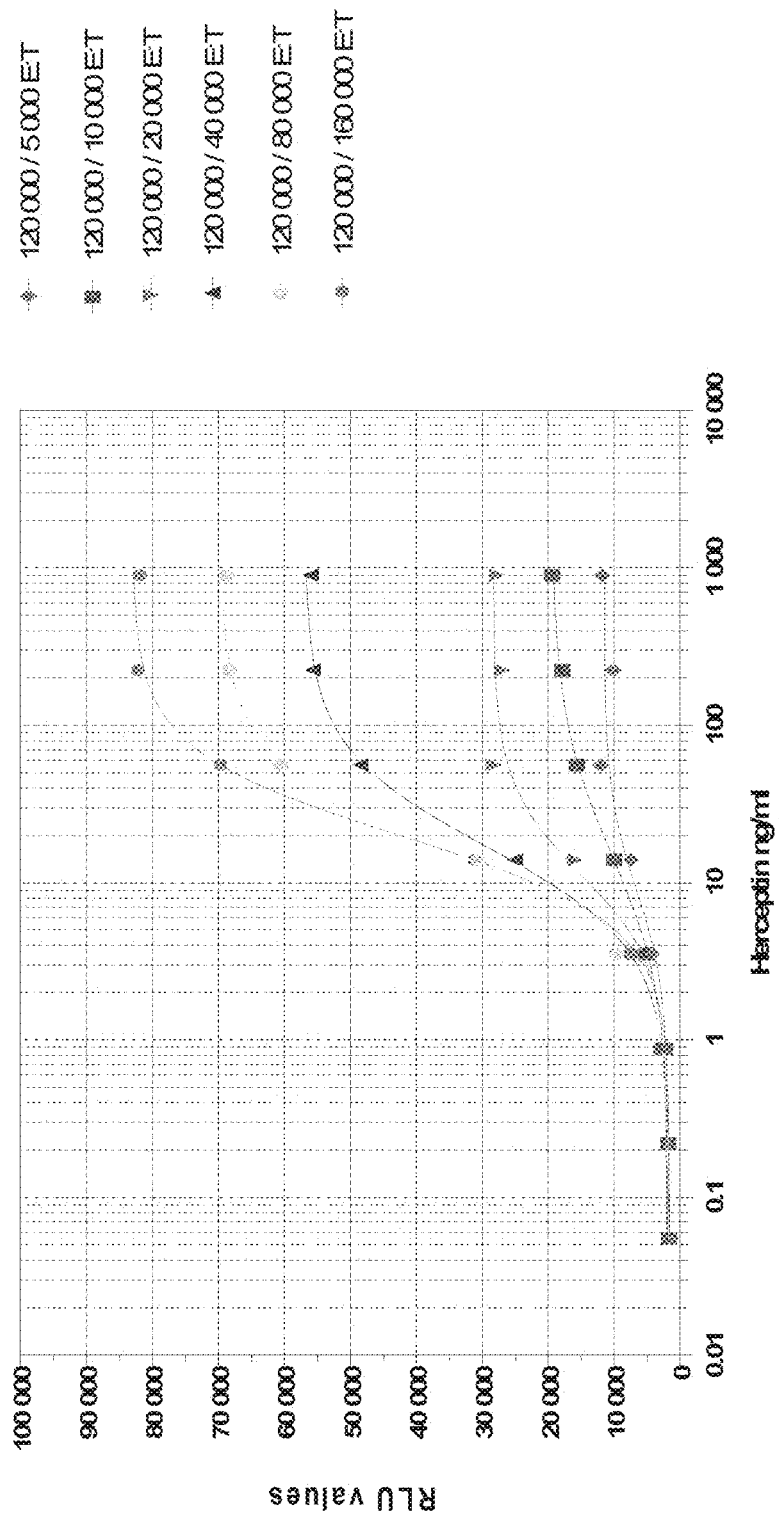

FIG. 16B illustrates the quantification of the ADCC Activity of Herceptin: Determination of the Optimal E:T ratio for Frozen Ready-to-Use iLite® Effector Cells and erbB2 SKBR3 Target Cells (Fold Induction, 6 hours).

FIG. 17 illustrates the Site Directed Mutagenesis of the Protease Cleavage Site of Human TNFα (SEQ ID NO:12).

FIG. 18 illustrates the guide RNA Sequences cloned into the nuclease vector GeneArt CRISPR (SEQ ID NO:8 and SEQ ID NO:9).

Figure 19:
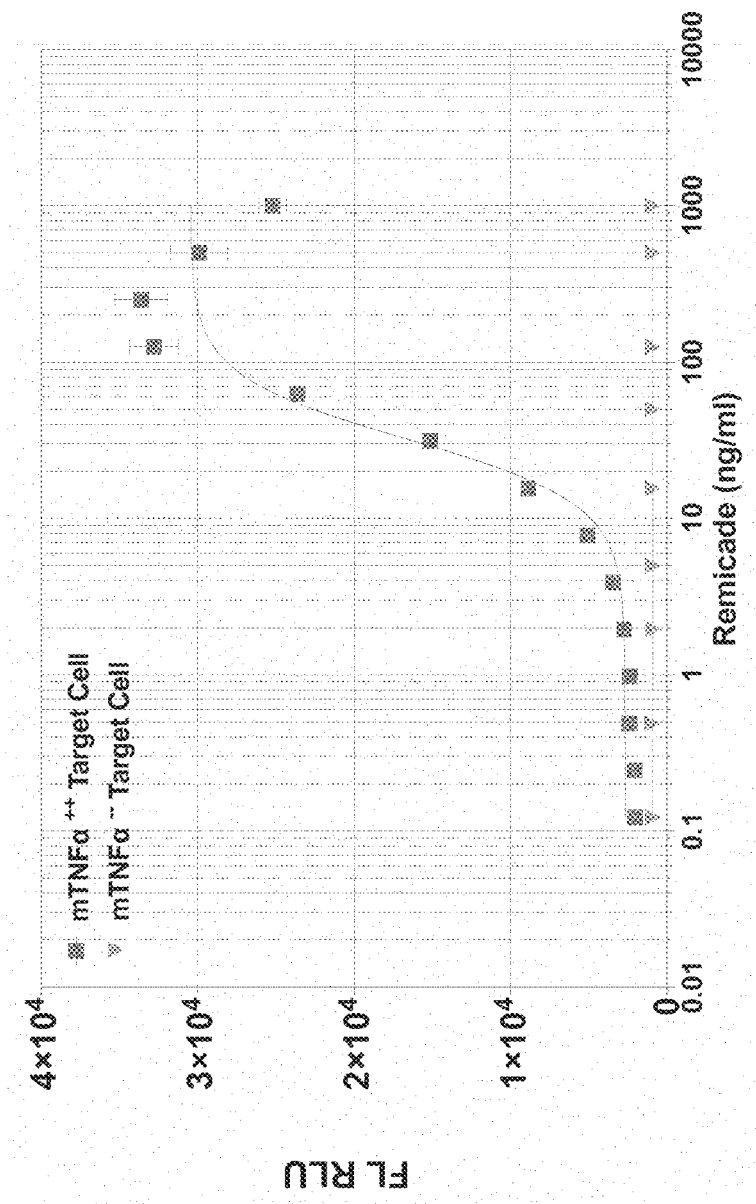

FIG. 19 illustrates the quantification of the ADCC Activity of Remicade using iLite® Effector cells & mTNFα++ Target Cells.

Figure 20A:
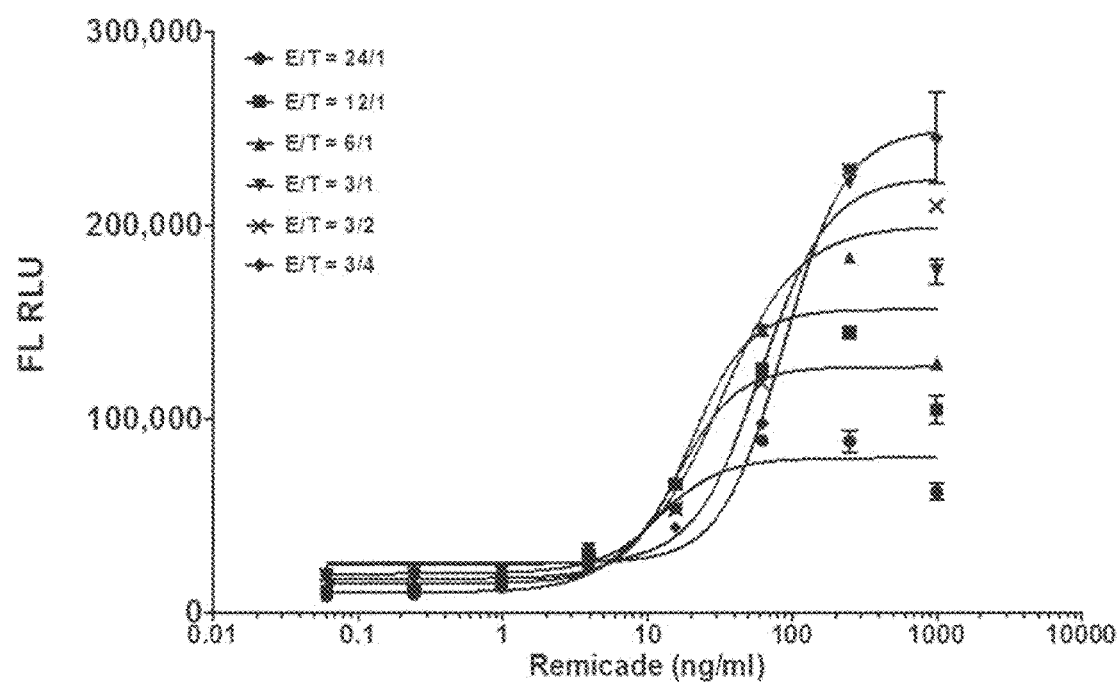

FIG. 20A illustrates the quantification of the ADCC Activity of Remicade using Frozen Ready-To-Use iLite® Effector cells & mTNFα++ Target Cells.

Figure 20B:
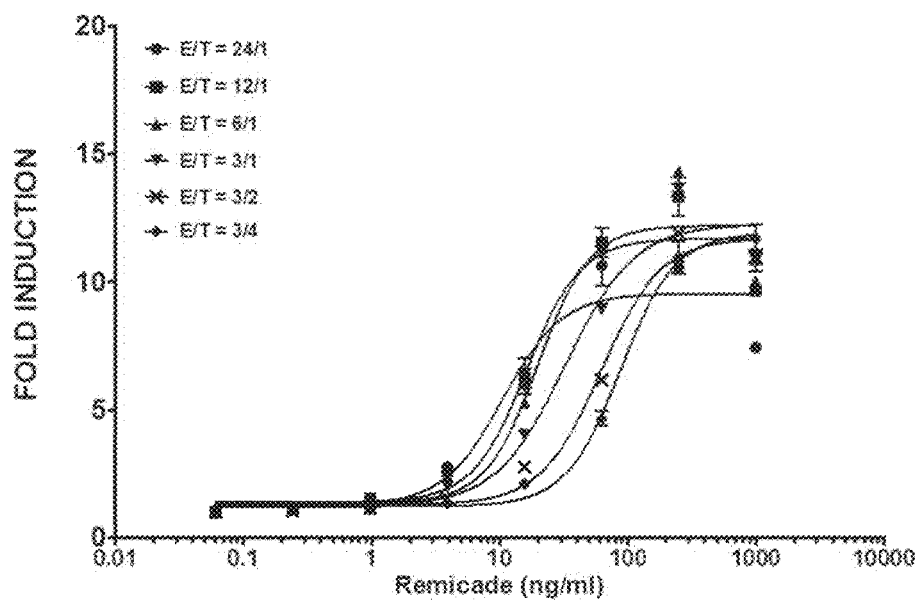

FIG. 20B illustrates the Quantification of the ADCC Activity of Remicade using Frozen Ready-To-Use iLite® Effector cells & mTNFα++ Target Cells.

Figure 21:
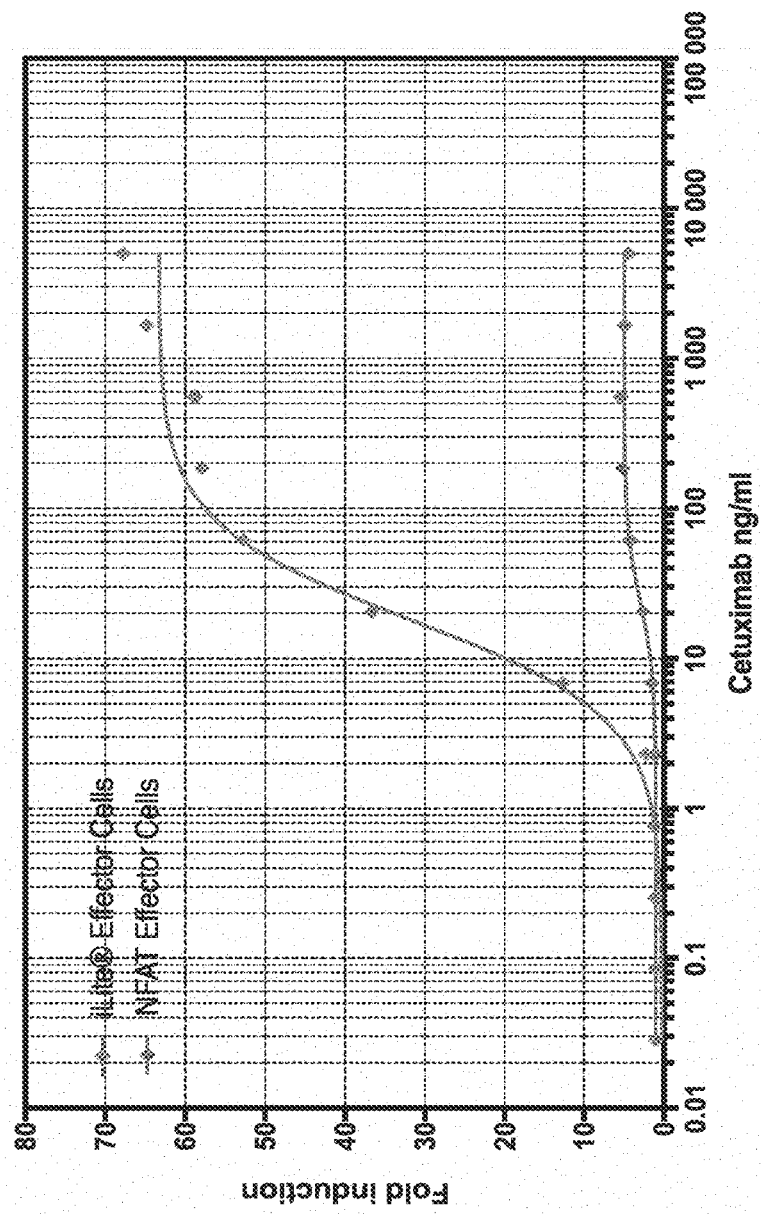

FIG. 21 illustrates the quantification of the ADCC Activity of Cetuximab using iLite® Effector cells & EGFR++ Target Cells: vs NFAT effector cells and EGFR++ Target Cells.

Figure 22A:
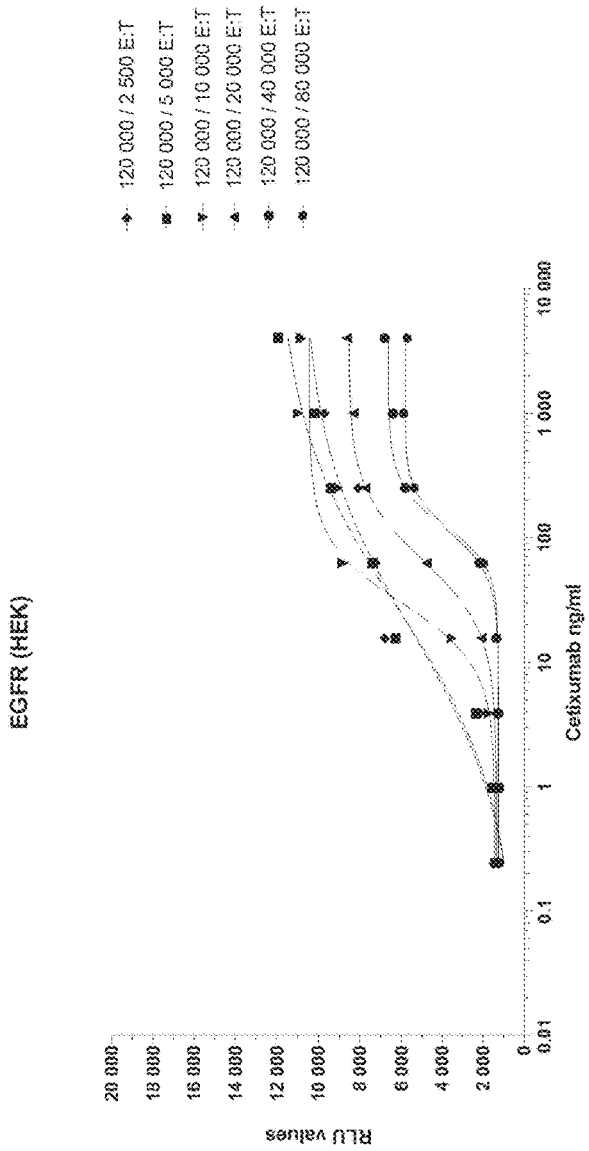

FIG. 22A illustrates the Quantification of the ADCC Activity of Cetuximab: Determination of the Optimal E:T ratio of Frozen Ready-to-Use Cells for iLite® Effector Cells and EGFR Target Cells (RLU Values, 6 hours).

Figure 22B:
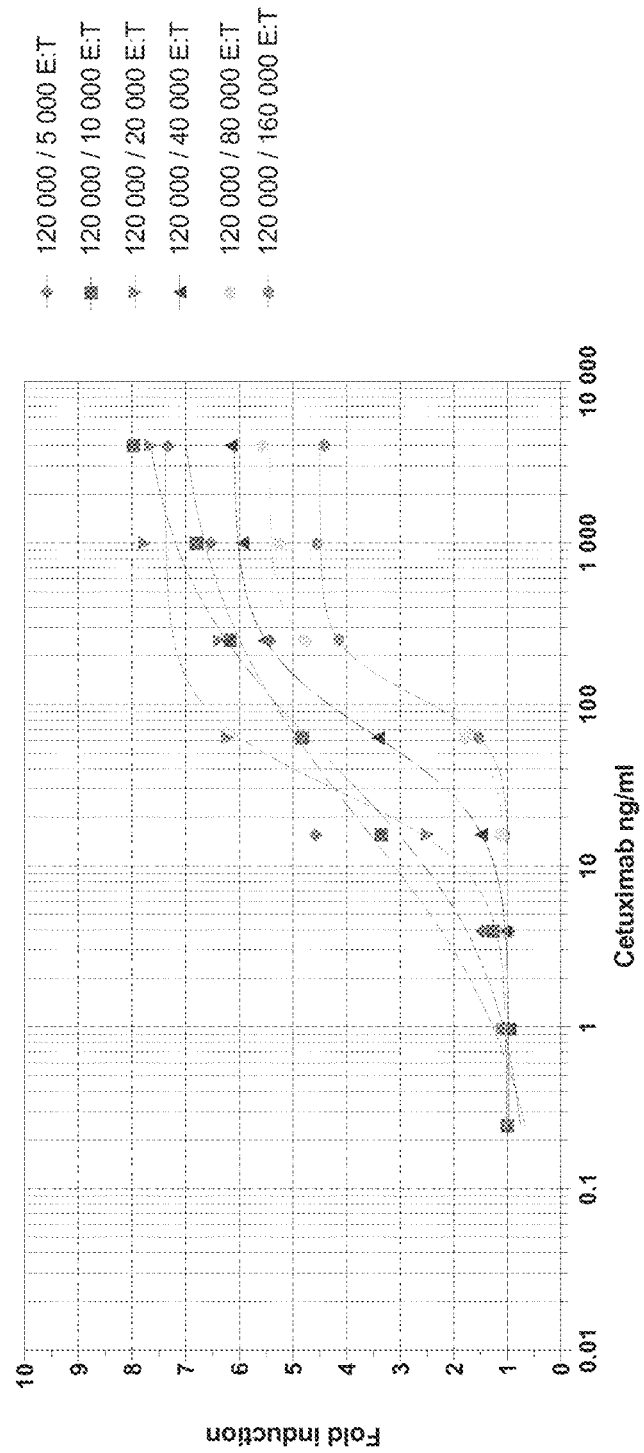

FIG. 22B illustrates the Quantification of the ADCC Activity of Cetuximab: Determination of the Optimal E:T ratio of Frozen Ready-to-Use Cells for iLite® Effector Cells and EGFR Target Cells (Fold Induction, 6 hours).

SUMMARY OF THE INVENTION

The present invention solves the above mentioned problems and provides i.a. a substantial improvement in the freeze, thaw and use effector cells of prior art assays so as to provide an improved sensitivity, an improved dynamic range, improved tolerance to the presence of human serum, and reduced incubation time. The improved sensitivity manifests itself in a substantially improved $EC_{50}$ and LLOQ (Lower Limit of Quantification). Specifically, present invention provides for a cell line and ultimately use thereof in a kit for an increased sensitivity (measured as the $EC_{50}$) or LLOQ which is at least about 10 fold in comparison with techniques known in the art. Consequently, the sensitivity or LLOQ is increased by at least about 20 fold, at least about 50 fold or at least about 100 fold in comparison with techniques known in the art. Similarly, present invention provides for a cell line and ultimately use thereof in a kit for an increased dynamic range which is at least about 10 fold in comparison with techniques known in the art. Consequently, the dynamic range is at least about 20 fold, at least about 50 fold or at least about 100 fold in comparison with techniques known in the art.

Consequently, present invention relates to a polynucleotide comprising a cis-acting regulatory sequence operably linked to a downstream promotor, wherein one or more of NF-AT, AP1, NFkB, STAT1, STAT3 and STAT5 is capable of binding to said cis-acting regulatory sequence. The invention may include said polynucleotide wherein all of NF-AT, AP1, NFkB, STAT1, STAT3 and STAT5 are capable of binding to said cis-acting regulatory sequence.

The promotor may be operable linked to an open read frame sequence encoding a first reporter protein which may be an enzyme. For the purpose of the invention any reporter protein may be used such as e.g. a luciferase or a fluorescent protein.

The invention also relates to a vector, such as e.g. a vector construct comprising the polynucleotide according to the invention. The vector may be of any type known in the art such as e.g. a plasmid or a viral vector.

The invention also relates to a cell. In particular, the invention relates to a cell comprising the vector according to the invention. The vector may be episomal or integrated in the genome of said cell. The cell may be of any origin and in particular a mammalian cell. Importantly, the cell may further express a second reporter protein which different from the first reporter protein. The cells according to the invention may be of any cell line known in the art such as e.g. Jurkat, SKBR3, or HEK293 cells.

The invention also relates to a kit or a kit of parts. The kit may comprise:
i) a cell according to the invention;
ii) a cell target cell in which the endogenous target to which an antibody is specific is invalidated (mutated); and
iii) a target cell in which the expression of the target to which an antibody is specific is enhanced.

The cell according to the invention may act as an effector cell in the ADCC mechanism.

In one aspect, the invention relates to a kit, comprising:
i) an effector cell (E) according to the invention, capable of binding to the Fc region of an antibody;
ii) a cell (T−) in which the endogenous target/antigen to which an said antibody is specific is invalidated (mutated) such that the target/antigen is not expressed by the cell; and
iii) a target cell (T+) in which the expression of the target to which an said antibody is specific is enhanced or overexpressed.

In a further aspect of the invention the cell in ii) and the cell iii) are exactly the same cell identical in all respects except the cell in ii) does not express a specific antigen recognized by the antibody or drug being assayed.

The target cell may be any type of cell. The target cell may be recombinant. The kit thus comprises a target cell in which the endogenous target to which an antibody is specific is invalidated (mutated), i.e. the target/receptor is deleted or otherwise may non-functional or has by any means lost its capability to bind the antibody in question.

The kit also comprises a target cell wherein the same target is enhanced, i.e. such that the target is overexpressed.

The target may in principle be any target to which the relevant antibody is capable to bind. In one aspect the target may be one or more of CD20, mTNFα, erbB2, EGFR.

The kit may also comprise one or more vials, such as e.g. 2 or more vials etc. In one aspect, the kit may comprise one vial which comprises a mixture of cells i) with a mixture of cells iii). In such instance the kit comprises two vials, the second vial comprises the cells of ii) as mentioned above. Thus, in one instance, the kit comprises two vials wherein one vial comprises the effector cells i) and the target cells ii) having the target to which the antibody in question is specific enhanced/overexpressed. The second vial consequently comprises the target cells ii), wherein the target is invalidated or target/receptor is deleted or otherwise may non-functional or has by any means lost its capability to bind the antibody in question.

In one aspect of the invention, one vial of the kit comprises a mixture of cells i) with a mixture of cells iii) in an optimal ratio referred herein as the E:T ratio, wherein E denotes the cells in paragraph i) above (Effector cells). T denotes the cells in iii) above (Target cells). The optimal E:T ratio is further described herein and in the experimental part.

In the kit and the method according to the invention the same E:T ratio is used for the effector cells i) and the target cells ii), as has been found for the relation between effector cells i) and target cells iii).

The invention also relates to a method for quantifying the ADCC activity ex vivo in clinical samples from patients treated with therapeutic antibodies.

The method may comprise the steps of;
a) contacting a sample obtained from a patient undergoing treatment comprising administration of an antibody, with target cells ii) according to the kit and invention,
b) subtracting the signal obtained in the presence of cells i), from the signal obtained in the presence of cells i) and target cells iii).
c) determining the ADCC activity on the basis of the signal relationship as measured in a) and b).

In the method described above a positive result for a serum sample (i.e. detectable ADCC activity) is present when the signal relationship for Effector cells i) & Target++ cells iii)/Effector cells i) & Target−/− cells ii)≥1.

A negative result for a serum sample (i.e. no detectable ADCC activity) is present when the value for Effector cells i) & Target++ cells iii)/value for Effector cells i) & Target−/− cells ii)≤1.

In one aspect, the invention relates to a method for quantifying the Antibody-Dependent Cell-mediated Cytotoxicity (ADCC) activity ex vivo in clinical samples from patients treated with therapeutic antibodies, the method comprising the steps of;
a) contacting a sample obtained from a patient undergoing treatment comprising administration of an antibody, with target cells iii) according to the invention,
b) subtracting the signal obtained in the presence of cells ii) according to the invention, in which the drug target has been invalidated, from the signal obtained in the presence of effector cells i) according to the invention and target cells iii) according to the invention,
c) determining the ADCC activity on the basis of the signal relationship as measured in a) and b), and wherein a positive result for a serum sample (i.e. detectable ADCC activity) is present when the signal relationship for Effector cells i) & Target++ cells iii)/Effector cells i) & Target−/− cells ii)≥1 and wherein a negative result for a serum sample (i.e. no detectable ADCC activity) is present when the value for Effector cells i) & Target++ cells iii)/value for Effector cells i) & Target−/− cells ii)≥1, using the formula the formula [(E+T++Drug+NHS)−(E+T−+NHS)+(E+T+)]/E+T+, or [(E+T++NHS)−(E+T−+NHS)+(E+T+)]/E+T+, wherein (E) is the effector cells according to the invention, wherein the (T+) cells are the cells according to the invention, wherein (T−) are the cells according to the invention, and NHS=normal human serum sample In another aspect, the invention relates to a method for compensating for the non-specific increase in the reporter-gene signal in the presence of human serum, the method comprising: subtracting the signal obtained in the presence of cells i), i.e. effector cells according to the invention, from the signal obtained in the presence of effector cells i) and target cells iii) according to the invention, that express the drug target or serum samples that exhibit activity that is not related to ADCC activity specific to the antibody under investigation when Effector cells i) & Target negative cells ii)>1, using the formula the formula [(E+T++Drug+NHS)−(E+T−+NHS)+(E+T+)]/E+T+, or [(E+T++NHS)−(E+T−+NHS)+(E+T+)]/E+T+, wherein (E) is the effector cells of the invention, wherein the (T+) cells are the cells according to the invention, wherein (T−) are the cells according to the invention, and NHS=normal human serum sample.

The aforementioned signal may be any suitable read-out, In cases of a luciferase, the signal may be expressed as relative luciferase units (RLU) and consequently a positive result for a serum sample (i.e. detectable ADCC activity) is present when the RLU value for Effector cells i) & Target++ cells iii)/RLU value for Effector cells i) & Target−/− cells ii)≥1. A negative result for a serum sample (i.e. no detectable ADCC activity) is present when the RLU value for Effector cells i) & Target++ cells iii)/RLU value for Effector cells i) & Target−/− cells ii)≤1

Thus the above method also enables a method for eliminating serum samples that exhibit activity that is not related to ADCC activity specific to the antibody under investigation when Effector cells i) & Target negative cells ii)>1.

The formula used for calculating the above values is $$[(E+T++Drug+NHS)-(E+T-+NHS)+(E+T+)]/E+T+ \quad (I)$$

or $$[(E+T++NHS)-(E+T-+NHS)+(E+T+)]/E+T+ \quad (II)$$

Where (E)=effector cells, (T+)=antigen positive target cells, (T−)=antigen negative target cells, and "NHS"=normal human serum sample. "Drug" denotes the measurement of ADCC activity in the presence of NHS that required the presence of drug and target cells. The measurements used when performing the calculation is the RLU (Relative Luciferase Units or more generally the Relative Luminescence Units depending on the enzyme used) measured for each entity in the above formula. The first equation/formula (I) is for the quantification of e.g. neutralizing antibodies in samples of human serum, and the second equation/formula (II) for the quantification of drug potency (activity) in human serum.

DETAILED DESCRIPTION OF THE INVENTION

These features are obtained by means of the present invention in which the recombinant effector cells are transfected with a reporter gene construct that responds not only NF-AT, but also to other transcription factor such as e.g. AP1, NFkB, and STAT5 (3-5). By using a recombinant effector cell with a reporter gene construct that recognizes NFAT, AP1, NFkB, and STAT5 the above described advantages are obtained.

In a preferred embodiment, in order to provide for a normalization of the assay, the recombinant effector cells further have a construct for the constitutive production of a luciferase that is different from that used in the reporter gene construct. For example, when the reporter gene construct produces firefly luciferase, the constitutive production may be of a second luciferase, e.g., Renilla luciferase. The activity of the first luciferase normalized relative to the activity of the second luciferase is described in US 2011/0189658 incorporated herein in its entirety by reference. When conducting the assay, after the reporter gene luciferase is measured, then a reagent is added to quench that specific luciferase so that any following reading will just read the luciferase from the constitutive construct, which then may be used for the purpose of normalization, as will be described in more detail in the examples.

The advantages of using the constitutive expression of any luciferase is that the results are not influenced by loss of effector cells or by target cell killing of effector cells, nor are the results influenced by serum matrix effects. All of these can be compensated for by the normalization obtained through the use of the measurement of the constitutive expression of the other (second) luciferase. None of these advantages can be obtained in the procedure of prior art assays which does not use such normalization.

A further improvement of the present invention over prior art assay is the use of recombinant target cells for use in the control experiments. Prior art assays uses only wild type target cells, not recombinant, for the positive control, and natural cells that do not constitutively express the antigen to which the antibody is specific, for the negative control. For example, in the CD20 assay, T cells are used which do not constitutively express CD20 as the negative control. For the positive control, wild type B-cells are used as the target. In a preferred embodiment of the present invention, target cells are produced from the same type of target cell as is being measured in vivo but with the antigen to which the antibody is specific being invalidated on the one hand (negative control) or its expression being enhanced on the other (positive control).

By using a recombinant target cell in which the antigen to which the antibody is-specific has been invalidated, one has a much improved negative control as T cells are very different from the natural target cell and these differences affect the results somewhat. For example, it can prevent the heterologous effector cell (E) target cell (T) ratio (E:T ratio) curve from being a completely zero as the number of target cells is increased as the E:T ratio is changed. This problem is solved by using a recombinant target cell in which the gene, encoding the specific antigen recognized by the monoclonal antibody, has been invalidated.

In a further preferred embodiment of the present invention, recombinant target cells are also provided that have enhanced expression of the antigen to which the antibody is specific. By having a positive control with much greater expression of the target antigen, one can obtain a much greater dynamic range in the control assay. Furthermore, the specific antigen is expressed at a constant high level and does not vary as cells proliferate or as a function of culture conditions as is the case for the wild type cells therefore affording improved assay precision. This allows the detection of subtle differences in ADCC activity of candidate antibodies to be determined. Another advantage of the recombinant target cells is that they can be provided in freeze, thaw and use format for much greater ease of use than either the harvesting or cultivation of target cells from human subjects or cultivation of target cell lines in the laboratory. Using such recombinant cells avoids the variability that will inherently be present in the target cells obtained from normal individuals or cells cultivated in vitro as such wild type cells will have variable expression of the antigen of interest depending on stage of maturation, the phase of the cell cycle or culture conditions. The use of a recombinant positive control eliminates this variability.

The availability of target cells that over-express the specific drug target and the homologous control cells in which the drug target has been specifically invalidated using genome editing provides a means for compensating for the non-specific increase in FL (firefly luciferase) signal that is observed when an ADCC assay is carried out in the presence of human serum. Thus, the signal obtained in the presence of effector cells and the negative −/− target cells at a given drug concentration can be subtracted from the signal observed in the presence of the effector cells and the positive ++ target cells at the same drug concentration as shown for CD20++ and CD20−/− target cells and rituximab in Example 2 and for infliximab, adalimumab, and etanercept in Example 4.

A further preferred feature of the present invention is a thaw and use format comprising a single frozen vial containing both effector cells and target cells at the optimal E:T ratio for a particular monoclonal antibody such as rituximab such that all the customer has to do is to add drug at a desired concentration, incubate and take a reading. A single frozen vial containing both effector cells and negative control target cells at the optimal E:T ratio for a particular monoclonal antibody is also supplied. Consequently, according to the invention the E:T ratio is in range from about 24:1 to about 1:1. Preferably, the ratio is e.g. about 24:1 to about 2:1, or about 6:1, or about 3:1, or about e.g. 1.5:1, or about 1:1. Such a format obviates the necessity for the user or the kit or method to determine the optimal E:T ratio and other assay parameters for a particular monoclonal antibody.

A further preferred feature of the present invention is specific to assays for the assessment of the ADCC activity of infliximab or any other anti-TN F-alpha antibody or Fc fusion protein such as e.g. Enbrel.

Quantification of the ADCC activity of TNFα antagonists requires a target cell expressing membrane bound TNFα. Although TNFα is initially membrane bound it is subsequently cleaved by ADAM17 (TACE) protease. Thus, in order to establish a cell line that expresses membrane-bound non-cleavable TNFα site-directed mutagenesis was used to mutate the protease cleavage site. Non-cleavable TNFα expressed on the surface of a cell will bind, however, to the TNFαRII receptor present on the surface of neighboring cells resulting in cell death and rendering the establishment of a permanent cell line difficult. Thus, or order to obviate such difficulties the TNFαRII receptor was invalidated using genome editing.

For the negative control, TNFα expression in the homologous target cell has been invalidated using CRISPR/Cas9 genome editing but not the TNFαRII receptor.

For antibodies that are directed to the HER2 receptor, the positive control is created by transfecting the target cell with a construct that expresses ERBB2.

Another feature of the present invention is the regulatory sequence used in the chimeric promoter regulating expression of the firefly reporter gene. For this purpose, it is preferable not to use a native promoter that may contain binding sites for unrelated transcription factors leading to a loss of specificity but to design the regulatory sequence carrying binding sites for NF-AT, AP1, NFkB, and STAT5 such that these transcription factor will bind to and activate the reporter gene construct, but without creating binding sites for unrelated transcription factors in the linker sequences.

A sequence that will permit these specific transcription factors to activate the promoter is non-trivial. Thus, the sequence used in the present invention is a novel embodiment of the present invention. Consequently, the invention relates to a DNA sequence having at least about 70% sequence identity to SEQ ID NO.: 1:

```
                                            (SEQ ID NO: 1)
GGAAGCGAAA ATGAAATTGA CTGGGACTTT CCGGAGGAAA

AACTGTTTCA TACAGAAGGC GTGGATGTCC ATATTAGGAT

GAGTCAGTGA CGTCAGAGCC TGATTTCCCC GAAATGATGA GCTAG.
```

Moreover, the invention relates to a DNA sequence having at least about 75% sequence identity, such as e.g. 80% sequence identity, such as e.g. about 85%, such as e.g. about 90%, such as e.g. about 95%, such as e.g. about 98%, such as e.g. about 99% sequence identity to SEQ ID NO.: 1 or a DNA sequence identical to SEQ ID NO.: 1.

Definitions

The terms "invalidated" or "muted" used interchangeably herein is meant to knock out a particular gene to ultimately change the phenotype of a cell. Effectively, the term is meant to encompass rendering a gene non-functional. An example may be the invalidation of a certain gene to remove the expression of a surface cell receptor.

The term "++" in relation to a "++ cell" is intended to mean a target cell in which the antigen/receptor is overexpressed. The terminology is used interchangeably herein with "T+". Moreover, when the expression is used together with a receptor or antigen such as e.g. CD20++ is intended to mean that CD20 is overexpressed on the cell in question. As an example without intending to limit the scope of the invention, in the case of CD20 expression levels are increased some 16-fold on CD20++ target cells relative to the wild type CD20+ Raji cells The term "−/−" in relation to "−/− cell" is intended to mean a target cell in which the antigen/receptor is not expressed, i.e. wherein the relevant gene has been knocked-out (invalidated) to mute the expression of the antigen/receptor in question. The terminology is used interchangeably herein with "T−".

Consequently, the cells no longer express detectable levels of the specific antigen recognized by the antibody since the gene encoding the specific antigen has been rendered nonfunctional. In the context of present invention this may be seen as a control target cell.

The term "E" is intended to mean "effector cells" and particularly effector cells according to the invention. The term "effector cell" is intended to mean any cell of any type that actively responds to a stimulus and effects some change (brings it about). One such example is cytokine-induced killer cells, strongly productive cytotoxic effector cells that are capable of lysing tumor cells. In a further example and in the context of present invention an effector cell is intended to mean any cell having Fc gamma receptors (FcγR or FCGR) on the surface of said cell which bind the Fc region of an antibody, wherein the antibody itself is specifically capable of binding to a target cell.

The term "T" is intended to mean a "target cell", i.e. any cell having a specific receptor/antigen that reacts with a specific hormone, antigen, antibody, antibiotic, sensitized T cell, or other substance. In relation thereto the term "(T+)" is intended to mean antigen positive target cells and consequently a cell expressing an antigen on its surface and allowing for binding of an antibody. In contrast, the term "(T−)" is intended to mean an antigen negative target cells (control target cell) and consequently a cell not expressing an antigen on its surface and thus not capable of reacting with an antibody. Put differently, antigen −/− cells (or T− cells) do not express detectable levels of the specific antigen recognized by the antibody that is being tested for ADCC activity since the gene encoding the specific antigen has been rendered nonfunctional. Specifically, the target cells used according to the invention are the same type of cells which is in contrast to known methods which usually employ one cell type as the T+ cell and employs another cells type as the T− cell. Put differently, a homologous control target cells that is exactly the same cell identical in all respects as the antigen positive target (T+) cell except that it does not express the specific antigen recognized by the antibody being assayed. As mentioned above, this is in contrast to the use of a T-cell (T lymphocyte), for example, that is often used as a control target cell for the quantification of ritiximab activity using a CD20 expressing B-cell target cells.

The term "NHS" is intended to mean Normal Human Serum in e.g. a biological sample.

EXAMPLES

Example 1: Establishment of an Engineered Effector Cell Line

Figure 2:
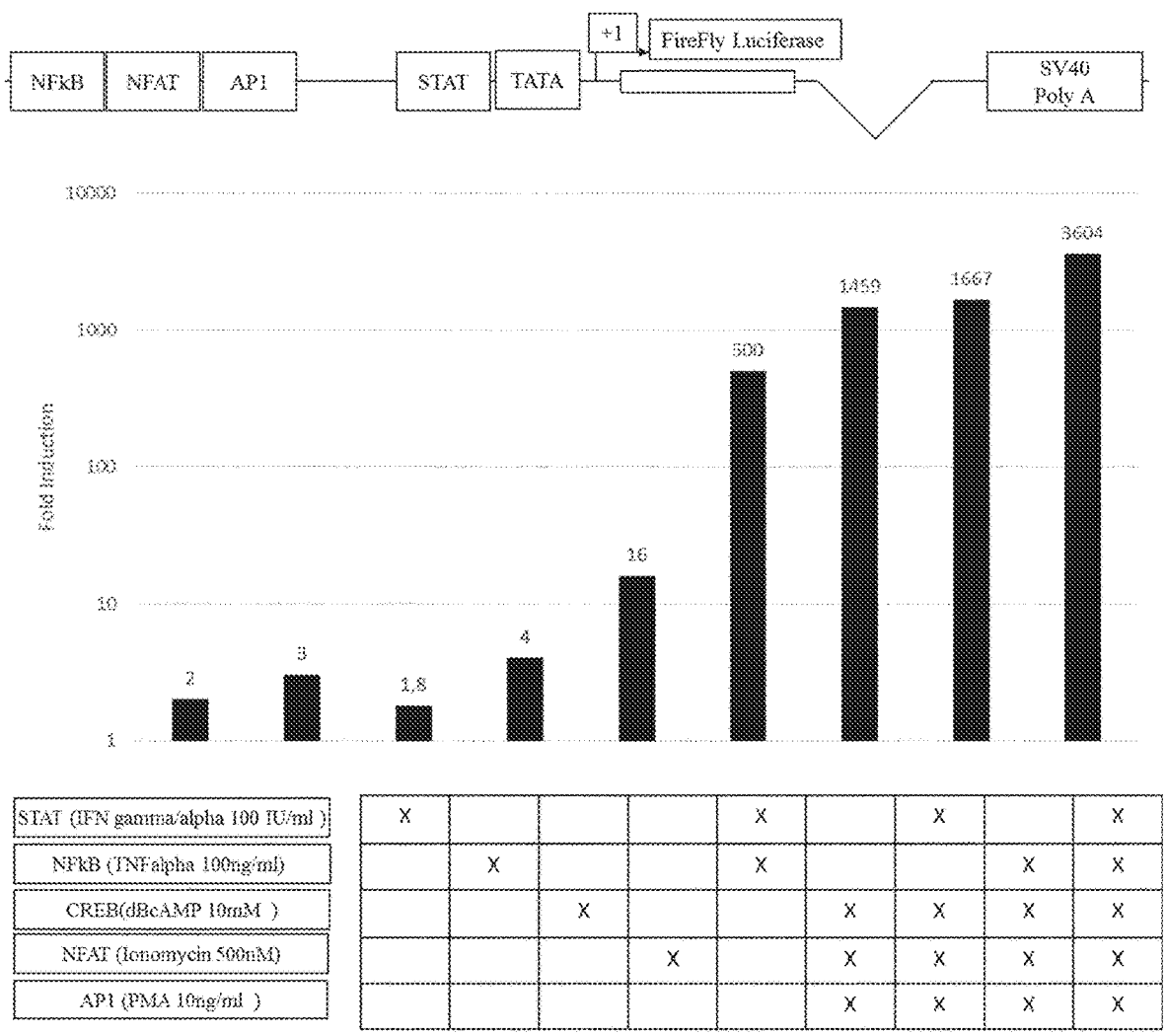
FIG. 2 illustrates the ADCC Gene Reporter Assay: CD16 Regulatory Sequence.
Figure 3:
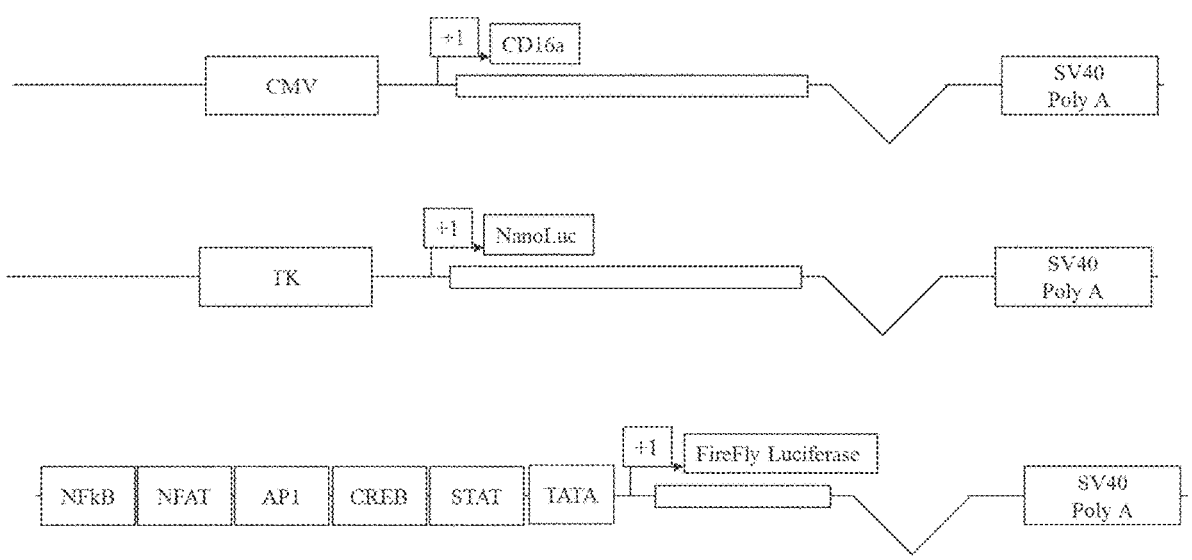
FIG. 3 illustrates the molecular Constructs used to establish the Recombinant ADCC Effector Cell Line.

In order to establish a reporter-gene construct that responds optimally to ligation of the FcγRIIIa receptor (CD16), a series of constructs consisting of variants of the NFAT, NFkB, AP1, CREB, and STAT recognition sequences (4-6) with different spacing sequences were developed in silico. The corresponding oligonucleotides for these constructs were synthesized and tested in transient transfection experiments, using the human T-cell line Jurkat, for their ability to drive transcription of the firefly luciferase (FL) reporter-gene from a minimal SV40 promoter following induction with interferon alpha & gamma (100 IU/ml), TNFα (100 ng/ml), dibutyryl cAMP (100 µM), Ionomycin (500 mM), and PMA (10 ng/ml), either alone or in combination. These functional reporter-gene constructs were then tested in an ADCC reaction in the presence of Jurkat and Raji cells at a 1:1 ratio and rituximab (500 ng/ml). The results of these experiments were used to design a synthetic chimeric promoter sequence (FIG. 1) used to regulate expression of the FL reporter gene construct (FIG. 2). Jurkat cells were then transfected sequentially, using the FuGENE HD transfection reagent (Promega Catalogue No E2311), with the FL reporter gene construct, an expression vector for FcRγIIIa (v variant), and the *Renilla* luciferase (RL) reporter gene under the control of a constitutive promoter, that allows drug-induced FL activity to be normalized with respect to the constitutive expression of RL (FIG. 3). Stable clones were isolated and characterized for ADCC activity in the presence of a given therapeutic antibody and the appropriate target cells. A suitable clone was isolated and characterized and then sub-cloned, characterized, and propagated giving rise to the clonal iLite® effector cell line.

Example 2.1: Establishment of an Engineered Target Cell Line Expressing High Constant Levels of CD20 at the Cell Surface The gene encoding CD20 was invalidated in the B-cell line Raji (ATCC® CCL-86) using CRISPR-Cas9 genome editing (7). Briefly, a guide RNA sequence (FIG. 4) was designed, synthetized, and cloned into the nuclease vector GeneArt CRISPR (Invivogen, catalog number: A21174) in order to guide the Cas9 double stranded DNA endonuclease to a specific site within exon 1 of the CD20 gene in order to isolate CD20-/- Raji cells (FIG. 5).

CD20-/- Raji cells were then transfected with a CD20 expression vector (pUNO1-CD20) using the FuGENE HD transfection reagent (Promega Catalogue No E2311). Positive clones were enriched using fluorescent activated cell sorting and a FITC labelled anti-CD20 monoclonal antibody (FAB4225F, R & D Systems). Stable clones were isolated and characterized for ADCC activity in the presence of effector cells and rituximab and then sub-cloned. A suitable sub-clone was isolated, characterized and propagated giving rise to the CD20++ target cell line (FIG. 5).

Example 2.2: Establishment of the Optimal E:T Ratio

Varying concentrations of iLite® effector cells (E) were incubated with varying concentrations of CD20++ target cells (T) in order to determine the optimal effector target cell ratio (E:T) for the quantification of the ADCC activity of rituximab (FIGS. 6A & 6B). The optimal E:T ratio for effector cells and RAV2.1S8 target cells in culture was found to be 3:1 that gave readily measurable levels of FL activity (FIG. 6A) while at the same time yielding an optimal dynamic range (FIG. 6B) after 4 hours incubation of the effector cells and target cells in the presence of increasing concentrations of rituximab.

Vials of iLite® effector cells and vials of CD20++ target cells were frozen separately using standard techniques. Upon thawing, effector cells and target cells were mixed at E:T ratios ranging from 24:1 to 2:1 and incubated for 4 hours in a 96-well white sided microtiter plate (Perkin Elmer 6005181) in the presence of increasing concentrations of rituximab in RPMI 1640 culture medium+10% fetal bovine serum (FBS). FL activity was then determined using the Dual Glo (Promega 22920) dual luciferase substrates and light emission was quantified in a luminometer (GloMax, Promega) and expressed as relative luciferase units (RLU). Results are presented as in the form of a 4 parametric logistic (4PL) plot as shown in FIGS. 6 & 7. The associated Tables to FIGS. 6 & 7 outline the principal 4PL parameters for the iLite® effector cells and & CD20++ target cells at different E:T ratios (FIGS. 6 & 7). An E:T ratio of 3:1 was found to be optimal after 4 hours incubation of the effector and target cells (FIGS. 6 & 7). The level of expression did not increase as a function of the E:T ratio (FIG. 8) and can thus be used as a normalization gene. In addition, to providing a convenient and cost-effective means of quantifying the ADCC activity of therapeutic antibodies frozen ready-to-use effector and target cells also provide the basis for the establishment of highly precise and reproducible assays with a low degree of vial-to-vial and lot-to-lot variation as illustrated in FIG. 9 & the associated Table showing the principal parameters of a 4PL plot.

Example 2.3: Quantification of the ADCC Activity of Rituximab in the Presence of Human Serum The presence of human serum in an ADCC assay causes a concentration dependent increase the reporter gene activity of the effector cells in the absence of the therapeutic antibody due to non-specific binding of the IgG present in human serum to the surface of the target cells. The availability of homologous target cells in which the specific drug target has been invalidated by genome editing provides a means of estimating the level of non-specific activation in the presence of the target negative cells and a given concentration of human serum that can be subtracted from that observed with the homologous cells expressing the specific drug target in the presence of the same concentration of human serum. The non-specific interaction of human serum with the target cells is of low affinity that does not change significantly the slope of the 4PL curve observed with the interaction of the therapeutic antibody and the specific target cells (FIG. 10 & associated Table).

Vials of iLite® effector cells and vials of CD20++ target cells were thawed, and effector cells and target cells were mixed at an E:T ratio of 3:1 and incubated for 4 hours in a 96-well white sided microtiter plate (Perkin Elmer 6005181) in the presence of increasing concentrations of rituximab in RPMI 1640 culture medium+10% fetal bovine serum (FBS) either in the presence or absence of a 1/20 final dilution of a pool of normal human serum (NHS). FL activity was then determined using the Dual Glo (Promega 22920) dual luciferase luciferase substrates and light emission was quantified in a luminometer (GloMax, Promega) and expressed as relative luciferase units (RLU). Results are presented in the form of a 4 parametric logistic (4PL) plot as shown in FIG. 10. The associated Table to FIG. 10 outlines the principal 4PL parameters for both the iLite®/CD20++ and NFAT/WT Raji assays in the presence and absence of normal human serum. The response of effector cells & CD20++ target cells, (expressed as fold induction relative to the control sample without rituximab), as shown in FIG. 10 was found to be significantly greater than that of the NFAT effector cells & wild type CD20+ Raji cells. Thus, a dynamic range of approximately 150 fold was obtained for the iLite® effector cells & CD20++ target cells versus approximately 10 fold for the NFAT effector cells & WT Raji cells in the absence of human serum. The EC50 of the assay was approximately 2.0 ng/ml compared with 1.2 µg/ml for the NFAT/WT Raji cells assay in the absence of human serum. The response of the iLite®/CD20++ assay was also markedly less influenced by the presence of human serum compared to the NFAT/WT Raji assay (FIG. 10). The response of iLite® effector cells and Raji−/− target cells at an E:T ratio of 3:1 to the presence of increasing concentrations of rituximab did not differ significantly from that of the control sample without rituximab as shown in FIG. 10.

In order to compensate for non-specific activation of the reporter gene in the presence of a given concentration of human serum the effector cell signal observed in the presence of CD20−/− negative target cells at a given concentration of rituximab was subtracted from the signal observed in the presence of the effector cells and the CD20++ target cells at the same concentration of rituximab according to the formula [(E+T++Drug+NHS)−(E+T−+NHS)+(E+T+)]/E+T+, or [(E+T++NHS)−(E+T−+NHS)+(E+T+)]/E+T+, wherein (E)=effector cells, (T+)=antigen positive target cells, (T−)=antigen negative target cells, and NHS=normal human serum sample, in order to obtain a normalized dose-response curve for the ADCC activity of rituximab (FIGS. 11A & 11B).

Effector cells & target cells frozen together in a single vial at the optimal E:T ratio of 3:1 when thawed and incubated with rituximab under the same conditions as effector and target cells frozen separately gave similar results to those obtained with cells frozen separately thus providing a more convenient format that confers a considerable time saving.

Example 3: Establishment of an Engineered Target Cell Lines Expressing High Constant Levels of erbB2 at the Cell Surface The gene encoding erbB2 was invalidated in HEK293 cells (ATCC® CRL-1573) and SKBR3 cells (ATCC® HTB-30) using CRISPR-Cas9 genome editing (7). Briefly a guide RNA sequence (FIG. 12) was designed, synthesized, and cloned into the nuclease vector GeneArt CRISPR (Invivogen: A21174) in order to guide the Cas9 double stranded DNA endonuclease to a specific site within exon 6 of the ERBB2 gene in order to isolate erbB2−/− HEK293 cells & erbB2−/− SKBR3 cells.

HEK293−/− cells and SKBR3−/− cells were then transfected with an ERBB2 expression vector (pUNO1-ERBB2) using the FuGENE HD transfection reagent (Promega Catalogue No E2311). Positive clones were enriched using fluoresce activated cell sorting and a FITC labelled anti-erbB2 monoclonal antibody (Abcam, ab31891). Stable clones were isolated and characterized for ADCC activity in the presence of the iLite® effector cells and Herceptin and then sub-cloned. Suitable sub-clones were isolated, characterized and propagated, giving rise to the erbB2++ KEK293 & erbB2++ SKBR3 target cell lines.

The response of iLite® effector cells & erbB2++ HEK293 target cells, (expressed as fold induction relative to the control sample without Herceptin), was found to be significantly greater than that of the NFAT effector cells & wild type SKBR3 target cells (FIG. 13). The response of iLite® effector cells & wild type SKBR3 target cells, was less than that obtained with the erbB2 HEK293++ target cells but was nevertheless significantly greater than that observed with the NFAT effector cells and wild type SKRB3 target cells (FIG. 14). The response of iLite® effector cells and erbB2−/− target cells, at the same E:T ratio as that used for the erbB2++ target cells, to the presence of increasing concentrations of Herceptin was not significantly different from that of the control sample without Herceptin.

Vials of iLite® effector cells and vials of erbB2++ HEK293 & erbB2++ SKBR3 target cells were frozen separately using standard techniques. Upon thawing, effector cells and target cells were mixed at E:T ratios ranging from 24:1 to 2:1 and incubated for 6 hours in a 96-well white sided microtiter plate (Perkin Elmer 6005181) in the presence of increasing concentrations of Herceptin in RPMI 1640 culture medium+10% fetal bovine serum (FBS). FL activity was then determined using the dual luciferase substrate and light emission was quantified in a luminometer (GloMax, Promega) and expressed as relative luciferase units (RLU). Results are presented as in the form of a 4 parametric logistic (4PL) plot as shown in FIGS. 15A & 15B. The associated Table to FIG. 15A outlines the principal 4PL parameters for the iLite® effector cells and the erbB2++ HEK293 target cells at different E:T ratios and FIGS. 16A & 16B and associated table show the data obtained with the iLite® effector cells and the erbB2++ SKBR3 target cells. An E:T ratio of 1.5:1 was found to be optimal after 6 hours incubation of the iLite® effector and both HEK293 erbB2++ target cells (FIGS. 15A & 15B) and SKBR3 erbB2++ target cells (FIGS. 16A & 16B). The level of *Renilla* luciferase expression in the iLite® effector cells did not increase as a function of the E:T ratio using either the erbB2++ HEK293 target cells (FIG. 15C) or the erbB2SKBR3 target cells and can thus be used as a normalization gene.

Example 4: Establishment of an Engineered Target Cell Line Expressing High Constant Levels of mTNFα at the Cell Surface Quantification of the ADCC activity of TNFα antagonists requires a target cell expressing membrane bound TNFα. Although TNFα is initially membrane bound it is subsequently cleaved by ADAM17 (TACE) protease. Thus, in order to establish a cell line that expresses membrane-bound non-cleavable TNFα site-directed mutagenesis was used to mutate the protease cleavage suite in order to change amino acids AV to LL at position 76-77 of the gene encoding human TNFα (FIG. 17; SEQ ID NO:12).

Non-cleavable TNFα expressed on the surface of a cell will bind, however, to the TNFαRII receptor present on the surface of neighboring cells resulting in cell death and rendering the establishment of a permanent cell line difficult. Thus, or order to obviate such difficulties the TNFαRII receptor was invalidated using genome editing.

The gene encoding the TNFαRII receptor was invalidated in HEK293 cells (ATCC® CRL-1573) using CRISPR-Cas9 genome editing (7). Briefly two guide RNA sequences (FIG. 18) were designed, synthesized and cloned into the nuclease vector GeneArt CRISPR (Invivogen: A21174) in order to guide the Cas9 double stranded DNA endonuclease to a specific site within exon 2 of the TNFαRII gene located on chromosome 12 and exon 2 of the TNFαRII gene located on chromosome 1 in order to isolate TNFαRII−/− HEK293 cells.

Stable clones were isolated and characterized for ADCC activity in the presence the iLite® effector cells and Remicade (infliximab) and then sub-cloned. A suitable sub-clone was isolated, characterized and propagated giving rise to the mTNFα target cell line mTNF6.10 (FIG. 19). The iLite® effector cells and the mTNF++ target cells were then used to quantify the ADCC activity of Remicade (infliximab) as shown for cells in culture in FIG. 19. The iLite® effector cells and the mTNF−/− target cells exhibited no detectable ADCC activity at concentrations of infliximab up to 1.0 µg/ml after 6-hours incubation (FIG. 19).

Vials of iLite® effector cells and vials of mTNF++ target cells target cells were frozen separately using standard techniques. Upon thawing, effector cells and target cells were mixed at E:T ratios ranging from 24:1 to 2:1 and incubated for 6 hours in a 96-well white sided microtiter plate (Perkin Elmer 6005181) in the presence of increasing concentrations of Remicade in RPMI 1640 culture medium+ 10% fetal bovine serum (FBS). FL activity was then determined using the dual luciferase substrate and light emission was quantified in a luminometer (GloMax, Promega) and expressed as relative luciferase units (RLU). Results are presented as in the form of a 4 parametric logistic (4PL) plot as shown in FIGS. 20 A & 20 B. The associated Tables to FIGS. 20 A & 20 B outline the principal 4PL parameters for the iLite® effector cells and mTNF++ target cells at different E:T ratios (FIGS. 20 A & 20 B). An E:T ratio of 3:1 was found to be optimal after 6 hours incubation of the effector and target cells (FIGS. 20 A & 20 B). The level of RL expression did not increase as a function of the E:T ratio (FIG. 21) and can be used as a normalization gene.

Patients treated with therapeutic antibodies often respond in a different manner to therapy and some patients also develop anti-drug antibodies (ADA) that can negatively impact their ability to respond to therapy. Thus, there is a need to monitor individual patients over time both for circulating levels of the therapeutic antibody and for anti-drug antibodies. Furthermore, since the activity of a number of therapeutic antibodies is mediated in part by antibody-dependent cell-mediated cytotoxicity there is a need to monitor patients for the ADCC activity of the therapeutic antibody. This is rendered difficult, however, due to the high concentration of IgG present in human serum that can bind to the surface of the target cells resulting in a nonspecific increase the activity of the effector cells that can confound the results obtained.

The use of homologous target negative cells in which the specific drug target has been invalidated by genome editing provides a means of estimating the level of non-specific activation in the presence of the target negative cells and a given concentration of human serum that can be subtracted from that observed with the homologous cells expressing the specific drug target in the presence of the same concentration of human serum using the following formula: [(E+T++Drug+NHS)−(E+T−+NHS)+(E+T+)]/E+T+, or [(E+T++NHS)−(E+T−+NHS)+(E+T+)]/E+T+, wherein (E)=effector cells, (T+)=antigen positive target cells, (T−)=antigen negative target cells, and NHS=normal human serum sample. This technique has been use to quantity the ADCC activity of the TNFα antagonist infliximab in samples of serum from patients with Crohn's disease (Table 1). A reading for Target ++/Target −/− cells of 5.0 or greater was considered to be positive from the results obtained from the control samples with and without a 1/20 final dilution of normal human serum (Table 1). Thus, samples 1, 3, and 9 were found to exhibit ADCC activity using this technique (Table 1). Samples 1, 3, and 9 were also found to contain detectable levels of infliximab using either an ELISA (Matriks Bioteck, TR-QS-INF) or bioassay (8) as described previously (Table 1).

TABLE 1

Quantification of ADCC Activity of Infliximab in Patients with Crohn's Disease.

| | Infliximab | | | | | | | |
|---|---|---|---|---|---|---|---|---|
| | ADCC Reporter Gene Assay | | | | Residual Drug | | ADA | |
| Sample | Target Negative Cells (RLU) | Target Positive Cells (RLU) | Target+/ Target− | Serum Sample/Control | Bioassay (% of Drug Activity) | ELISA (µg/ml) | Bioassay (% of Drug activity) | ELISA (µg/ml) |
| No Hum. Serum | 1122 | 4264 | 3.80 | 0.33 | 0% | 0.026 | 0% | 0 |
| Hum. Serum | 2607 | 12830 | 4.92 | 1.00 | 0% | 0.026 | 14% | 0 |
| No Hum. Serum + Infliximab | 1382 | 39370 | 28.49 | 3.07 | 100% | 3 | 80% | 0.7 |
| Hum. Serum + Infliximab | 1902 | 39075 | 20.55 | 3.05 | 100% | 3 | 79% | 0.7 |
| Patient Sample 1 | 1975 | 36750 | 18.61 | 2.86 | 100% | 2.58 | 90% | 0 |
| Patient Sample 2 | 3490 | 17315 | 4.96 | 1.35 | 33% | 0.033 | 80% | 0 |
| Patient Sample 3 | 2032 | 11740 | 5.78 | 0.92 | 40% | 0.032 | 83% | 0 |
| Patient Sample 4 | 1607 | 7422 | 4.62 | 0.58 | 0% | 0.025 | 89% | 0 |
| Patient Sample 5 | 3619 | 15380 | 4.25 | 1.20 | 0% | 0.027 | 81% | 0 |
| Patient Sample 6 | 1456 | 6900 | 4.74 | 0.54 | 17% | 0.026 | 79% | 0 |
| Patient Sample 7 | 1826 | 7228 | 3.96 | 0.56 | 17% | 0.025 | 0% | 0.554 |
| Patient Sample 8 | 1189 | 4756 | 4.00 | 0.37 | 0% | 0.025 | 0% | 0.515 |
| Patient Sample 9 | 2494 | 51750 | 20.75 | 4.03 | 100% | 0.97 | 79% | 0 |
| Patient Sample 10 | 1605 | 4882 | 3.04 | 0.38 | 17% | 0.025 | 84% | 0 |
| Patient Sample 11 | 1721 | 7670 | 4.46 | 0.60 | 33% | 0.027 | 81% | 0 |
| Patient Sample 12 | 1312 | 4724 | 3.60 | 0.37 | 17% | 0.025 | 83% | 0 |
| Patient Sample 13 | 2260 | 8855 | 3.92 | 0.69 | 0% | 0.032 | 80% | 0 |
| Patient Sample 14 | 2736 | 9099 | 3.33 | 0.71 | 33% | 0.024 | 21% | 0.503 |
| Patient Sample 15 | 3063 | 12785 | 4.17 | 1.00 | 0% | 0.026 | 91% | 0 |
| Patient Sample 16 | 1984 | 6331 | 3.19 | 0.49 | 0% | 0.025 | 90% | 0 |
| Patient Sample 17 | 1452 | 5628 | 3.88 | 0.44 | 0% | 0.025 | 93% | 0 |
| Patient Sample 18 | 1379 | 4492 | 3.26 | 0.35 | 0% | 0.024 | 90% | 0 |

TABLE 1-continued

Quantification of ADCC Activity of Infliximab in Patients with Crohn's Disease.

| | Infliximab | | | | | | | |
|---|---|---|---|---|---|---|---|---|
| | ADCC Reporter Gene Assay | | | | Residual Drug | | ADA | |
| Sample | Target Negative Cells (RLU) | Target Positive Cells (RLU) | Target+/ Target− | Serum Sample/Control | Bioassay (% of Drug Activity) | ELISA (µg/ml) | Bioassay (% of Drug activity) | ELISA (µg/ml) |
| Patient Sample 19 | 1428 | 5981 | 4.19 | 0.47 | 0% | 0.029 | 87% | 0 |
| Patient Sample 20 | 1250 | 4300 | 3.44 | 0.34 | 0% | 0.025 | 51% | 0.509 |

No ADCC activity was detected in samples 7, 8, 14 & 20 that were found to contain anti-infliximab antibodies determined using a commercially available ELISA (Matriks Bioteck reference TR-ATIv4). Furthermore, the anti-infliximab antibodies detected by ELISA were shown to be neutralizing using a bioassay (8)

The ADCC activity of adalimumab and etanercept was also quantified in samples of serum from patients with rheumatoid arthritis (Table 2). Thus, samples 7 to 11 and sample 17 from patients treated with etanercept were found to contain readily detectable ADCC activity (Table 2). Similarly, samples 4, 5, 8, 12, 13, 14, 17, & 19 from patients treated with adalimumab were also found to contain readily detectable ADCC activity (Table 2).

TABLE 2

Quantification of ADCC Activity of Etanercept & Adalimumab in Patients with Rheumatoid Arthritis

| | ADCC Reporter Gene Assay | | | |
|---|---|---|---|---|
| Sample | Target Negative Cells (RLU) | Target Positive Cells (RLU) | Target+/ Target− | Serum Sample/ Control |
| Etanercept | | | | |
| No Hum. Serum | 1428 | 4386 | 3.07 | 0.51 |
| Hum. Serum | 2251 | 8541 | 3.79 | 1.00 |
| No Hum. Serum + Etanercept | 1610 | 22755 | 14.13 | 2.66 |
| Hum. Serum + aEtanercept | 1810 | 23655 | 13.07 | 2.77 |
| Patient Sample 1 | 2843 | 8235 | 2.90 | 0.96 |
| Patient Sample 2 | 1275 | 4019 | 3.15 | 0.47 |
| Patient Sample 3 | 1255 | 3082 | 2.46 | 0.36 |
| Patient Sample 4 | 1195 | 3853 | 3.22 | 0.45 |
| Patient Sample 5 | 1347 | 5075 | 3.77 | 0.59 |
| Patient Sample 7 | 1583 | 11718 | 7.40 | 1.37 |
| Patient Sample 8 | 1384 | 9794 | 7.08 | 1.15 |
| Patient Sample 9 | 1595 | 11960 | 7.50 | 1.40 |
| Patient Sample 10 | 1297 | 5803 | 4.47 | 0.68 |
| Patient Sample 11 | 1768 | 8445 | 4.78 | 0.99 |
| Patient Sample 12 | 1346 | 4642 | 3.45 | 0.54 |
| Patient Sample 13 | 1579 | 5600 | 3.55 | 0.66 |
| Patient Sample 14 | 1182 | 3240 | 2.74 | 0.38 |
| Patient Sample 15 | 1238 | 4742 | 3.83 | 0.56 |
| Patient Sample 16 | 2303 | 6993 | 3.04 | 0.82 |
| Patient Sample 17 | 2061 | 22040 | 10.69 | 2.58 |
| Patient Sample 18 | 1963 | 5394 | 2.75 | 0.63 |
| Patient Sample 19 | 3275 | 8863 | 2.71 | 1.04 |
| Patient Sample 20 | 2460 | 7338 | 2.98 | 0.86 |
| Adalimumab | | | | |
| No Hum. Serum | 1400 | 4300 | 3.07 | 0.50 |
| Hum. Serum | 2689 | 11310 | 4.21 | 1.00 |
| No Hum. Serum + adalimumab | 1700 | 30000 | 17.65 | 2.65 |
| Hum. Serum + adalimumab | 2200 | 27000 | 12.27 | 2.39 |

TABLE 2-continued

Quantification of ADCC Activity of Etanercept & Adalimumab in Patients with Rheumatoid Arthritis

| | ADCC Reporter Gene Assay | | | |
|---|---|---|---|---|
| Sample | Target Negative Cells (RLU) | Target Positive Cells (RLU) | Target+/ Target− | Serum Sample/ Control |
| Patient Sample 1 | 1733 | 6877 | 3.97 | 0.61 |
| Patient Sample 2 | 4476 | 18495 | 4.13 | 1.64 |
| Patient Sample 3 | 3672 | 14415 | 3.93 | 1.27 |
| Patient Sample 4 | 2527 | 22375 | 8.85 | 1.98 |
| Patient Sample 5 | 2642 | 18495 | 7.00 | 1.64 |
| Patient Sample 7 | 1768 | 6596 | 3.73 | 0.58 |
| Patient Sample 8 | 1935 | 21785 | 11.26 | 1.93 |
| Patient Sample 9 | 1397 | 4398 | 3.15 | 0.39 |
| Patient Sample 10 | 1864 | 6703 | 3.60 | 0.59 |
| Patient Sample 11 | 1933 | 5499 | 2.84 | 0.49 |
| Patient Sample 12 | 1907 | 11670 | 6.12 | 1.03 |
| Patient Sample 13 | 1867 | 12490 | 6.69 | 1.10 |
| Patient Sample 14 | 2014 | 14520 | 7.21 | 1.28 |
| Patient Sample 15 | 2251 | 8091 | 3.59 | 0.72 |
| Patient Sample 16 | 1454 | 5670 | 3.90 | 0.50 |
| Patient Sample 17 | 1583 | 27730 | 17.52 | 2.45 |
| Patient Sample 18 | 2210 | 7537 | 3.41 | 0.67 |
| Patient Sample 19 | 2091 | 17155 | 8.21 | 1.52 |
| Patient Sample 20 | 1567 | 5696 | 3.63 | 0.50! |

Example 5: Establishment of an Engineered Target Cell Line Expressing High Constant Levels of EGFR at the Cell Surface EGFR negative HEK293 cells (ATCC® CRL-1573) cells were transfected with a human EGFRa expression vector (pUNO1-hefgr, Invivogen) using the FuGENE HD transfection reagent (Promega Catalogue No E2311). Positive clones were enriched using fluoresce activated cell sorting and a FITC labelled anti-EGFR monoclonal antibody (R & D Systems, FAB10951P). Stable clones were isolated and characterized for ADCC activity using the iLite® effector cells and cetuximab and then sub-cloned. A suitable sub-clone was isolated, characterized, and propagated giving rise to the EGFR++ target cell line (FIG. 21).

The response of iLite® effector cells & EGFR++ HEK293 target cells, (expressed as fold induction relative to the control sample without cetuximab), as shown in FIG. 21 was found to be significantly greater than that of the NFAT effector cells & EGFR++ HEK293 target cells determined after 6-hours incubation in the presence of cetuximab. Thus, a dynamic range of approximately 60-fold was obtained for the iLite® effector cells & EGFR++ HEK293 target cells versus approximately 2-fold for the NFAT effector cells & EGFR++ HEK293 target cells (FIG. 21 and associated Table).

Vials of iLite® effector cells and vials of EGFR++ target cells target cells were frozen separately using standard techniques. Upon thawing, effector cells and target cells were mixed at E:T ratios ranging from 24:1 to 2:1 and incubated for 6 hours in a 96-well white sided microtiter plate (Perkin Elmer 6005181) in the presence of increasing concentrations of Remicade in RPMI 1640 culture medium+ 10% fetal bovine serum (FBS). FL activity was then determined using the dual luciferase substrate and light emission was quantified in a luminometer (GloMax, Promega) and expressed as relative luciferase units (RLU). Results are presented as in the form of a 4-parametric logistic (4PL) plot as shown in FIGS. 22 A & 22 B. The associated Tables to FIGS. 22 A & 22 B outline the principal 4PL parameters for the iLite® effector cells and EGFR++ target cells at different E:T ratios (FIGS. 22 A & 22 B). An E:T ratio of 6:1 was found to be optimal after 6 hours incubation of the effector and target cells (FIGS. 22 A & 22 B). The level of RL expression did not increase as a function of the E:T ratio and can be used as a normalization gene.

In specific embodiments, the invention also relates to the following items:

Items:
1. An effector cell having a recombinant reporter gene or construct that is activated by NF-AT, AP1, NFkB, and STAT5.
2. A recombinant target cell in which the endogenous target to which an antibody is specific is invalidated.
3. A recombinant target cell in which the expression of the target to which an antibody is specific is enhanced.
4. A regulatory sequence which binds NF-AT, AP1, NFkB, and STAT5, comprising the nucleotide sequence of SEQ ID NO.:1.
5. A kit, comprising:
an effector cell having a recombinant reporter gene assay or construct that is activated by NF-AT, AP1, NFkB, CREB, and STAT5;
a recombinant target cell in which the endogenous target to which an antibody is specific is invalidated (dependent claims, CD20, mTNFα, erbB2 (SKBR3 & HEK293), EGFR);
and
recombinant target cell in which the expression of the target to which an antibody is specific is enhanced. (dependent claims, CD20, mTNFα, erbB2 (SKBR3 & HEK293), EGFR)
6. A method for compensating for the non-specific increase in the reporter-gene signal in the presence of human serum by the subtraction of the signal obtained in the presence of effector cells and target cells, in which the drug target has been invalidated, from the signal obtained in the presence of effector cells and target cells that express the drug target.
7. A method for quantifying the ADCC activity ex vivo in clinical samples from patients treated with therapeutic antibodies.

Moreover, in further specific embodiments present invention also relates to the following articles:
1. A polynucleotide comprising a cis-acting regulatory sequence operably linked to a downstream promotor, wherein one or more of NF-AT, AP1, NFkB, STAT1, STAT3 and STAT5 is capable of binding to said cis-acting regulatory sequence.
2. The polynucleotide according to article 1, characterized in that NF-AT, AP1, NFkB, and STAT5 are all capable of binding to said cis-acting regulatory sequence.
3. The polynucleotide according to any of the preceding articles, wherein the promotor is operable linked to an open read frame sequence encoding a first reporter protein.
4. The polynucleotide according to any of the preceding articles, wherein the reporter is an enzyme
5. The polynucleotide according to any of the preceding articles, wherein the enzyme is e.g. a luciferase.
6. The polynucleotide according to any of the preceding articles, wherein the enzyme is fluorescent protein.
7. The polynucleotide according to any of the preceding articles comprising a nucleotide sequence having at least about 70% sequence identity, such as e.g. at least about 75% sequence identity, such as e.g. at least about 80% sequence identity, such as e.g. at least about 85% sequence identity, such as e.g. at least about 90% sequence identity, such as e.g. at least about 95% sequence identity, such as e.g. at least about 98% sequence identity, such as e.g. at least about 99% sequence identity to SEQ ID NO.: 1 or a DNA sequence identical to SEQ ID NO.: 1
8. A vector construct comprising the polynucleotide according to any of the preceding articles.
9. The vector according to article 8, wherein said vector is a plasmid or viral vector.
10. A cell comprising the vector according to any of articles 8-9.
11. The cell according to article 10, wherein the cell is a mammalian cell.
12. The cell according to article 10 or 11, wherein said vector is episomal or integrated in the genome of said cell.
13. The cell according to any of articles 10-12, wherein the cell further expresses a second reporter protein which different from the first reporter protein.
14. The cell according to any of articles 10-13, wherein the cell is a Jurkat, SKBR3, or HEK293 cells.
15. A kit, comprising:
i) a cell according to any of claims 10-14;
ii) a cell in which the endogenous target to which an antibody is specific is invalidated (mutated); and
iii) a cell in which the expression of the target to which an antibody is specific is enhanced.
16. The kit according to article 15, wherein the target that is invalidated in the target cells in ii) comprises one or more of CD20, mTNFα, erbB2, EGFR.
17. The kit according to article 15, wherein the target that is enhanced in the target cells in iii) comprises one or more of CD20, mTNFα, erbB2, EGFR.
18. The kit according to any of articles 15-17, wherein the kit comprises two vials.
19. The kit according to any of articles 15-18 wherein the cells in i) and iii) are present in one and the same vial at the optimal E:T ratio
20. The kit according to any of articles 15-19, wherein the ratio between the cell in i) and the target cell in iii) (E:T ratio) is in range from about 24:1 to about 2:1, or e.g. about 6:1, or about e.g. 3:1, or about e.g. 1.5:1.
21. A method for quantifying the ADCC activity ex vivo in clinical samples from patients treated with therapeutic antibodies, the method comprising the steps of;
a) contacting a sample obtained from a patient undergoing treatment comprising administration of an antibody, with target cells ii) in article 15, b) subtracting the signal obtained in the presence of cells i), in which the drug target has been invalidated, from the signal obtained in the presence of effector cells i) and target cells iii),
c) determining the ADCC activity on the basis of the signal relationship as measured in a) and b).

22. The method according to article 21, wherein a positive result for a serum sample (i.e. detectable ADCC activity) is present when the signal relationship for Effector cells i) & Target ++ cells iii)/Effector cells i) & Target –/– cells ii)≥1 and wherein a negative result for a serum sample (i.e. no detectable ADCC activity) is present when the value for Effector cells i) & Target ++ cells iii)/value for Effector cells i) & Target –/– cells ii)≤1.

23. A method for compensating for the non-specific increase in the reporter-gene signal in the presence of human serum, the method comprising: subtracting the signal obtained in the presence of cells i), from the signal obtained in the presence of effector cells i) and target cells iii) in article 15, that express the drug target.

24. A method according to article 23 for eliminating serum samples that exhibit activity that is not related to ADCC activity specific to the antibody under investigation when Effector cells & Target negative cells >1

REFERENCES

1. Nash, C. S., et al., Bovine IgG1 but not IgG2 binds to human B cells and inhibits antibody secretion. Immunology, 69:361-366, 1990.
2. Parekh, B. S., et al. Development and validation of an antibody-dependent cell-mediated cytotoxicity reporter gene assay. mABs 4:3, 310-318, 2012
3. Cheng, Z. J., et al. Development of a robust reporter-based ADCC assay with frozen, thaw-and-use cells to measure Fc effector function of therapeutic antibodies. J. Immunol., Methods, 414:69-81, 2014.
4. Kaiser M, Wiggin G R, Lightfoot K, Arthur J S, Macdonald A. MSK regulate TCR-induced CREB phosphorylation but not immediate early gene transcription. Eur J Immunol. 2007 September; 37(9):2583-95.
5. Haubert D, Weckbecker G Vav1 couples the T cell receptor to cAMP response element activation via a PKC-dependent pathway. Cell Signal. 2010 June; 22(6): 944-54.
6. Aramburu J1, Azzoni L, Rao A, Perussia B. Activation and expression of the nuclear factors of activated T cells, NFATp and NFATc, in human natural killer cells: regulation upon CD16 ligand binding. Exp Med. 1995 Sep. 1; 182(3):801-10.
7. Mali, P., Yang, L., Esvelt, K. M., Aach, J., Guell, M., DiCarlo, J. E., Norville, J. E., Church, G. M. (2013) RNA Guided Human Genome Engineering via Cas9. Science. 339:6121, 823-826.
8. Lallemand et al. Reporter gene assay for the quantification of the activity and neutralizing antibody response to TNFα antagonists. J. Immunol. Methods, 373:229-239, 2011.

The invention claimed is:

1. A polynucleotide comprising the DNA sequence of SEQ ID NO: 1 operably linked to a downstream promoter, wherein the DNA sequence of SEQ ID NO: 1 is a cis acting regulatory sequence.

2. The polynucleotide according to claim 1, wherein the promotor is operably linked to an open read frame sequence encoding a first reporter protein.

3. The polynucleotide according to claim 2, wherein the reporter protein is an enzyme or a fluorescent protein.

4. A vector construct comprising the polynucleotide according to claim 2.

5. The vector according to claim 4, wherein said vector is a plasmid or viral vector.

6. A cell comprising the vector according to claim 4.

7. The cell according to claim 6, wherein said vector is episomal or integrated in the genome of said cell.

8. The cell according to claim 6, wherein the cell further expresses a second reporter protein which is different from the first reporter protein.

9. A kit comprising:
   i) a cell according to claim 6, capable of binding to the Fc region of an antibody by the Fc gamma receptors expressed on said cell;
   ii) a cell (T−) in which the endogenous target/antigen to which said antibody is specific is invalidated such that the target/antigen is not expressed by the cell; and
   iii) a target cell (T+) in which the expression of the target to which said antibody is specific is expressed by the cell.

10. A kit according to claim 9, wherein the T− cell and the T+ cell are identical except that the T− cell does not express a specific antigen recognized by the antibody or a drug being assayed.

11. The kit according to claim 9, wherein the target/antigen is CD20, mTNFα, erbB2, and/or EGFR.

12. The kit according to claim 9, which comprises two vials and wherein the cells in i) and iii) are present in the same vial at an optimal effector cell to target cell (E:T) ratio.

13. The kit according to claim 9, wherein the ratio between the effector cell in i) and the target cell in iii) (E:T ratio) is 24:1 to 2:1, 6:1, 3:1, or 1.5:1.

14. A method for quantifying the Antibody-Dependent Cell-mediated Cytotoxicity (ADCC) activity ex vivo in clinical samples from patients treated with therapeutic antibodies, the method comprising the steps of:

a) contacting a sample obtained from a patient undergoing therapeutic antibody treatment with target cells (T+) which express the target to which said therapeutic antibody is specific, b) subtracting the signal obtained in the presence of cells (T−) in which the endogenous target/antigen to which said therapeutic antibody is specific is invalidated such that the target/antigen is not expressed by the cell, from the signal obtained in the presence of effector cells (E), wherein the effector cell is the cell according to claim 6, capable of binding to the Fc region of an antibody by the Fc gamma receptors expressed on said effector cells and target cells T+, c) determining the ADCC activity on the basis of the signal relationship as measured in a) and b), and wherein a positive result for a serum sample is present when the signal relationship for Effector cells E & T+ cells/Effector cells E & T− cells ≥1 and wherein a negative result for a serum sample is present when the value for Effector cells E & T+ cells/value for Effector cells E & T− cells ≤1, using the formula [(E+T++Drug+NHS)−(E+T−+NHS)+(E+T+)]/E+T+, or [(E+T++NHS)−(E+T−+NHS)+(E+T+)]/E+T+, wherein NHS=normal human serum sample.

15. A method for compensating for the non-specific increase in the reporter-gene signal in the presence of human serum, the method comprising: subtracting the signal obtained in the presence of effector cells (E), wherein the effector cell is the cell according to claim 6, capable of binding to the Fc region of an antibody by the Fc gamma receptors expressed on said effector cells, from the signal obtained in the presence of effector cells E and target cells (T+) which express the target to which said antibody is specific, that express the drug target or serum samples that exhibit activity that is not related to ADCC activity specific to the antibody under investigation when Effector cells E & Target negative cells (T−) in which the endogenous target/antigen to which said antibody is specific is invalidated such that the target/antigen is not expressed by the cell, >1, using the formula [E+T++Drug+NHS)−(E+T−+NHS)+(E+T+)]/E+T+, or [E+T++NHS)−(E+T−+NHS)+(E+T+)]/E+T+, wherein NHS=normal human serum sample.

16. The polynucleotide according to claim 3, wherein the enzyme is a luciferase.

17. The method of claim 14, wherein the positive result for a serum sample is characterized by detectable ADCC activity and the negative result for a serum sample is characterized by no detectable ADCC activity.

* * * * *